US010585916B1

(12) United States Patent
Burton et al.

(10) Patent No.: US 10,585,916 B1
(45) Date of Patent: Mar. 10, 2020

(54) SYSTEMS AND METHODS FOR IMPROVED EFFICIENCY

(71) Applicant: Health Catalyst, Inc., Salt Lake City, UT (US)

(72) Inventors: David A Burton, Salt Lake City, UT (US); Thomas D Burton, Salt Lake City, UT (US); Steven C Barlow, Bountiful, UT (US)

(73) Assignee: Health Catalyst, Inc., Salt Lake City, UT (US)

(*) Notice: Subject to any disclaimer, the term of this patent is extended or adjusted under 35 U.S.C. 154(b) by 302 days.

(21) Appl. No.: 15/288,801

(22) Filed: Oct. 7, 2016

(51) Int. Cl.
| *G06F 16/28* | (2019.01) |
| *G06F 16/242* | (2019.01) |
| *G06F 16/25* | (2019.01) |
| *G06F 16/2455* | (2019.01) |
| *G16H 50/30* | (2018.01) |
| *G16H 10/60* | (2018.01) |

(52) U.S. Cl.
CPC .......... *G06F 16/283* (2019.01); *G06F 16/244* (2019.01); *G06F 16/24556* (2019.01); *G06F 16/254* (2019.01); *G16H 10/60* (2018.01); *G16H 50/30* (2018.01)

(58) Field of Classification Search
CPC ......... G06F 17/30592; G06F 17/30412; G06F 17/30489; G06F 17/30563; G06F 16/283; G06F 16/244; G06F 16/254; G06F 16/24556; G16H 50/30; G16H 10/60
USPC ....................................................... 707/600
See application file for complete search history.

(56) References Cited

U.S. PATENT DOCUMENTS

| 6,044,374 A | * | 3/2000 | Nesamoney | G06F 16/283 |
| 7,970,728 B2 | * | 6/2011 | Honzal | G06F 16/283 707/600 |
| 8,984,017 B2 | * | 3/2015 | Naeymi-Rad | G06Q 50/22 707/796 |
| 9,171,104 B2 | * | 10/2015 | Gotz | G06F 17/30991 |
| 9,460,171 B2 | * | 10/2016 | Marrelli | G06F 16/258 |
| 9,720,958 B2 | * | 8/2017 | Bagehorn | G06F 16/244 |
| 2003/0046114 A1 | * | 3/2003 | Davies | G06Q 10/10 705/3 |
| 2005/0108256 A1 | * | 5/2005 | Wakefield | G06F 17/30569 |
| 2005/0228777 A1 | * | 10/2005 | Kruse | G06Q 40/00 |
| 2008/0040181 A1 | * | 2/2008 | Freire | G06Q 10/06316 705/7.26 |
| 2008/0046292 A1 | * | 2/2008 | Myers | G06F 17/30557 705/3 |
| 2009/0156906 A1 | * | 6/2009 | Liebman | A61B 5/00 600/300 |
| 2011/0077973 A1 | * | 3/2011 | Breitenstein | G06Q 10/10 705/3 |
| 2013/0275361 A1 | * | 10/2013 | Hoffman | G06F 17/30899 707/602 |

(Continued)

OTHER PUBLICATIONS

Hoo, Jr., Kent Soo, et al., "Brain imaging for neurologic diagnosis and research", Medical Imaging 2002, San Diego, CA, Proc. of SPIE, vol. 4685, © 2002, pp. 117-127.*

*Primary Examiner* — Robert Stevens
(74) *Attorney, Agent, or Firm* — Patent Law Works LLP

(57) ABSTRACT

Systems and methods for improving efficiency are described herein. The systems and methods described herein can also comprise systems and methods for reducing waste. Systems and methods described herein can comprise a date warehouse, data marts, and visualizations.

18 Claims, 40 Drawing Sheets

(56) References Cited

U.S. PATENT DOCUMENTS

| | | | | |
|---|---|---|---|---|
| 2015/0234987 A1* | 8/2015 | Laing | ............ | G06F 19/00 |
| | | | | 705/3 |
| 2015/0317337 A1* | 11/2015 | Edgar | ............ | G06F 17/30 |
| | | | | 707/751 |
| 2015/0363566 A1* | 12/2015 | Johnson | ............ | G06F 19/3481 |
| | | | | 705/3 |
| 2016/0063191 A1* | 3/2016 | Vesto | ............ | G06F 19/324 |
| | | | | 705/2 |
| 2016/0140303 A1* | 5/2016 | Esrailian | ............ | G06Q 50/22 |
| | | | | 705/3 |
| 2016/0147938 A1* | 5/2016 | McConnell | ............ | G06F 19/321 |
| | | | | 715/763 |
| 2016/0147946 A1* | 5/2016 | Von Reden | ............ | G16H 10/60 |
| | | | | 705/3 |
| 2016/0147954 A1* | 5/2016 | Ng Tari | ............ | G16H 40/20 |
| | | | | 705/3 |
| 2016/0147971 A1* | 5/2016 | Kolowitz | ............ | G06F 3/0481 |
| | | | | 715/753 |
| 2016/0210315 A1* | 7/2016 | Wenda | ............ | G06Q 40/12 |
| 2016/0371441 A1* | 12/2016 | Day | ............ | G16H 40/20 |
| 2017/0124176 A1* | 5/2017 | Beznos | ............ | G06F 17/30598 |
| 2017/0124659 A1* | 5/2017 | Drennan, III | ............ | G06Q 40/08 |
| 2017/0195183 A1* | 7/2017 | Gershaft | ............ | H04L 41/12 |
| 2018/0011739 A1* | 1/2018 | Pothula | ............ | G06F 9/50 |

* cited by examiner

PCS Clinical Care Unit Defect Waste Distribution Chart 400C

| Value Stream Map | Diagnostic CSS | | | Ambulatory CSS | | Acute Medical CSS | | | Invasive CSS | | Interv Med |
|---|---|---|---|---|---|---|---|---|---|---|---|
| | Clin Path | Anat Path | Radiology | Peds | Adult | ECU | ICU/CCU | Med-Surg | IP Surg | ASC | |
| Substances | | | | | | | | | | | |
| Pharmacy | | | | x | x | x | x | x | x | x | x |
| Medications | | | x | x | x | x | x | x | x | x | x |
| Fluids | | | | x | | x | x | x | x | x | x |
| Electrolytes | | | | x | x | x | x | x | x | x | |
| Parenteral Nutrition (TPN) | | | | | | x | x | x | x | | |
| Transfusion Medicine | | | | | | x | x | x | x | | |
| Glycemic Control (Glucose Mgmt) | | | | | | | x | x | x | x | |
| Healthcare Associated Infections | | | | | | | | | | | |
| Ventilator Associated Pneumonia | | | | | | | x | | | | |
| Urinary Catheter Infections | | | | | | x | x | x | x | x | x |
| Surgical Site Infections | | | | | | x | | x | x | x | x |
| Central Line Assoc Bloodstream Inf | | | | | | | x | x | x | x | |
| Venous Thromboembolism | | | | | | | x | x | x | | |
| Pressure Injury (Decubitus Ulcer) | | | | | | x | x | x | | x | |
| Falls (Strength Agility Cognition) | | | | | | | x | x | | | |
| Patient/Procedure Control | | | | | | | | | x | x | |

FIG. 4C

Waste reduction process – key process analysis

| RANK | Clinical Program | Key Process Family | % of Total Opportunity | Cumulative % |
|---|---|---|---|---|
| 1 | Cardiovascular | Heart Failure | 6.9% | 6.9% |
| 2 | Neuroscience | Spine | 5.8% | 12.7% |
| 3 | | Infectious Disease | 5.6% | 18.4% |
| 4 | Ortho | Joint Replacement | 5.7% | 24.1% |
| 5 | Gastrointestinal | Bowel Disorders - Surgical | 5.7% | 29.8% |
| 6 | Oncology | Oncology - Treatment | 4.8% | 34.6% |
| 7 | Acute Medical CSS | Mechanical Ventilation | 4.2% | 38.8% |
| 8 | Neuroscience | Craniotomy | 3.9% | 42.7% |
| 9 | Cardiovascular | Vascular | 3.8% | 46.5% |
| 10 | | Pulmonary | 3.4% | 49.9% |
| 11 | | Heart/Lung Transplant | 3.1% | 53.0% |
| 12 | Oncology | Lymphoma and Leukemia | 2.9% | 56.0% |
| 13 | Cardiovascular | Ischemic | 2.9% | 58.9% |
| 14 | | Liver Transplant | 2.7% | 61.6% |
| 15 | Surgery - Other | Trauma | 2.6% | 64.1% |
| 16 | Gastrointestinal | Bowel Disorders - Medical | 2.1% | 66.2% |
| 17 | Ortho | Sports Medicine | 1.8% | 68.1% |
| 19 | Gastrointestinal | Biliary/Pancreas - Surgical | 1.8% | 69.9% |
| 20 | Oncology | Hematology | 1.8% | 71.7% |
| 21 | Surgery - Other | Urologic Surgery | 1.8% | 73.4% |
| 22 | Cardiovascular | Chest Surgery | 1.7% | 75.1% |
| 23 | | Kidney Transplant | 1.5% | 76.6% |
| 24 | Mental Health | I-Mood Disorders | 1.4% | 78.0% |
| 25 | Ortho | Hip and Femur | 1.2% | 79.3% |
| 26 | Cardiovascular | EP | 1.2% | 80.5% |

FIG. 8

SYSTEMS AND METHODS FOR IMPROVED EFFICIENCY

CROSS-REFERENCE TO RELATED APPLICATIONS

This application is a continuation of U.S. patent application Ser. No. 13/913,493, filed on Jun. 9, 2013, which claims priority to U.S. Provisional Patent Application 61/657,778, filed on Jun. 9, 2012; U.S. Provisional Patent Application 61/661,804, filed on Jun. 19, 2012; U.S. Provisional Patent Application 61/669,120, filed on Jul. 8, 2012; U.S. Provisional Patent Application 61/669,121, filed on Jul. 8, 2012; U.S. Provisional Patent Application 61/669,124, filed on Jul. 9, 2012; U.S. Provisional Patent Application 61/669,125, filed on Jul. 9, 2012; U.S. Provisional Patent Application 61/669,126, filed on Jul. 9, 2012; U.S. Provisional Patent Application 61/669,128, filed on Jul. 9, 2012; U.S. Provisional Patent Application 61/684,277, filed on Aug. 17, 2012; U.S. Provisional Patent Application 61/717,179, filed on Oct. 23, 2012; and U.S. Provisional Patent Application 61/717,275, filed on Oct. 23, 2012, all of which are incorporated by reference in their entireties.

SUMMARY

This Summary is provided to introduce a selection of concepts in a simplified form that are further described in the Detailed Description. The features and advantages described herein are not all-inclusive and many additional, or different, features and advantages will be apparent to one of ordinary skill in the art in view of the Figures and Detailed Description. Moreover, it should be noted that the language used in the Specification has been selected principally for readability and instructional purpose, and not to limit the scope of the subject matter herein.

Healthcare delivery improvement techniques are described for leveraging healthcare delivery building blocks, such as evidence-based clinical content and data warehouse functionality, to provide a data-driven infrastructure that allows healthcare to be delivered in a safer and more clinically and cost effective manner.

More particularly, by utilizing these techniques, clinical care can be provided to patients in a way that both improves patient outcomes and reduces or eliminates wasteful patient treatment practices, which may be referred to herein as waste.

In accordance with the described techniques, a waste reduction integration framework can be defined that integrates the ordering of healthcare treatment services (e.g., by clinical programs) with the delivery of those services to patients (e.g., by clinical support services). Techniques can then be implemented within this framework to improve patient outcomes and reduce waste in patient care settings (PCS)s.

To accomplish this, in at least one embodiment evidence-based clinical content and data warehouse functionality can be integrated to provide healthcare delivery waste reduction tools, such as patient treatment knowledge assets (KA)s, analytical feedback, and deployment tools that facilitate waste being significantly reduced or eliminated altogether. In some examples, the data warehouse can be an enterprise data warehouse (EDW). In the same or other examples, the date warehouse can be an adaptable date warehouse (ADW).

For example, clinical content can be utilized to create KAs that include treatment criteria associated with the ordering of healthcare services, the delivery of healthcare services, and/or patient safety. Furthermore, a knowledge information toolkit (KIT) may be utilized to create KA starter sets that can then be customized for a PCS. Alternatively or additionally, the KIT may be utilized (e.g., by the PCS subject matter experts) to perform this customization.

Once the KAs have been created (e.g., as KA starter sets), and in some circumstances customized as PCS-specific KAs, their treatment criteria can be utilized to create subject area marts (SAM)s for the PCS's ADW. It should be noted that ADWs are one type of data warehouse, and that others can also be used. Data extraction routines of these SAMs can be based on these treatment criteria. As discussed below, these data extraction routines can allow the treatment criteria to be tracked as key indicators via the PCS's ADW.

In at least one embodiment, the KIT may also be utilized to create SAM starter sets that can then be customized for the PCS. Alternatively or additionally, PCS subject matter experts and/or others may utilize the KIT to perform this customization. Once the SAMs (e.g., SAM starter set(s) and/or PCS-specific SAM(s)) have been created, the SAMs' treatment criteria can be utilized to track the PCS's patient treatment practices and outcomes. As noted above, in operation this can be accomplished by tracking the criteria as key indicators.

Based on the tracked patient treatment practices and outcomes, analytical feedback can be provided (e.g., prepared, shared, and/or utilized). In at least one embodiment, this can be accomplished at least in part by performing a key process analysis (KPA) utilizing the tracked patient treatment practices and outcomes. In the same or other embodiments, visualizations can be used to provide analytical feedback.

In at least one embodiment, the analytical feedback can include visualizations (e.g., reports, dynamic dashboards, charts, etc.) that identify waste and/or allow the PCS to assess whether or not its treatment practices adhere to the treatment criteria. This assessment can include scrutinizing the tracked treatment practices down to a very granular level (e.g., date/time, treatment setting, practitioner(s), patient, etc.). In some circumstances, individual SAMs can be modified, removed, and/or added by the PCS and/or others based on this assessment.

To facilitate the PCS in adopting and/or customizing the KAs, SAMs, analytical feedback, and in implementing treatment changes to reduce or eliminate identified waste, deployment tools can be provided. These deployment tools can include deployment visualizations, consultative services, recommendations, and/or implementation tools.

BRIEF DESCRIPTION OF THE DRAWINGS

The accompanying drawings illustrate implementations of the concepts conveyed in the present application. Features of the illustrated implementations can be more readily understood by reference to the following description taken in conjunction with the accompanying drawings.

FIGS. 4, 4A, 4B, and 4C illustrate an example technique or method that may be implemented, in accordance with at least one embodiment.

FIGS. 8-12 illustrate example analytical feedback visualizations that may be prepared in accordance with at least one embodiment.

DETAILED DESCRIPTION

Overview

Figure 1:
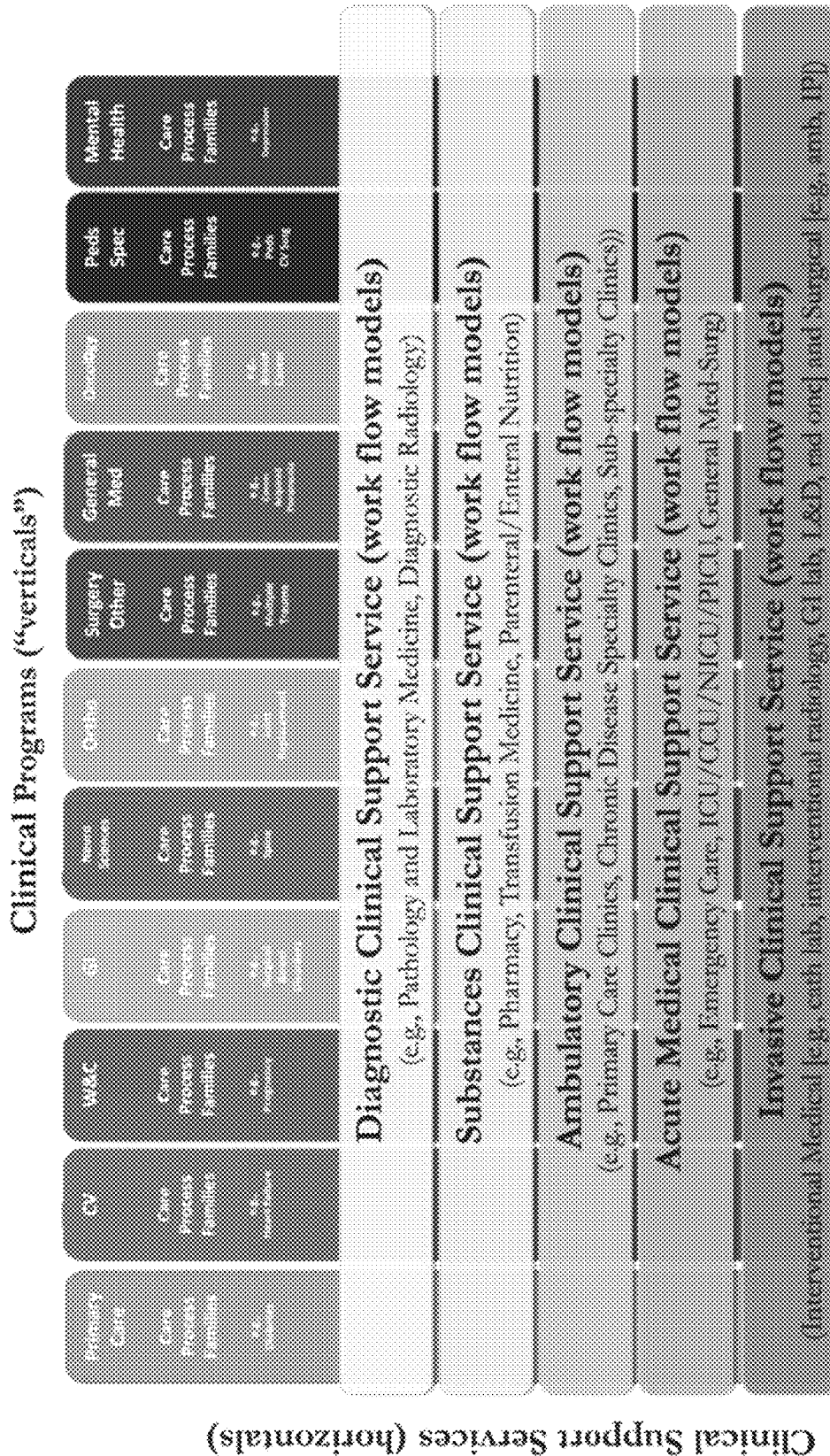
FIG. 1 illustrates an example representation of a waste reduction integration framework, in accordance with at least one embodiment.

Healthcare delivery improvement techniques are described for leveraging healthcare delivery building blocks, such as evidence-based clinical content and data warehouse functionality, to provide a data-driven infrastructure that allows healthcare to be delivered in a safer and more clinically and cost effective manner.

More particularly, by utilizing these techniques, clinical care can be provided to patients in a manner that both improves patient outcomes and reduces or eliminates wasteful (i.e., inefficient and/or ineffective) patient treatment (i.e., care) practices, which may be referred to herein as waste.

Two examples of waste include variations in the ordering and delivery of treatment in a patient care setting (PCS), such as a hospital or patient care clinic for instance. Another example of waste might be a complication or defect resulting from a patient's treatment, such as an adverse drug event, fall, etc. These three types of waste may be referred to respectively as ordering waste, delivery waste, and defect waste.

In accordance with the described techniques, a waste reduction integration framework can be defined that integrates the ordering of healthcare services (e.g., by clinical programs) with the delivery of those services to patients (e.g., by clinical support services). Techniques can then be implemented within this framework to improve patient outcomes and reduce waste in patient care settings.

To accomplish this, in at least one embodiment evidence-based clinical content and adaptable data warehouse (ADW) functionality can be integrated to provide healthcare delivery waste reduction tools, such as patient treatment knowledge assets (KA)s, analytical feedback, and deployment tools that facilitate waste being significantly reduced or eliminated altogether. It should be noted that ADWs are one type of data warehouse, and that others can also be used.

For example, clinical content can be utilized to create KAs that include treatment criteria. The treatment criteria can include, for example, criteria associated with the ordering of healthcare services, the delivery of healthcare services, and/or patient safety.

Furthermore, the treatment criteria can be measured and thus tracked as indicators via a PC S's ADW. As such, these indicators may be considered actionable and deployable with respect to tracking actual treatment practices and outcomes of the PCS to identify waste resulting from the ordering or delivery of the treatment, and/or from patient complications from this treatment.

In at least one embodiment, one or more of the KAs may be created as KA starter sets that have not been customized (i.e., refined, fingerprinted, and/or otherwise modified) for a particular PCS, and are thus not PCS-specific. These KA starter sets may then be provided to the PCS's subject matter experts (e.g., clinical practitioners, physicians, nurses, allied health practitioners, administrators, etc.) and/or others to customize and adapt them as PCS-specific KAs.

In at least one embodiment, a knowledge information toolkit (KIT) may be utilized to facilitate creating these KA starter sets. Alternatively or additionally, the KIT may be utilized by the subject matter experts and/or others to customize individual KA starter sets.

Once the KAs have been created (e.g., as KA starter sets), and in some circumstances customized to become PCS-specific KAs, they can be utilized to create subject area marts (SAM)s for the PCS's ADW. For purposes of discussion, a SAM may be thought of as an ADW data construct that provides a relatively narrow and specific set of data (by virtue of data extraction routines) associated with one or more particular groups, or cohorts, of patients sharing a similar event, such as, for example, having a similar diagnosis.

SAM's data extraction routines can be based on certain treatment criteria selected from the KA(s) utilized to create that SAM. As discussed below, these data extraction routines allow these criteria to be tracked as key indicators via the PCS's ADW.

Similar to KA starter sets, in at least one embodiment, one or more of the SAMs can be created as SAM starter sets that have not been customized for the PCS, and are thus not PCS-specific. These SAM starter sets may then be provided to the PCS's subject matter experts and/or others to customize and adapt them into PCS-specific SAMs.

In at least one embodiment, a KIT may be utilized to facilitate creating the SAMs, including SAM starter sets. For example, the KIT can be used to identify or define the cohort for a SAM and to select (e.g., at least in part automatically) criteria (from a KA(s)) for the SAM to be tracked as key indicators via the PCS's ADW. Alternatively or additionally, the KIT may be utilized by the subject matter experts and/or others of the PCS to customize individual SAM starter sets.

Once the SAMs (e.g., SAM starter set(s) and/or PCS-specific SAM(s)) have been created, the SAMs' treatment criteria can be utilized to track the PCS's patient treatment practices and outcomes. As noted above, in operation this can be accomplished by tracking the criteria as key indicators via the PCS's ADW.

Based on the tracked patient treatment practices and outcomes, analytical feedback can be provided (e.g., prepared, shared, and/or utilized). In at least one embodiment, this can be accomplished at least in part by performing a key process analysis (KPA) utilizing the tracked patient treatment practices and outcomes. In the same or other embodiments, visualizations can be used to provide analytical feedback.

In at least one embodiment, the analytical feedback can include visualizations (e.g., reports, dynamic dashboards, charts, etc.) that identify waste and/or allow the PCS to assess whether or not its treatment practices adhere to the treatment criteria. This assessment can include scrutinizing the tracked treatment practices down to a very granular level (e.g., date/time, treatment setting, practitioner(s), patient, etc.).

In some circumstances, individual SAMs can be modified (e.g., customized or otherwise altered), removed, and/or added by the PCS and/or others based on this assessment. For example, subject matter experts and/or others of the PCS may perform one or more of these functions. As noted above, in at least one embodiment, a KIT may be utilized to accomplish this.

To facilitate the PCS in adopting and/or customizing the KAs, SAMs, analytical feedback, and in implementing treatment changes to reduce or eliminate identified waste, deployment tools can be provided. These deployment tools can include deployment visualizations, consultative services, recommendations, and/or implementation tools.

To facilitate the PCS in adopting and/or customizing the KAs, SAMs, and analytical feedback, and in implementing treatment changes to reduce or eliminate identified waste, deployment tools can be provided. These deployment tools can be based on the KAs, analytical feedback, and/or tracked treatment practices. Examples of deployment visualizations can include, without limitation, deployment visualizations, consultative services, recommendations, and or supportive implementation tools. This list is merely demonstrative and additional deployment visualizations can be provided.

Multiple and varied implementations are described herein. Generally, any of the features/functions described with reference to the figures can be implemented using software, hardware, firmware (e.g., fixed logic circuitry), manual processing, or any combination thereof. The terms "module", "tool", and/or "component" as used herein may generally represent software, hardware, firmware, or any combination thereof. For instance, the terms "tool" and "module" can represent software code and/or other types of instructions that perform specified tasks when executed on a computing device or devices.

Generally, the illustrated separation of modules, tools or components and functionality into distinct units may reflect an actual physical grouping and allocation of such software, firmware, and/or hardware. Alternatively or additionally, this illustrated separation can correspond to a conceptual allocation of different tasks to the software, firmware, and/or hardware. Furthermore, it is to be appreciated and understood that the illustrated modules, tools, and/or components and functionality described herein can be located at a single site (e.g., as implemented by a computing device), or can be distributed over multiple locations (e.g., as implemented over multiple computing devices).

Waste

Recall that by utilizing the healthcare delivery improvement techniques described herein, clinical care can be provided to patients in a manner that both improves patient outcomes while also reducing or eliminating waste, such as ordering, delivery waste, and defect waste, respectively. TABLE 1 below summarizes these example forms of waste:

TABLE 1

Example Forms of Healthcare Waste

Ordering Waste: Variation in care ordered or provided for the same condition by different providers. May also be referred to as care process waste or utilization waste.
Delivery Waste: Variation in the delivery of care ordered. May also be referred to as workflow waste.
Defect Waste: Complications resulting from care delivery. May also be referred to as patient harm/injury waste or patient safety waste.

TABLE 2 includes examples of each of these forms of waste and tools that may be utilized to reduce each form of waste:

TABLE 2

Example Waste Reduction Tools and Waste Forms Examples

| Form of Waste | Examples of Tools to Reduce Waste | Example of Waste Form |
|---|---|---|
| Ordering Waste (Utilization Waste) | Clinical effectiveness care algorithms and commercial-grade clinical content. | Ordering of tests that are neither diagnostic nor contributory. |
| Delivery Waste (Workflow Waste) | Value stream maps and A3s (Lean process improvement). | Variation in OR room turnover (cycle) time. |
| Defect Waste | Commercial-grade clinical content and value stream maps (standard work). | Adverse drug events (ADEs), transfusion reactions, HAIs, VTE, pressure injury, falls, wrong surgery. |

Reduction Integration Framework

Recall that in accordance with the described techniques, a waste reduction integration framework can be defined that integrates the ordering of healthcare services (e.g., by clinical programs) with the delivery of those services to patients (e.g., by clinical support services). TABLES 3 and 4 below respectively, each summarize examples of clinical programs and clinical support services, which are examples of healthcare system delivery building blocks that can be conceptually organized in accordance with this integration framework.

TABLE 3

Example Delivery Building Block - Clinical Programs

Clinical Programs can organize into teams those
clinicians who share clinical work
processes (e.g., cardiologists, cardiac
surgeons, chest surgeons, vascular
surgeons for the CV Clinical Program).
Clinical Program physicians may write
the orders (i.e., they can provide ongoing
management and/or are
the attending (admitting) physicians).

TABLE 4

Example Delivery Building Block - Clinical Support Services

Clinical support services can provide
services to patients who belong to multiple
clinical programs. They can implement
Clinical Program physician orders.
Clinical support services may consist of care units
(e.g., ambulatory physician offices,
emergency care unit, Intensive care
units (ICUs), general medical-surgical unit,
operating rooms (ORs), cardiac catheter lab,
interventional radiology, endoscopy lab, etc.).
Clinical support services can focus on patient
treatment work flows.
Clinical support services can be key to identifying
patients who are at risk for harm and preventing
the harm from happening (patient safety waste).

FIG. 1 illustrates an example representation of a waste reduction integration framework in the context of clinical program and clinical support services building blocks that might be associated with the delivery of healthcare by a PCS. Note that the example clinical program building blocks arranged along the horizontal x-axis are referred to as "verticals", while the example clinical support services arranged along the vertical y-axis and are referred to as "horizontals".

Figure 2:
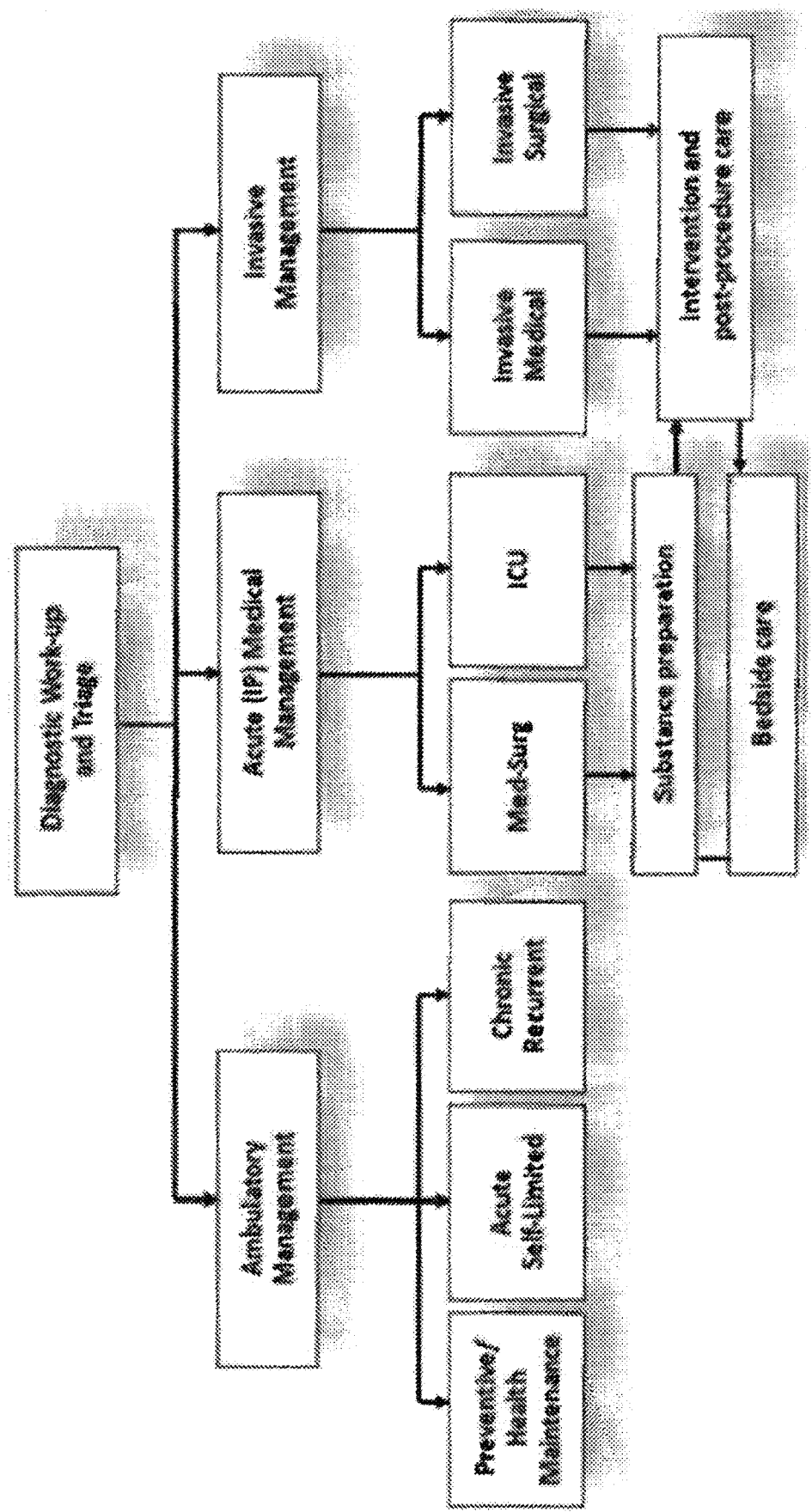
FIGS. 2 and 3 illustrate example healthcare delivery anatomy diagrams, in accordance with at least one embodiment.

To facilitate the reader's understanding of how the example building blocks described above may fit into the anatomy of a PCS, FIG. 2 illustrates an example healthcare delivery anatomy diagram in the context of clinical program building blocks ("verticals"). As an example, a patient arrives at a care facility, such as, for example, a hospital. As can be seen in FIG. 2, the patient can go through a diagnostic work-up and triage. The patient is then sorted according to the patient's risk. For example, if the patient has a low risk, he or she can be sent to ambulatory management for more services. If the patient has a high risk and needs immediate intervention, the patient can be sent to invasive management for more services. In addition, the patient can be sent to acute medical management for more services.

Figure 3:
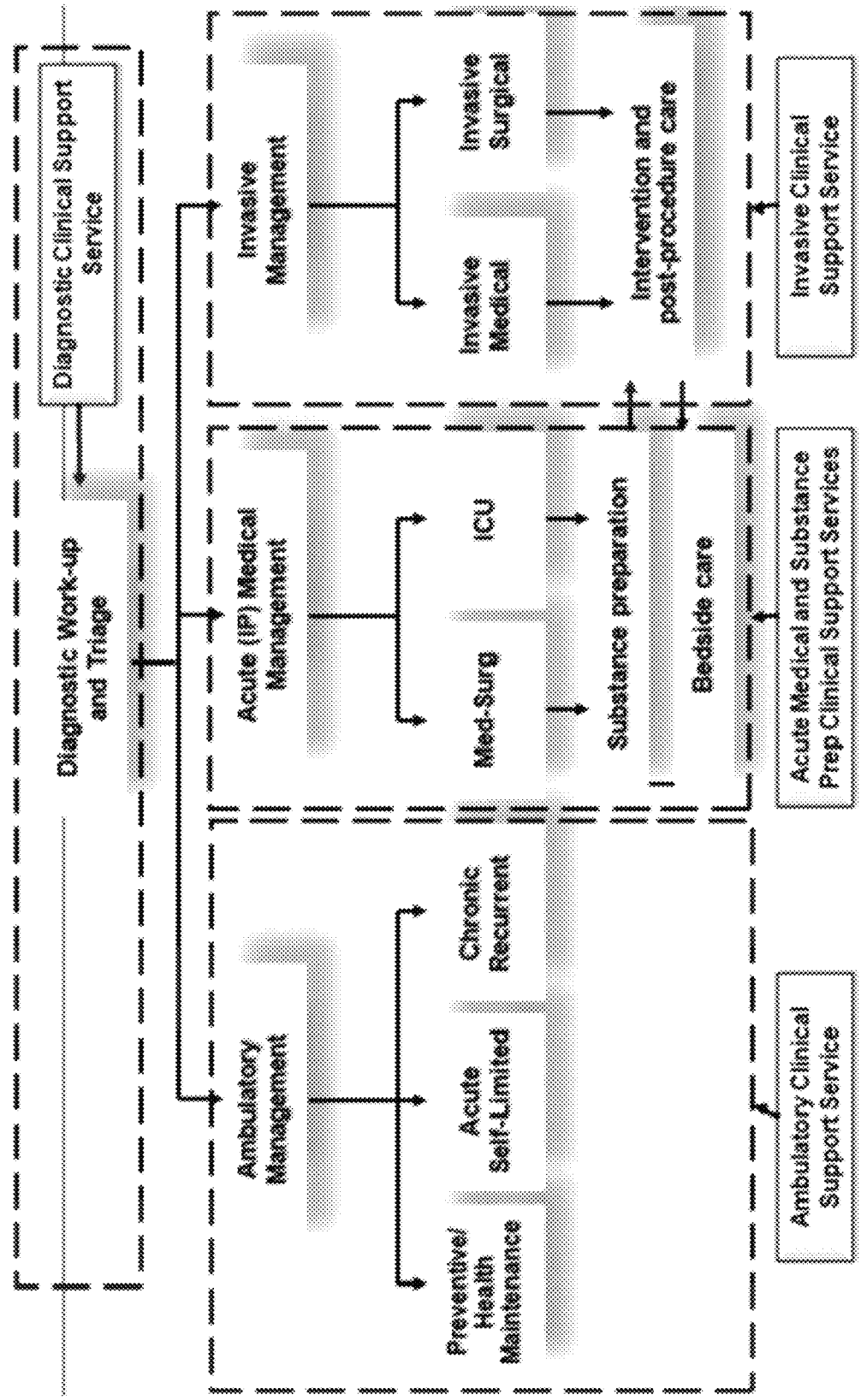

FIG. 3, in turn, illustrates an example healthcare delivery anatomy diagram in the context of both the example clinical program building blocks ("verticals") and clinical support services ("horizontals"). As can be seen in the example of FIG. 3, multiple clinical supports services work in conjunction with this single clinical program. In this particular example, each of the diagnostic clinical support service, ambulatory clinical support service, acute medical clinical support service, substance preparation clinical support service, and invasive clinical support service operate in conjunction with this one clinical program.

Once such an integration framework is defined, techniques can then be implemented within this framework to reduce waste and improve patient outcomes in patient care settings. For example, clinical content and ADW functionality can be integrated to provide the described healthcare delivery waste reduction tools.

Example Method

Figure 4:
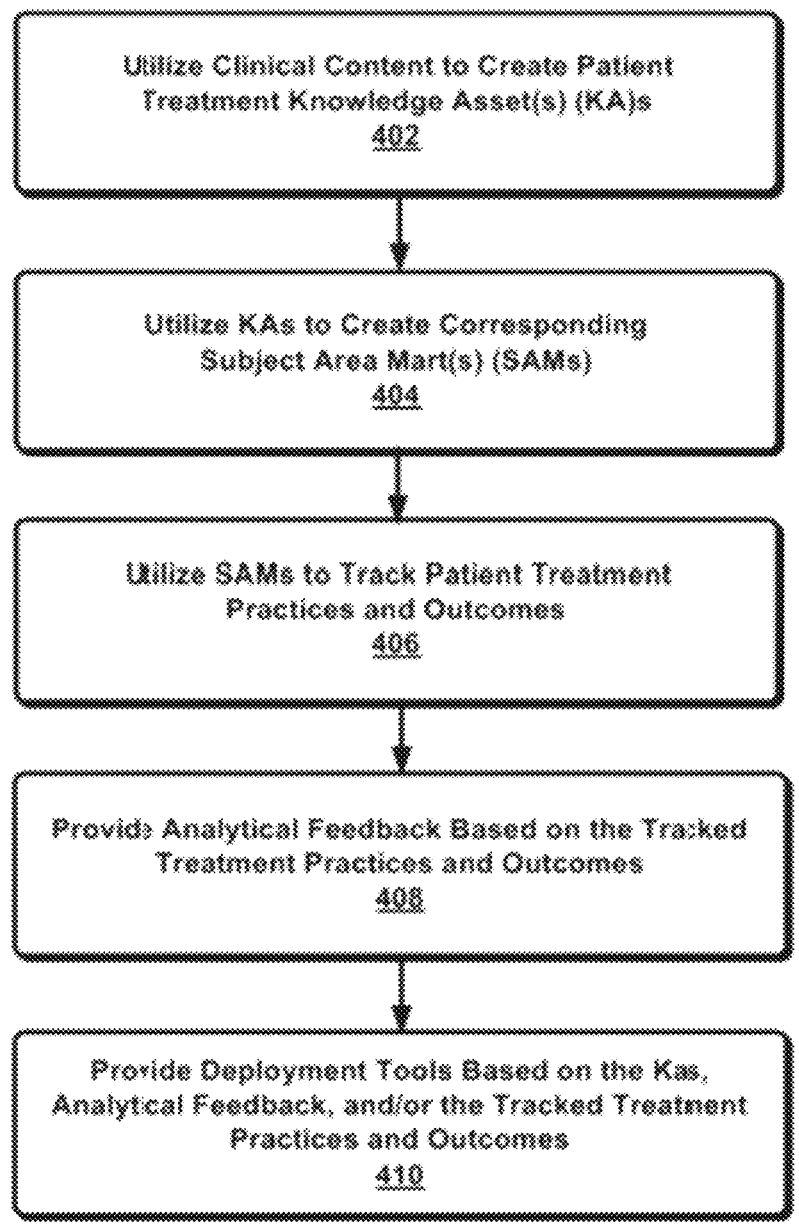

FIG. 4 illustrates an example flowchart of a technique or method 400 for reducing or eliminating wasteful treatment practices by integrating clinical content and ADW functionality, in accordance with at least one embodiment.

At Block 402, clinical content can be utilized to create one or more KAs that include patient treatment criteria. These treatment criteria can include, for example, criteria associated with the ordering of healthcare services (i.e., treatment ordering criteria), the delivery of healthcare services (i.e., delivery treatment criteria), and/or patient safety treatment criteria.

Furthermore, these treatment criteria can be measured and thus tracked as indicators via a PC S's ADW. As such, these indicators may be considered actionable and deployable with respect to tracking actual treatment practices and outcomes of the PCS to identify waste resulting from the ordering of treatment, delivery of the treatment, and/or patient complications from this treatment.

In other words, these treatment criteria can be used to track the PCS's ordering, delivery, and defect waste across the spectrum of the healthcare delivery framework, including its various clinical programs and clinical support services. For example, adherence to diagnostic criteria, patient triage criteria, and/or treatment algorithm criteria can be measured and determined at a very granular level (e.g., date/time, treatment setting, practitioner(s), patient, etc.).

In at least one embodiment, treatment ordering-related clinical content (e.g., commercial grade clinical knowledge from clinical literature, clinical effectiveness care algorithms, etc.) can be utilized to create care process KAs. More particularly, treatment ordering criteria may be discerned from clinical literature, such as peer-reviewed literature found in a medical journal for instance, to create care process KAs. Examples of treatment ordering criteria might include, without limitation, diagnostic criteria, patient triage criteria, medication order set criteria, treatment protocol criteria, and the like.

Figure 4A:
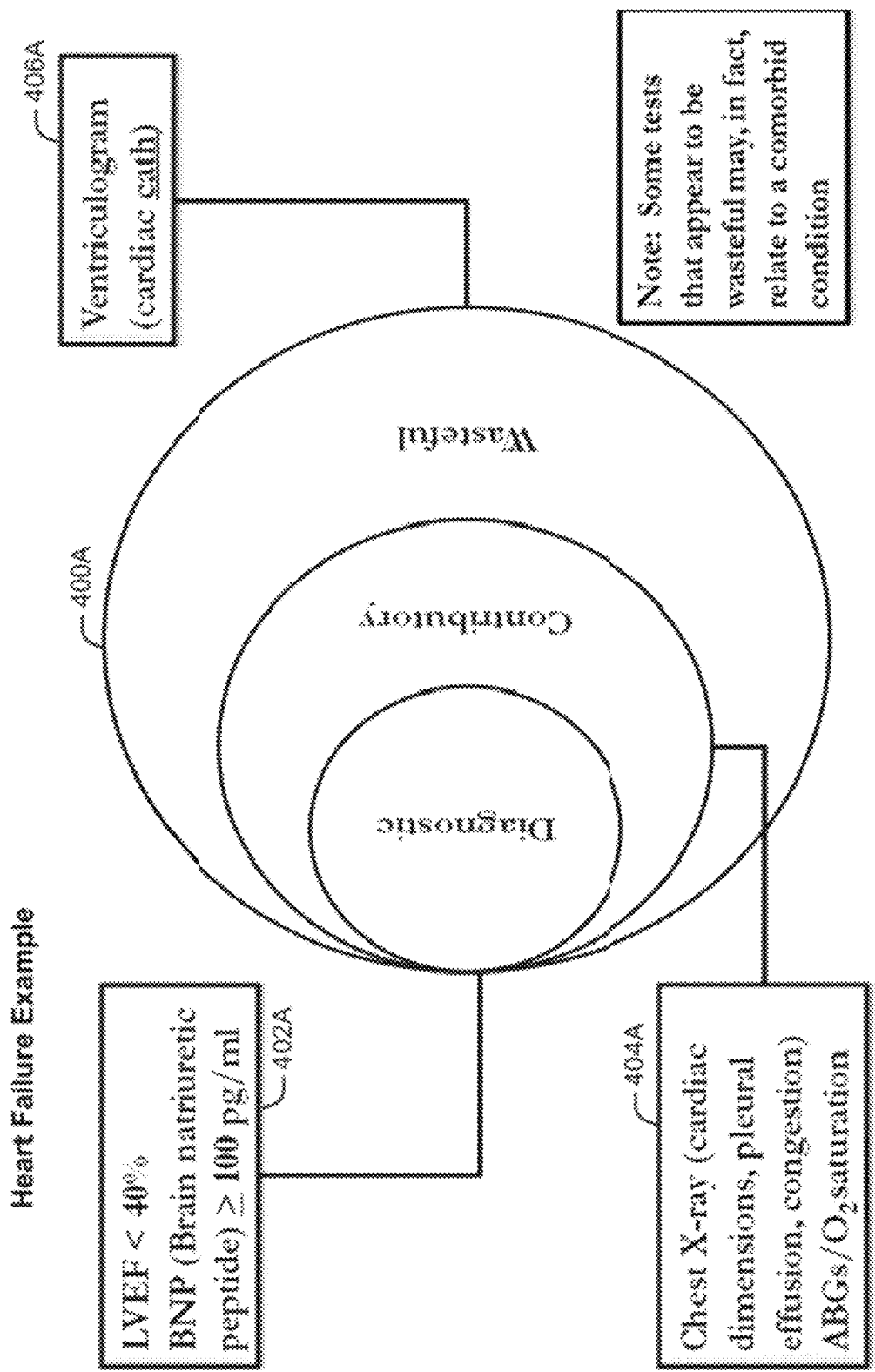

To facilitate the reader's understanding of how treatment ordering-related clinical content can provide treatment ordering criteria (that may identify ordering waste) for a care process KA, consider FIG. 4A. FIG. 4A includes a waste diagram 400A which depicts different types of example diagnostic treatment orders (402A, 404A, and 406A) associated with heart failure.

Assume here, in FIG. 4A, that the relationship between the waste diagram 400A and the example diagnosis treatment orders 402A, 404A, and 406A is based on current treatment ordering-related clinical content that may be used to discern treatment ordering criteria for each of the example diagnosis orders. As such, in accordance with the described techniques, treatment practices of a PCS associated with the ordering each of these diagnosis orders may be tracked.

Here, note that example diagnosis treatment orders 402A are considered diagnostic according to the current treatment ordering-related clinical content, and are thus not considered to be wasteful. Example diagnosis treatment orders 404A, in turn, are considered contributory and thus also not wasteful. Example diagnosis treatment orders 406A however, are considered wasteful (i.e., ordering waste) since they are not necessary for a diagnosis. As an example, a diagnosis treatment order can be considered wasteful even if it gives data that is necessary for diagnosis, if the diagnosis treatment order gives data duplicative of a second diagnosis treatment order and is more expensive that the second diagnosis treatment order.

Alternatively or additionally to care process KAs being created, treatment delivery-related clinical content can be utilized to create workflow KAs. More particularly, treatment delivery criteria associated with treatment workflow processes may be discerned from "lean" process information (e.g., value stream maps, etc) or other types of treatment workflow literature.

Consider, for example, value stream maps as an example of a type of treatment ordering-related clinical content. In the context of the integration framework described above, value stream maps can be applied to each clinical support service ("horizontal"), as listed in the examples provided in TABLE 5 for instance:

TABLE 5

Value Stream Map Examples
Workflow Clinical Content. Value stream maps apply
individual clinical support service units:

| Diagnostic | Acute Medical |
|---|---|
| Clinical Pathology | Emergency Care Unit |
| Anatomic Pathology | ICUs (ICU, CCU, NICU, PICU) |
| Diagnostic Radiology | Med-Surg Units |
| Substance Preparation | Invasive |
| Pharmacy | Hospital ORs |
| Blood Bank | Ambulatory Surgical Center |
| Ambulatory | Labor and Delivery |
| Primary Care Offices | Medical Interventional Units (e.g., |
| Chronic Disease Clinics | Cath Lab, Interventional Radiology, |
| Specialty Offices | Endo Lab) |

Figure 4B:
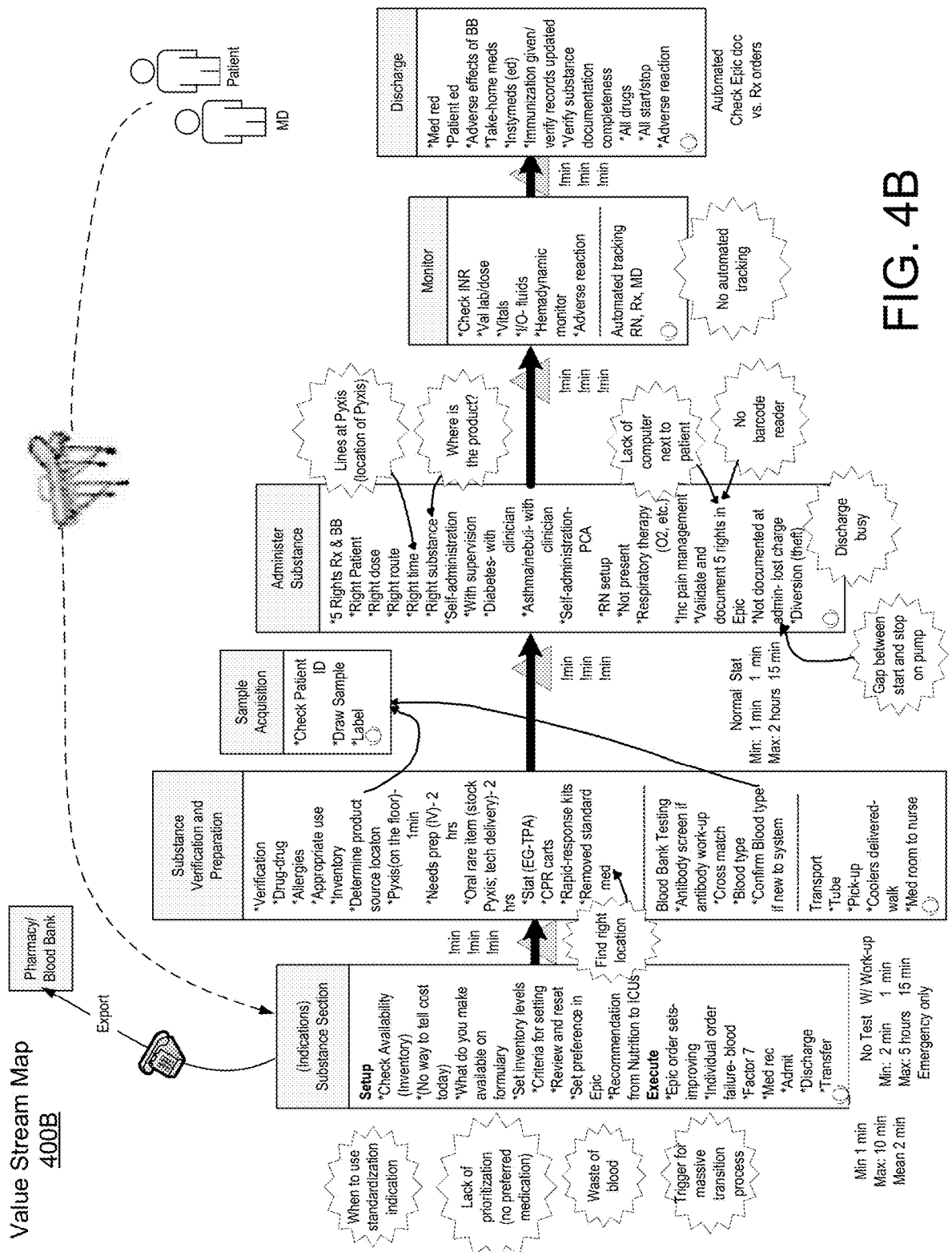

To facilitate the reader's understanding, an example value stream map 400B that is associated with a substance preparation clinical support service is illustrated in FIG. 4B.

Alternatively or additionally to care process KAs and workflow KAs being created, other types of KAs can be created as well. For example, both treatment ordering-related clinical content and treatment delivery-related clinical content can be utilized to create patient safety KAs. In this regard, patient safety criteria for such a KA may be discerned from both of these types of content. Patient safety criteria can be useful with respect to tracking defect waste which, as the example PCS clinical care unit defect waste distribution chart 400C of FIG. 4C illustrates, can be found in a variety of clinical care units. As can be seen in the example of 4C, many clinical care units operate within different clinical support services. In this particular example, in can be seen that medications can be administered in radiology, pediatric ambulatory css, adult ambulatory css, ecu, icu/ccu, med-surg, IP surg, ASC, and interventional medicine. Patient safety waste can be reduced by incorporating the same safety protocol for medication, no matter what clinical support service is involved.

In at least one embodiment, one or more of the KAs described above may be created as KA starter sets that have not been customized (i.e., refined, fingerprinted, and/or otherwise modified) for a particular PCS, and are thus not PCS-specific. These KA starter sets may then be provided to PCS subject matter experts (e.g., clinical practitioners, physicians, nurses, allied health practitioners, administrators, etc.) and/or others to customize and adapt them as PCS-specific KAs.

Figure 5:
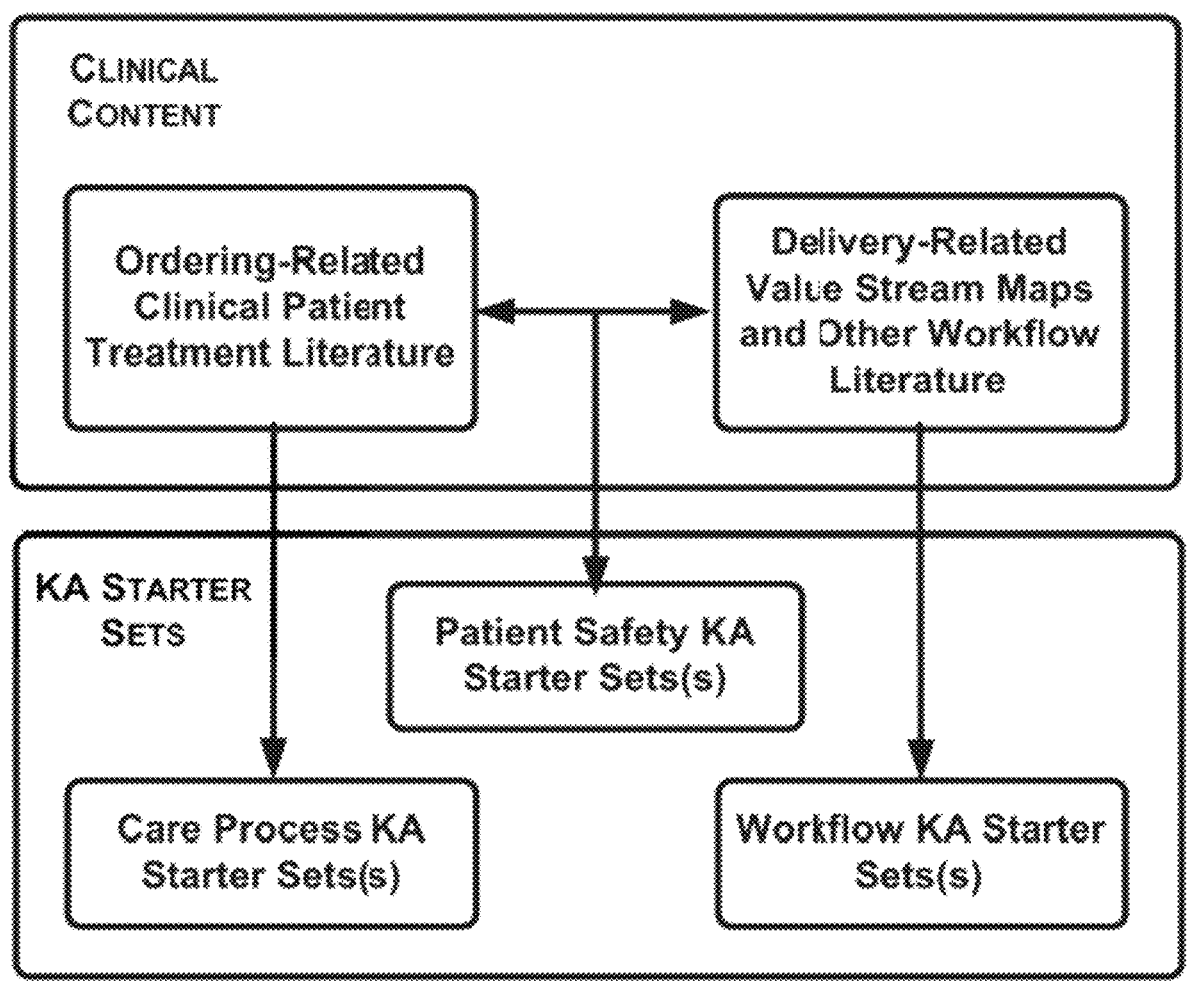
FIG. 5 illustrates an example starter set creation flow diagram, in accordance with at least one embodiment.

To facilitate the reader's understanding, FIG. 5 illustrates an example starter set creation flow diagram 500 for creating three types of treatment KA starter sets, namely: care process KA starter sets with treatment ordering criteria, work flow KA starter sets with treatment delivery criteria, and patient safety KA starter sets with patient safety treatment-related criteria.

In at least one embodiment, a knowledge information toolkit (KIT) may be utilized to create the KA starter sets. For example, the KIT can be used to automatically facilitate formatting the KA for one or more source marts of the PCS's ADW. As described below, these source marts can be configured to extract and provide data from one or more data sources. Alternatively or additionally, the KIT may be utilized by the subject matter experts and/or others of the PCS to customize individual KA starter sets.

Referring back to FIG. 4, At Block 404 KA(s) (e.g., KA starter sets and/or customized PCS-specific KAs) can be utilized to create subject area marts (SAM)s for the PCS's ADW. A SAM may be thought of as an ADW data construct that provides a relatively narrow and specific set of data (by virtue of data extraction routines) associated with one or more particular groups, or cohorts, of patients having a similar diagnosis. A SAM's data extraction routines can be based on certain treatment criteria selected from the KA(s) utilized to create that SAM. As discussed below, these data extraction routines allow the SAM's treatment criteria to be tracked as key indicators via the PC S's ADW.

As an example, TABLE 6 below provides a simple summary associated with tracking some key indicators associated with two example types of defect waste: bed sores and falls. Note that a pre-cohort and cohort are listed for each type of waste along with example interventions that might be implemented to reduce or eliminate these types of waste. As an example, a pre-cohort can be considered any possible patient that may potentially be a cohort.

TABLE 6

Example Patient Safety Analytics Development Process

| Pre-Cohort | Cohort | Intervention | Tracking System (e.g., key indicators) |
|---|---|---|---|
| Defined by Clinical Support Service Unit(s) | Patients at risk for harm/injury (may be defined by screening tool) | "Standard work" to be implemented to prevent injury | Analytic markers to track near misses and injuries |
| Pressure injury ("bed sores") example | | | |
| ICU Med-surg units | Braden Scale score ≤16 (or 14) | Special mattress Turn patient Skin precautions | ICD codes Procedures Consultation |
| Falls Example | | | |
| ICU Med-surg units | Strength, agility, cognition evaluation | Falls precautions protocol | Falls incidents |

Figure 6:
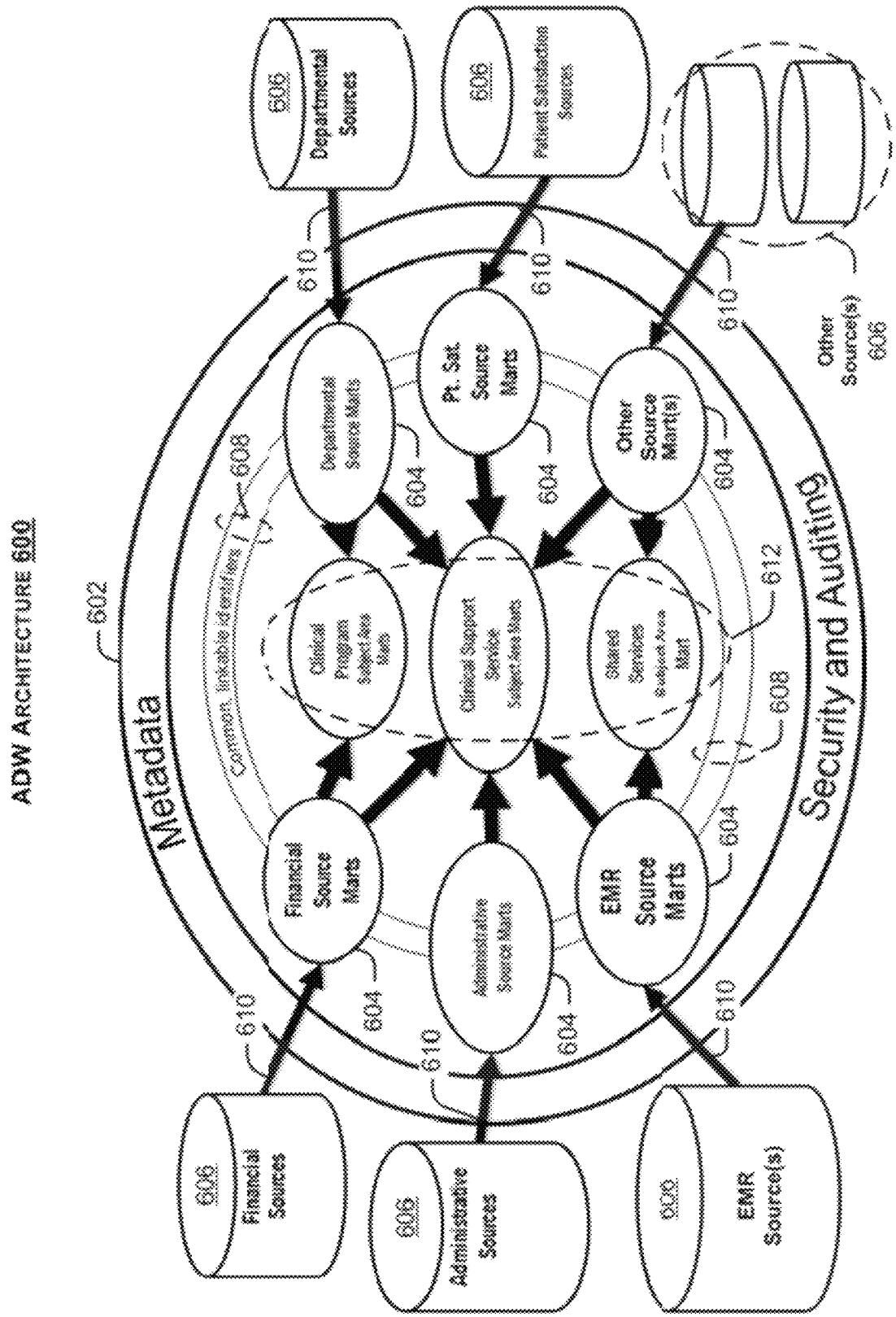
FIG. 6 illustrates a high level diagram of an example adaptive data warehouse architecture that may be utilized to implement the described techniques, in accordance with at least one embodiment.

To facilitate the reader's understanding of how SAMs can facilitate treatment criteria to be tracked as key indicators in an ADW, FIG. 6 illustrates a high level diagram of an example ADW architecture 600 that may be utilized to implement the described techniques, in accordance with at least one embodiment. Note that in this example, ADW 602 includes various types of source marts 604 that can be configured to obtain data from various corresponding data sources 606 that are associated generally with a PCS's operations, and, in some examples, more specifically with the PCS's delivery of healthcare to patients.

For discussion purposes, a source mart may be thought of as an ADW data construct that, in at least one embodiment, can be linked to other source marts by one or more common linkable identifiers. In this example, each of the source marts types 604 is thus shown as being linked by one or more of a set of common linkable identifiers 608. In one example, the set of common linkable identifiers can comprise creating a common linkable identifier to signify a particular patient. For example, a single patient may have a different identifier in different data sources. Therefore, a common linkable identifier can be created so that each patient has a single unique identifier that can be linked back to the multiple identifiers in the data sources. In a typical embodiment two CLIs are defined: one identifying a particular patient and one identifying a particular provider. Thus each destination table that includes a column identifying a patient or a provider is also augmented with an additional column containing the CLI for that patient or provider. Each source mart can be configured to provide a relatively broad set of data associated with its corresponding data source by virtue of one or more data extraction routines.

Here, the various data sources 606 include financial, administrative, electronic medical record (EMR), departmental, and patient satisfaction sources. Additionally, data sources 606 can also include other suitable sources of data associated with the PCS's operations that, for the sake of brevity, are not shown in this example. Each of the source mart types is thus labeled according to its corresponding data source (e.g., "EMR Source Marts").

In one example, the other suitable sources of data can include data that a care provider may want to include in any analysis, but is not available in any of the data sources 606, such as for example, in the EMR. In some examples, an application may be used to transfer data that is not in one of the data sources 606 to the ADW.

One particular example of such an application is IDEA. IDEA is a web based application that allows the definition of a schema (called an application) and provides editing interfaces to capture data relative to that application. A database job then transforms the data from IDEA format into the ADW so that it can be used by reporting tools. For example, IDEA moves the capturing or modifying of data out of application, such as, for example, Excel or Access, and into a location connected to the ADW.

Note that as indicated by transformation arrows 610, data from each of the individual data sources 606 can be transformed into more specific data related to one or more corresponding individual source marts by virtue of the corresponding source mart'(s) data extraction routines. Transformed data of the source marts can be linked via the common linkable identifiers 608 of the ADW.

In this example, the ADW 602 also includes a set of SAMs 612. For illustrative and discussion purposes, note that the SAMs 612 are shown generally categorized as types of services associated with the PCS's treatment delivery, namely: clinical program SAM(s), clinical support SAM(s), and shared services SAM(s).

For discussion purposes, a SAM may be thought of as an ADW construct associated with a cohort that, compared to a source mart for instance, is configured to provide a relatively narrow and specific set of data relevant to that cohort. Each SAM can be configured to provide its set of data by virtue of one or more data extraction routines.

Note that in this example, each of the source marts 604 can be linked to one or more of the SAMs 612 such that each source mart's data can be transformed into even more specific data for that SAM(s), as shown by transformation arrows 610.

In operation, a SAM's data extraction routines can be based on the SAM's treatment criteria. As explained above, in at least one embodiment, the SAM's treatment criteria can include treatment ordering criteria, delivery treatment criteria, and/or patient safety treatment criteria selected from one or more KAs utilized to create the SAM. Since these treatment criteria can be tracked as key indicators via the ADW 602, the PCS's treatment practices and outcomes can be tracked.

For example, adherence to diagnostic criteria, patient triage criteria, and/or treatment algorithm criteria can be tracked and measured at a very granular level. This allows for analytical feedback to be prepared that can identify, at a very granular level, ordering, delivery, and defect waste associated with these practices.

Referring back to Block 404 of FIG. 4, similar to KAs, in at least one embodiment, one or more of the SAMs may be created as SAM starter sets that have not been customized for the PCS, and are thus not PCS-specific. These starter sets may then be provided to PCS subject matter experts and/or others to customize and adapt them as PCS-specific SAMs.

Figure 7:
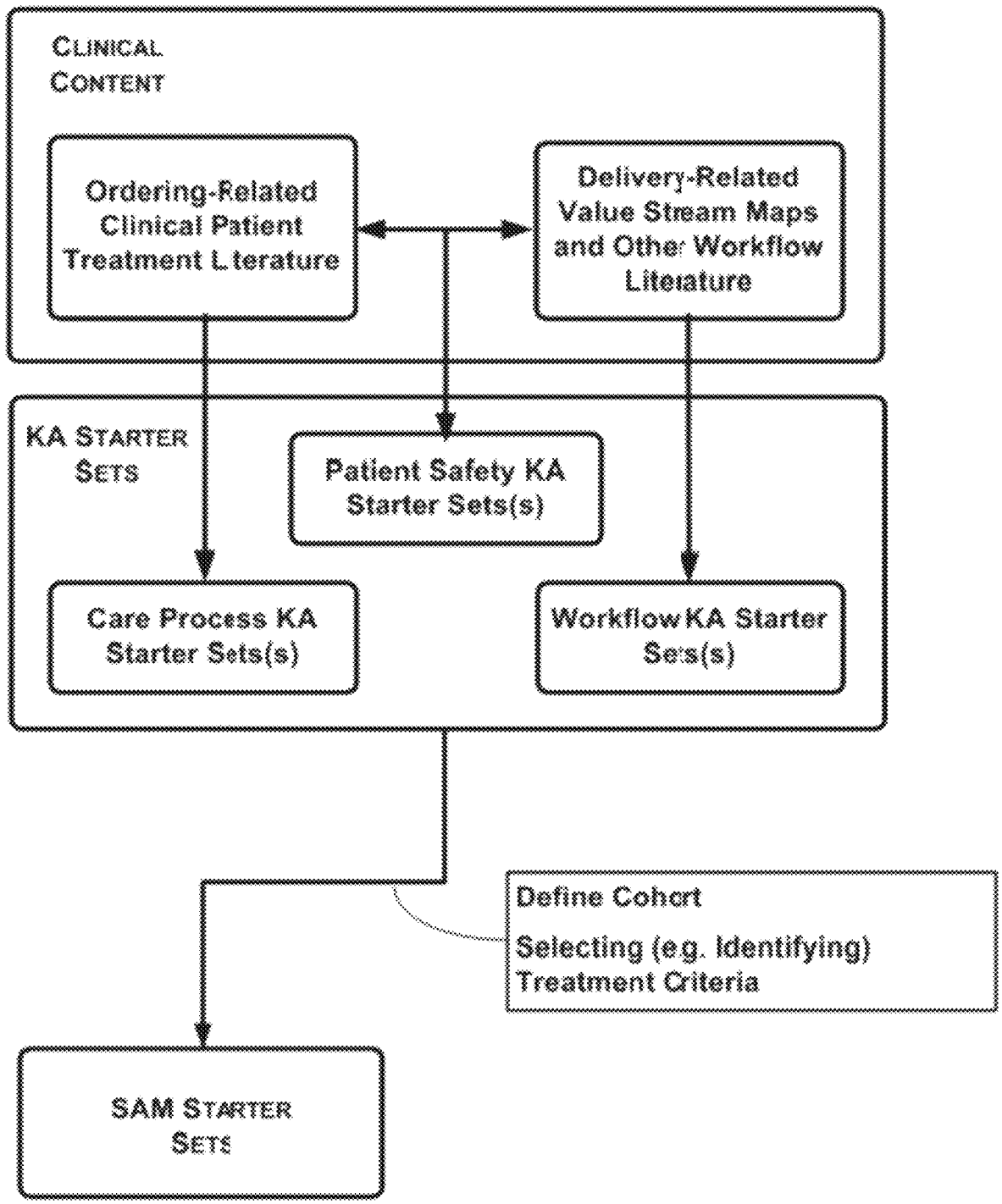
FIG. 7 illustrates an example of a SAM starter set creation flow diagram, in accordance with at least one embodiment.

To facilitate the reader's understanding, FIG. 7 illustrates an example starter set creation flow diagram 700 for creating SAM starter sets from KA starter sets. Note that FIG. 7 is presented in the context of the starter set flow diagram 500, and thus includes the "Clinical Content" and "KA starter sets" boxes from FIG. 5. Also note that the process of creating SAM starter sets includes defining cohorts and selecting (e.g., identifying) treatment criteria.

In at least one embodiment, the KIT described above may also be utilized to create SAMs, including SAM starter sets. For example, the KIT can be used to identify or define the cohort for a SAM starter set and to select criteria from a KA(s) to be tracked. Alternatively or additionally, the KIT may be utilized by PCS subject matter experts and/or others to customize individual SAMs, such as individual SAM starter sets for instance.

Figure 19:
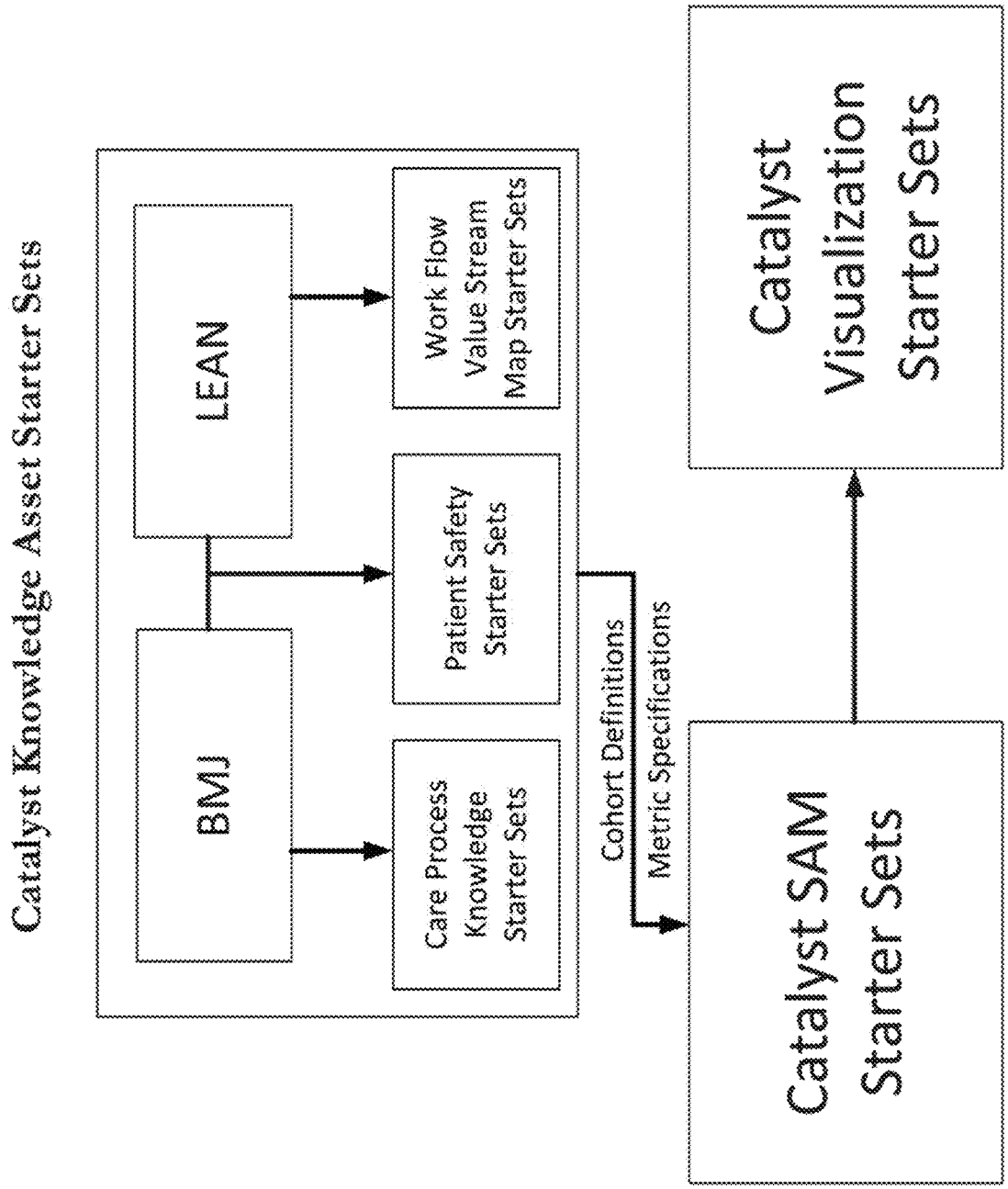
FIG. 19 illustrates an example of various starter sets that can be created according to at least one embodiment.

FIG. 19 illustrates another example of the creation of a SAM starter set. As FIG. 19 demonstrates, and as briefly described above, the creation of a SAM comprises at least the determination of a cohort and metric specifications. Furthermore, SAMs are created with the knowledge obtained during the creation of the KA starter sets.

As shown in FIG. 19, different types of clinical knowledge and/or research are used in the creation of the KA starter sets. For example, clinical research, such as, for example, the use of a medical journal, or even the specific know-how of a doctor or group of doctors, can be used for care process knowledge asset start sets. As another example, work flow value stream maps (which can be created by a third party, a particular doctor, or even a hospital in which the systems and methods of the present invention are employed) can be used to create the workflow knowledge assets starter sets. As yet another example, a combination of the clinical research/content and value stream maps can be used to create the patient safety data sets.

Upon creation of the knowledge assets, SAMs can be created. Initially, a cohort is defined. A cohort can be thought of as a group that shares common characteristics. For example, in a situation where a hospital is trying to eliminate waste in asthma patients, the cohort can be considered to be asthma patients.

However, it is not always easy to determine who an asthma patient is. For example, is it only those patients that are diagnosed with having asthma? Does it include patients who take medication given only to those with asthma, but haven't been formally diagnosed with asthma? Does it include patients with asthma like symptoms but don't take any asthma medication and haven't been formally diagnosed with asthma? As can be seen, defining a cohort can be fraught with many difficulties.

Therefore, the step of defining a cohort can include defining a pre-cohort. A pre-cohort can be considered anyone that may be classified in the definition of the cohort. For example, in the asthma example above, a pre-cohort can be considered anyone who has been diagnosed with asthma, who takes asthma medication, has asthmas symptoms, etc. This definition can be used initially to ensure that the cohort definition doesn't potentially leave out any person or group of people that should be considered part of the cohort population.

Next, a set of metrics is defined. This allows the creation of tables that can be used for visualizations. The visualizations (or even summary tables by themselves) can be used to determine if the particular metrics need to be redefined. This allows for a process that can be changed and adjusted to find the best results.

Referring back to FIG. 4, once SAMs (e.g., SAM starter set(s) and/or PCS-specific SAM(s)) have been created, at Block 406 the SAMs can be utilized to track patient treatment practices and outcomes of the PCS. More particularly, the treatment criteria in the SAMs can be utilized to track the PCS's patient treatment practices and outcomes. As noted above, in operation this can be accomplished by tracking the criteria as key indicators via the PCS's ADW.

As a simple practical example of tracking, consider a cohort of asthmatic patients. A SAM for this cohort might have treatment criteria for how to diagnose a patient presenting in an emergency room with acute asthma-like symptoms (e.g., shortness of breath, chest tightness, etc.). Assume that current clinical literature includes findings for treating asthma in general.

Included in these findings are specific findings related to diagnostic treatment for patients presenting with acute asthma-like symptoms. Assume that these specific findings indicate that unless the patient presents with certain specified conditions, initially ordering a chest x-ray is unnecessary (and thus wasteful) as a diagnostic treatment. Instead, a more effective and efficient initial diagnostic treatment is found to be (among other things) starting the patient on a certain medication and observing their response for a period of time. Based on the patient's response, decision can then be made by the treating clinician on whether or not to initiate more invasive therapy.

In accordance with the described techniques, criteria associated with the various treatment findings and recommendations for treating asthma may be discerned from the literature and included in a corresponding KA (as a KA starter set and/or as a PCS-specific KA). Furthermore, that KA (and potentially one or more other KAs) can be utilized to create a corresponding SAM that is specific for patients presenting with acute asthma-like symptoms.

As described above, part of the process of creating the SAM can include formatting the SAM for the PCS's ADW and selecting treatment criteria from the KA that are specific to this cohort, and that can be tracked via the PCS's ADW as key indicators. These key indicators might represent, for example, one or more criteria for conditions when an initial chest x-ray is warranted and one or more other criteria for conditions when an x-ray is unnecessary. As a result, individual treatment practices of the PCS can be tracked with respect to whether or not they adhere to these criteria.

Figure 34:
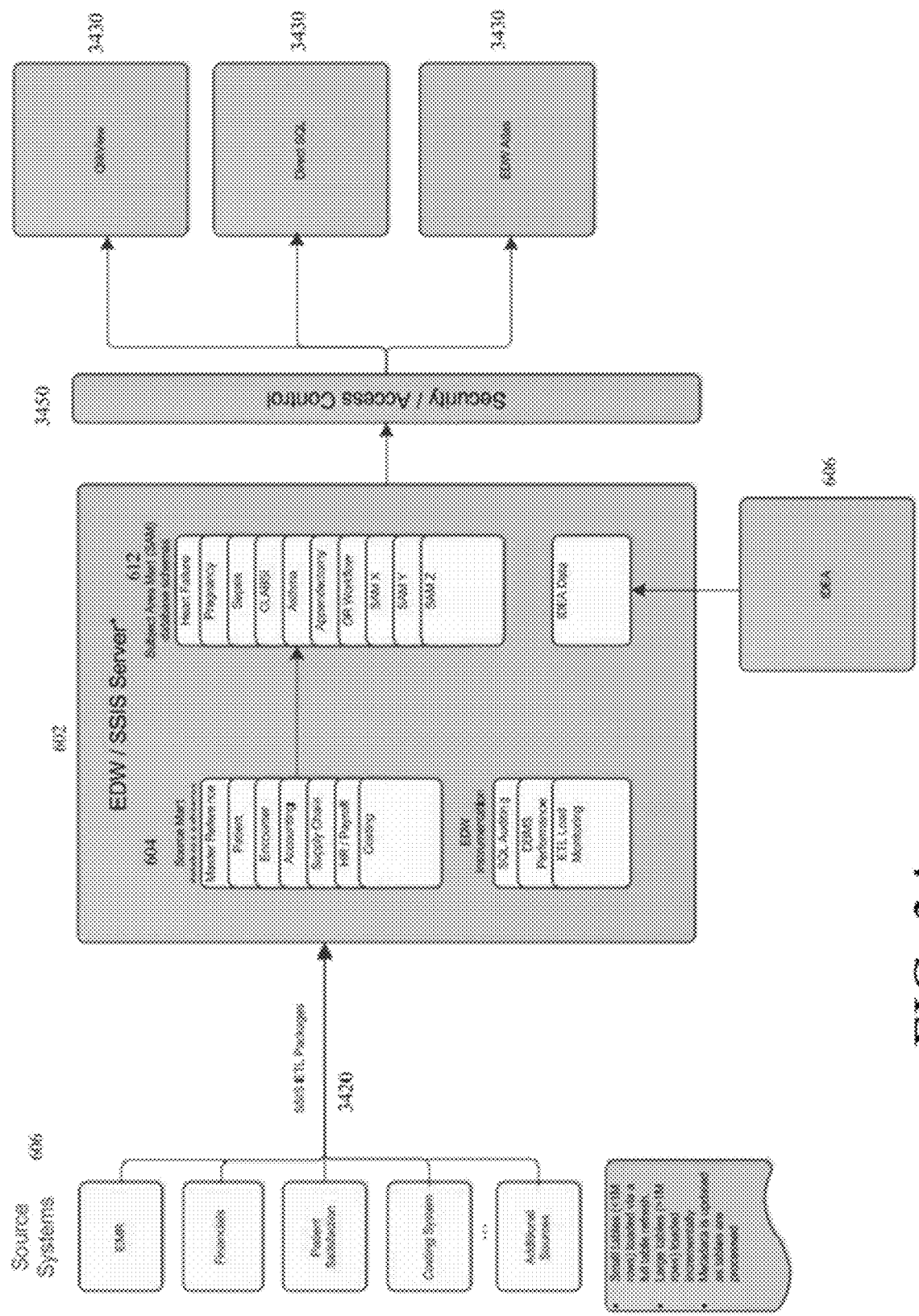
FIG. 34 illustrates portions of the ADW architecture of FIG. 6 according to at least one embodiment.

FIG. 34 illustrates another view of the example of the ADW architecture 600 of FIG. 6. FIG. 34 can be used to see the overall architecture flow of the ADW 600. It should also be noted that the example of flow illustrated in FIG. 34 can be used with data warehouses different than depicted in the example of FIG. 6.

With continued reference to the example of FIG. 34, ADW 602 comprises various types of source marts 604 that can be configured to obtain data from various corresponding data sources 606 that are associated generally with a PCS's operations, and, in some examples, more specifically with the PCS's delivery of healthcare to patients.

Also, as seen in the example of FIG. 34, the source marts 604 are used in the SAMs 612. In some examples, ADW 602 can comprise program modules for one or more functions. In different embodiments, the program modules and support data can be distributed over one or more computer systems. Note that as used herein, the term "program module" does not necessarily imply unity of structure. For example, two or more program modules, when considered together, still constitute a "program module" as that term is used herein. Also, a "database" is considered herein to include one or more tables. That is, a single table is considered herein to be a special case of a "database".

As can be seen in FIG. 34, data is driven into the ADW from source systems 606. Examples of the source systems can include, for example, EMR, Financials, Patient Satisfaction, Costing System, and similar other data sources. Other data sources not specifically mentioned herein may also be included.

The data from the source systems 606 is drawn into the source marts 604. SSIS ETL Packages 3420 can be used to draw the data from the source systems 606 into the source marts 604. In one exemplary embodiment, the program modules for accomplishing this task are written for Microsoft® SQL Server Integrations Services (SSIS), and the modules themselves are known as "ETL packages", or merely "packages". However, other embodiments can use other program environments for implementing modules. Examples of source marts 604 can include, matter reference, patient, encounter, accounting, supply chain, HR/payroll, costing, etc. In such embodiments, the ADW may contain many source mart packages, each roughly corresponding to one of the destination tables in the source marts 604. This can allow for finer granularity pipelining. Some packages may load more than one destination table. SSIS ETL Packages 3420 are discussed in greater detail below with respect to FIG. 21.

In some examples the packages only draw the data from source systems 606 that is required by the source marts 604. It is possible that some of the source marts 604 may draw from the same source systems. For example, more than one source mart 604 may receive data from EMR sources. In addition, in some examples, some source marts receive data from more than one source systems 606. It should be noted that any of the source marts 604 can draw from any of the source systems 606.

In some embodiments, the data from the source systems 606 is loaded into another location, before being loaded into the source marts 604. For example, data from the EMR source system can be loaded into a separate database. One or more separate source marts 604 then can draw data from the separate database.

The data in the source marts 604 then can be used in the SAMs 612. Similar to the source marts 604 drawing in the data it needs from the source systems 606, the SAMs draw in the data from the source marts 604 that they need. In some instances, the data is manipulated before arriving in a SAM. For example, the data in a source mart table can undergo calculations. In other instances, there may be no need for the data to be manipulated before arriving in a SAM, and as such, the data is merely transferred to a SAM table. Examples of SAMs 612 can include heart failure, pregnancy, sepsis, CLABSI, asthma, appendectomy, OR workflow, and the like.

Similar to the source marts 604 using the packages 3420, the SAMs 612 can use SAM ETL packages (not shown) to draw the data (and manipulate the data if necessary) to the SAMs tables. In such embodiments, the ADW may contain many SAM packages, each roughly corresponding to one of the destination tables in the SAMs 612. In some embodiments, the ADW may contain only a single SAM package, which can be used to populate each of the SAMs tables.

Also, as seen in FIG. 34, and as previously mentioned, data can also be drawn into ADW 602 via other sources. One such example is via IDEA. In the example of FIG. 34, the data from IDEA goes into an IDEA data table. This table can be used similarly to the data from a SAMs table. In other examples, it may be possible to include data from IDEA into a source mart 602 and/or a SAM 612.

Figure 35:
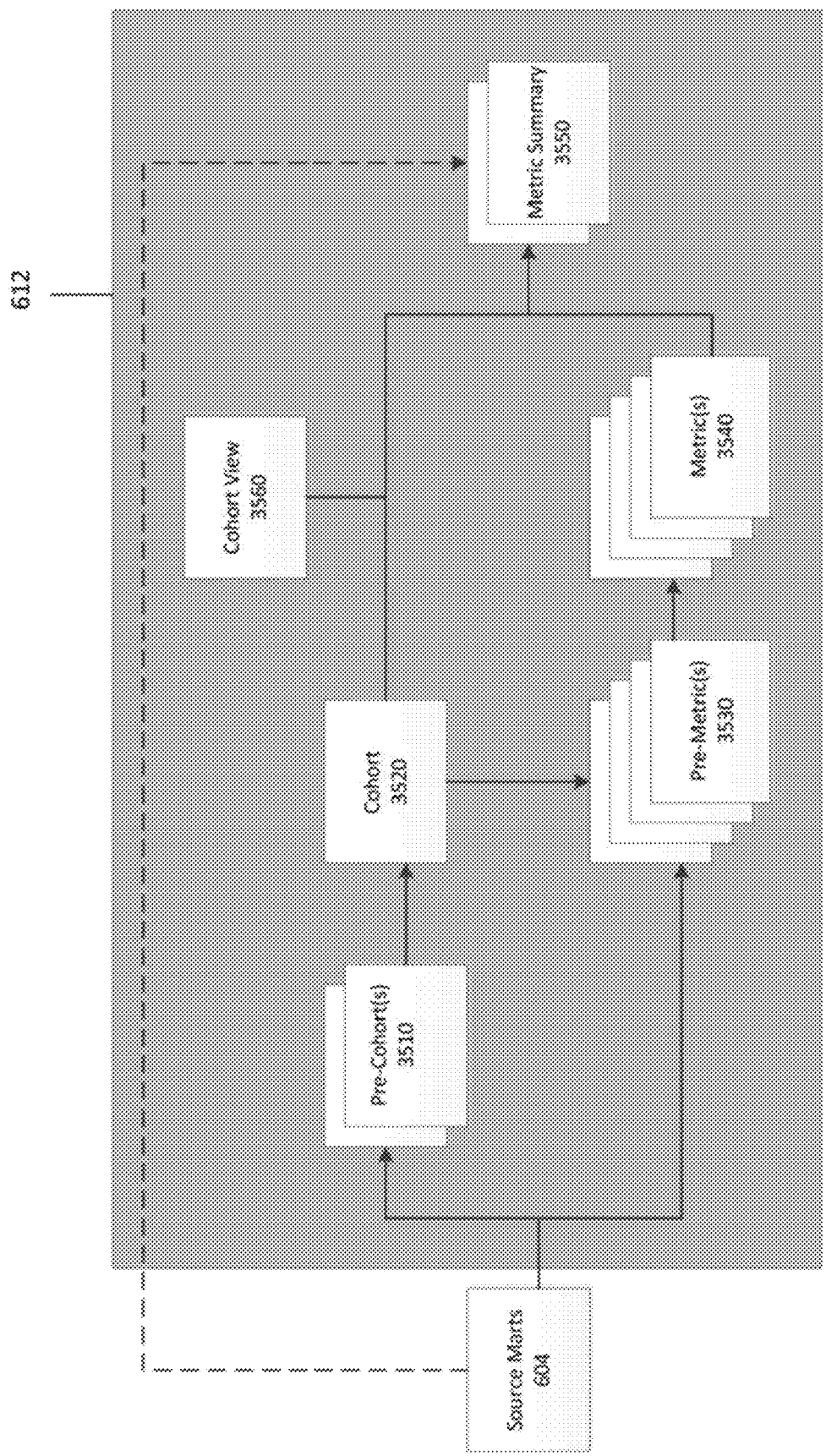
FIG. 35 illustrates an example of a SAM according to at least one embodiment.

FIG. 35 illustrates an example of a SAM 612 according to one or more embodiments of the present invention. As can be seen in FIG. 35, a SAM can contain multiple tables. Examples of the SAMs tables can include a pre-cohort table 3510, a cohort table 3520, a pre-metric table 3530, a metric table 3540, and a metric summary table 3550. In addition, other tables, such as, for example, a cohort view table 3560, can also be included in a SAM 612.

As previously mentioned, a pre-cohort is used to define any event (e.g., patient) that may be classified within a certain group (cohort). In some examples, there may be more that one pre-cohort table for any SAM 612. In such examples, there may be a first pre-cohort table for a user defined pre-cohort, and there may be a second pre-cohort table for an uncustomized pre-cohort. For example, the uncustomized pre-cohort table can be created using established medical knowledge and research and/or experience from the table's creator. The pre-cohort table can have many different columns, for example, a patient ID, a hospital bill ID, EMR encounter ID, and medical record number (MRN). Other examples of columns in the pre-cohort table can include event date, event type, event sub type, event value, etc.

The cohort, as mentioned above, is the group of events (patients) that fall within the defined criteria to qualify within a particular group. Examples of columns for a cohort table 3520 can include patient ID, a hospital bill ID, EMR encounter ID, and medical record number (MRN). In addition, other examples of columns in the pre-cohort table can include rule start date, rule end date, rule name, etc.

A metric is used to define a particular item that a user would like to analyze. For example, a metric can include the re-admittance rate of patients that visited a hospital for asthma. A pre-metric table 3530 is used to determine which information from the source marts 604 is needed to determine such a re-admittance rate. Therefore, a pre-metric table is filled with information that is pulled from the source marts 604. Examples of this type of information can include patient ID, hospital ID, EMR encounter ID, MRN, etc. Furthermore, the pre-metric table will include information specific to each metric, such as for example, ICD9 code, ICD9 descriptions, etc.

The metric table 3540, uses the information in the pre-metric table and calculates any necessary values that are needed for the metric. For example, the metric may be the turnover time for an operating room. The metric table will include this value. This value will be calculated using the information supplied in the pre-metric table. For example, the pre-metric table may have a two separate times, a beginning time and an end time. These two times can be used to calculate the turnover time for the operating room. Examples of information included in a cohort table 3520 can include patient ID, hospital ID, EMR encounter ID, MRN, etc. Furthermore, the metric table can include information specific to the given metric.

A SAM can also include more than one pre-metric table 3530 and metric table 3540. This is because each metric defined by the user will have its own separate pre-metric table and metric table. Therefore, if there are 10 metrics defined, then there will be 10 metric tables and 10 pre-metric tables. It should be noted that it is also possible to have more or less pre-metric and metric tables than the number of metrics, including one pre-metric and metric table for each SAM.

The metric summary table 3550 uses the information contained in the metric tables 3540 and the cohort table 3520 to create a summary table. Therefore, the table will include each of the cohorts and the information pertaining to each of the metrics for that cohort.

In addition, the SAM 612 can include a cohort view table 3560. This allows a user to determine all of the patients that fall within the cohort definition, without having to view all of the analytics that will be present in the metric summary table 3550.

Figure 36:
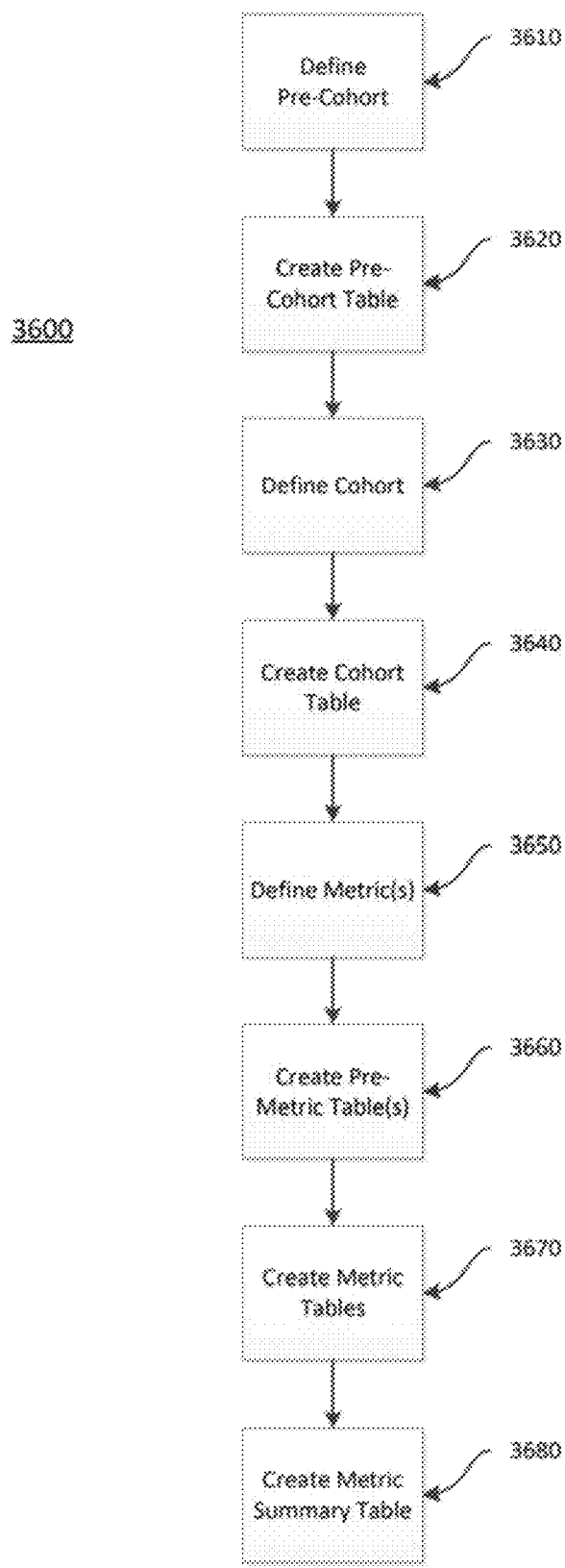
FIG. 36 illustrates an example of a method of creating a SAM according to at least one embodiment.

FIG. 36 is a flow chart illustrating an example of a method of creating a SAM 3600 according to one or more embodiments of the present invention. The SAM of method 3600 can be the same as or similar to SAM 612. As with all flowcharts herein, it will be appreciated that many of the steps can be combined, performed in parallel or performed in a different sequence without affecting the functions achieved. In some cases, as the reader will appreciate, a re-arrangement of steps will achieve the same results only if certain other changes are made as well. In other cases, as the reader will appreciate, a re-arrangement of steps will achieve the same results only if certain conditions are satisfied. Furthermore, it will be appreciated that the flow charts herein show only steps that are pertinent to an understanding of the invention, and it will be understood that numerous additional steps for accomplishing other functions can be performed before, after and between those shown.

With continuing reference to FIG. 36, method 3600 includes a step 3610 of defining a pre-cohort. As discussed above, a pre-cohort is defined as any event that may be included within a cohort. Having a defined pre-cohort allows for easier amendments to the SAM. For example, if the definition for a cohort is changed, data doesn't need to be pulled from a source mart, but can be pulled from the pre-cohort table instead.

In some embodiments, there may be more than one definition of the pre-cohort. As an example, a user may define a pre-cohort one way. In addition, there may be another definition of the pre-cohort according to established medical literature. In some examples, the pre-cohort established from medical literature can be altered to create the pre-cohort defined by the user.

In step 3620, the pre-cohort table is created. The table is populated with data from each event at the hospital (or facility that is using the ADW) that qualifies as a pre-cohort.

As an example, the pre-cohort table can include patient ID, Hospital Bill ID, EMR Encounter ID, MRN, Event Date, Event Type, Event Sub Type, Event Value, and the like. The pre-cohort table can be the same as or similar to pre-cohort table 3510.

The data for the pre-cohort table is delivered to the table from one or more source marts 604. The data is delivered to the pre-cohort table via the SAM Package. The SAM package is discussed in greater detail below and an example is shown in the flow chart represented in FIG. 37.

In Step 3630, the cohort is defined. The cohort is a group of patients that share an event. The user can identify the rule or rules that qualify the members of the pre-cohort class as a cohort. It should also be noted that a patient may be listed more than once in both the pre-cohort and cohort tables. This is because a patient may have more than one qualifying event that places them into the pre-cohort and/or cohort class.

Step 3640 of method 3600 in FIG. 36 is creating the cohort table. In some examples, creating the cohort table comprises filtering the data in the pre-cohort table to only include those events that qualify under the cohort rules. In the same or other examples, it may be necessary to pull more data from one or more source marts to fill the table with data. In the same or other examples, it may be necessary to perform calculations on the data already existing in the pre-cohort table to fill the cohort table. Examples of data in the cohort table can include Patient ID, Hospital Bill ID, EMR Encounter ID, MRN, Rule Start Date, Rule End Date, Rule Name, and the like. The cohort table can be the same as or similar to cohort table 3520.

The data for the cohort table is delivered to the cohort table via the SAM Package. The SAM package is discussed in greater detail below and an example is shown in the flow chart represented in FIG. 37.

Next, step 3650 is defining the metrics for the SAM. The metrics are indicators that a user wants to look at to analyze the operation of the hospital or other institution which is being evaluated. In many cases, the metrics that are being looked at can be defined using medical research tools. In the same or other examples, the metrics are defined through experience of the user and/or other entities. In the same or other examples, the metrics may be defined by trial and error. It should be noted that any number of metrics can be used and any number of ways to define the metrics can be used.

After the metrics are defined, step 3660 is creating pre-metric tables. A pre-metric table is a table that includes all the necessary data as defined by the metric. However, there is no manipulation (e.g., calculations) done to that data. For example, if the metric is the turnover time for an operating room, the pre-metric table may include the end time for one operation and the start time for the next procedure. However, there is no calculation to determine the time between these two events. In some embodiments, there is a separate pre-metric table for each metric that is defined in step 3650. Examples of data included in the pre-metric tables can include Patient ID, Hospital Bill ID, EMR Encounter Number, MRN, ICD9 Codes, ICD9 Descriptions, and the like. The pre-metric tables can be the same as or similar to pre-metric tables 3530.

The data for the pre-metric tables is delivered to the pre-metric tables via the SAM Package. The data can include data from one or more source marts 604 and/or the cohort table 3520. The SAM package is discussed in greater detail below and an example is shown in the flow chart represented in FIG. 37.

Next, step 3670 is creating the metric tables. The metric tables are the final manipulated table for each individual metric. Therefore, each metric has its separate table. The metric tables take the data from the pre-metric table and perform any necessary manipulations/calculations to the data to determine the value(s) for the defined metric. For example, in the example of the operating room turnover time, the metric table will have a value for the turnover time as calculated from the two times (end time of one procedure and the start time of the next procedure). Examples of the data in the metric tables include Patient ID, Hospital Bill ID, EMR Encounter Number, MRN, Data Specific to the Particular Metric, and the like. The metric tables can be the same as or similar to metric tables 3540.

The data for the metric tables is delivered to the metric tables via the SAM Package. The data includes data that is present in the pre-metric tables, which in many cases has to be manipulated/calculated before being entered into the metrics table. The SAM package is discussed in greater detail below and an example is shown in the flow chart represented in FIG. 37.

Step 3680 of method 3600 is creating a metric summary table. The metric summary table is a table that lists all of the cohorts and metrics for any given SAM. In many examples, the metric summary table is a table that joins all of the metric tables with the cohort table, to deliver a single table with all of the data present for the SAM. In the same or other examples, it is possible to have more than one metric summary table if the user wants to analyze the data in the SAM at more than one granularity level. Examples of data in the metric summary table can include Patient ID, Hospital Bill ID, EMR Encounter ID, MRN, Demographics, Rule Indicators (such as rule names, dates, etc.), Stratification (such as department, medical group, etc.), Metrics, etc. The metric summary table can be the same as or similar to metric summary table 3550.

The data for the metric summary table is delivered to the metric summary table via the SAM Package. The data includes data that is present in the metric tables and cohort table. The SAM package is discussed in greater detail below and an example is shown in the flow chart represented in FIG. 37.

It should be noted that method 3600 can also include steps that aren't specifically mentioned in FIG. 36. For example, method 3600 can include creating a cohort view. This allows a user to view each of the cohorts in the SAM, along with other pertinent information related to that particular cohort. In some examples, if an individual is listed more than once in the cohort table, he or she will appear only once in the cohort view. The user can use the cohort view to look at the cohorts without all the necessary data pulls and calculations in the metric tables and metric summary tables.

In addition, method 3600 can include creating a visualization of the metric summary table(s). Although the tables can be viewed by themselves, in many instances, it is desirable for a user to view the data from the metric summary table in other forms, such as, for examples, graphs, charts, and the like.

Also, it should be noted that changes can be made to some of the tables without having an effect on other tables. For instance, a user can change the rules for a cohort, but that change will not have an effect on the pre-cohort table or any of the metric and pre-metric tables. Similarly, a user can change which metrics should be analyzed without changing the pre-cohort or cohort tables.

Furthermore, the ability to create a SAM in such a modular fashion, such as, for example, creating many different tables that are used to create a metric summary table, allows for a dynamic process.

Figure 37:
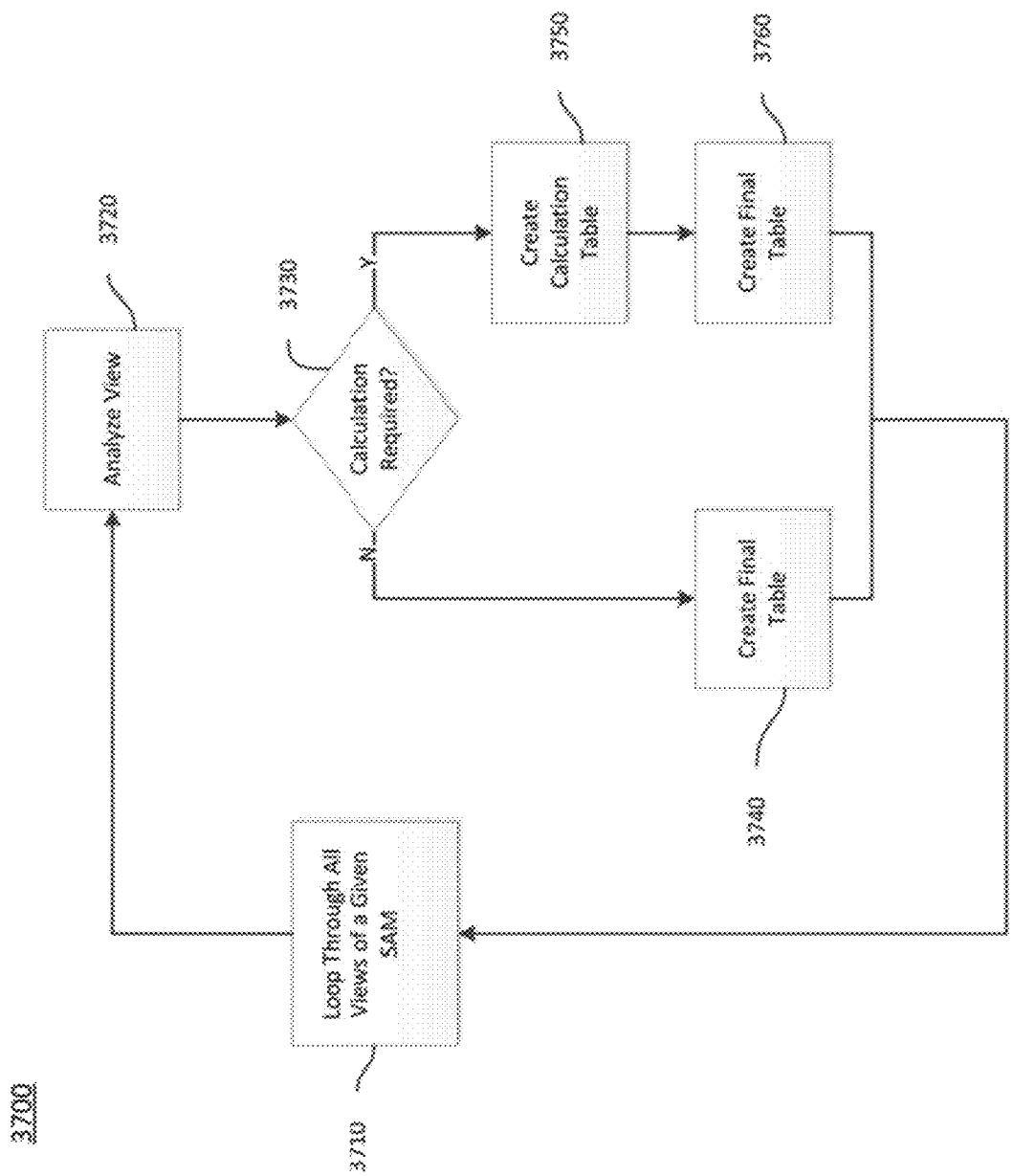
FIG. 37 illustrates an example of a flowchart for a SAM package according to at least one embodiment.

FIG. 37 shows an illustration of an example of a flowchart for a SAM package. As mentioned above, the SAM package is responsible for gathering data from source marts and/or other tables to create new tables. In some examples, it may be necessary for the SAM package to perform calculations or manipulate the data in some way to create the tables. In some embodiments of the present invention, it is necessary to only have one SAM package for all the SAMs and their respective tables.

Step 3710 of method 3700 is looping through all the views for a given SAM. Views can be considered the same as or similar to the tables throughout the disclosure. For example, the pre-cohort table 3510, the cohort table 3520, the pre-metric table 3530, the metric table 3540, and the metric summary table 3550 can all be considered views.

Step 3710 is performed in a sequential fashion. Therefore, each of the views or tables is looked at one at a time. In some examples, there is an order that must be followed when sequentially looking at the views. In such examples, an administration table may be used to determine which view is to be looked at. For example, data for the pre-cohort table must be filled before data for the cohort table.

In some examples, the administration table can also be used for rules for each view. For example, the rules can include whether the data can be brought in from a source mart. This may not be possible because the source mart has not been updated and cannot be used to bring in data at the current moment. In addition, it may have an order for which source marts must be drawn from before other source marts.

Step 3720 is analyzing a particular view. For example, each of the particular views (pre-cohort table, cohort table, pre-metric table, etc.) will be analyzed. In such a step, package 3700 will follow the guidance as illustrated in the administration table.

Method 3700 continues with step 3730, where it is determined whether calculations are needed to complete the tables. For example, if it is necessary to manipulate the data as it exists in the source mart and/or table from which you are bringing the data, the answer is yes. As such, the next step would be 3750. If however, there are no calculations necessary, the next step would be step 3740. In some examples, the administration table has a value indicating whether a particular table needs a calculation or calculations performed or not.

Step 3740 is creating a final table. This step is performed if there is no need to manipulate or calculate the data. The table can be created just by bring in values from another table in the ADW, whether from source marts, or other tables in the SAM. In some examples, the package 3700 will wipe any data already existing in the final table and wipe it clean. Then the package will look at a SQL statement pertaining to that particular table and run it. Once the SQL statement has been run, the table has been created.

Step 3750 is creating a calculation table for a particular final table. Step 3750 is run if there are calculations necessary for the final table. During step 3750 data is brought into the calculation table from other tables, whether from source marts and/or other tables in the SAM. The data that is brought in is the data necessary to calculate values for the final table and data that will directly populate the final table. Such a procedure allows a modular approach to creating a final table. This allows for a dynamic creation of the final table, and makes for a more streamlined method of creating a final table.

Once step 3750 has been accomplished, step 3760 is creating a final table from the calculation table. The final table is created using data from the calculation table. Some of the date from the calculation table can be transferred to the final table without any necessary calculation and/or manipulations. Other data may have to be manipulated or there may have to be calculations performed to determine the values for the final table. Similar to step 3740, the package will look at the SQL statement for the table and run it, thus creating the tables of steps 3750 and 3760.

After the completion of step 3760 or 3740 the package will move on to the next table to be created. If the administration table says that the next table is ready to be created, the package will determine whether a calculation is necessary (as often is stated in the administration table) to create the next table. The package will read the appropriate SQL statement and the process will repeat itself again, until a table is not ready to be created.

In some embodiments the SQL statement for each of the tables to be created can be located in the administration table, thereby allowing the package to look in at one primary location to complete its tasks. In other embodiments, the SQL statements are not located in the administration table.

The SAM package can communicate with the source systems by mechanisms appropriate to the particular source system. For example, the program modules may communicate using the source system's API, or by SQL-over-IP, or by some other protocol. Typically the communication will occur over a network such as 1706.

After completion of method 3700, data existing in one of the SAMs tables can be used in a number of ways. With reference back to FIG. 34, this can be seen as an output 3430 in FIG. 34. Outputs 3430 can include, for example, using the data in reporting software. One such example is Qlik-View™. In addition, other applications can also be used to access the SAMs data. For example, an application that accesses the metadata available in the ADW, including the SAMs. One such example is ATLAS. In other examples, the output 3430 can include a direct SQL statement.

In addition, ADW 602 can include security/access control 3450. Security/access control can allow the administrators of the ADW 602 control who has access to the data and system. Security/access control 3450 can be configured in a variety of ways. For example, in one setup, access can be restricted to certain individuals, groups of individuals, etc. In another example, access to the data can be open to most individuals; however, the system monitors and records everyone who accesses the data, and what data is accessed. In other examples, a hybrid approach can be used in which access is only given to certain individuals, and that access is monitored.

Referring again back to FIG. 4, at Block 408 analytical feedback can be provided (e.g., prepared, shared, and/or utilized) based on the tracked patient treatment practices and outcomes. This feedback can identify, for example, specific treatment practices related to the ordering of treatment, delivery of the treatment, and/or patient complications that are wasteful.

Figure 18:
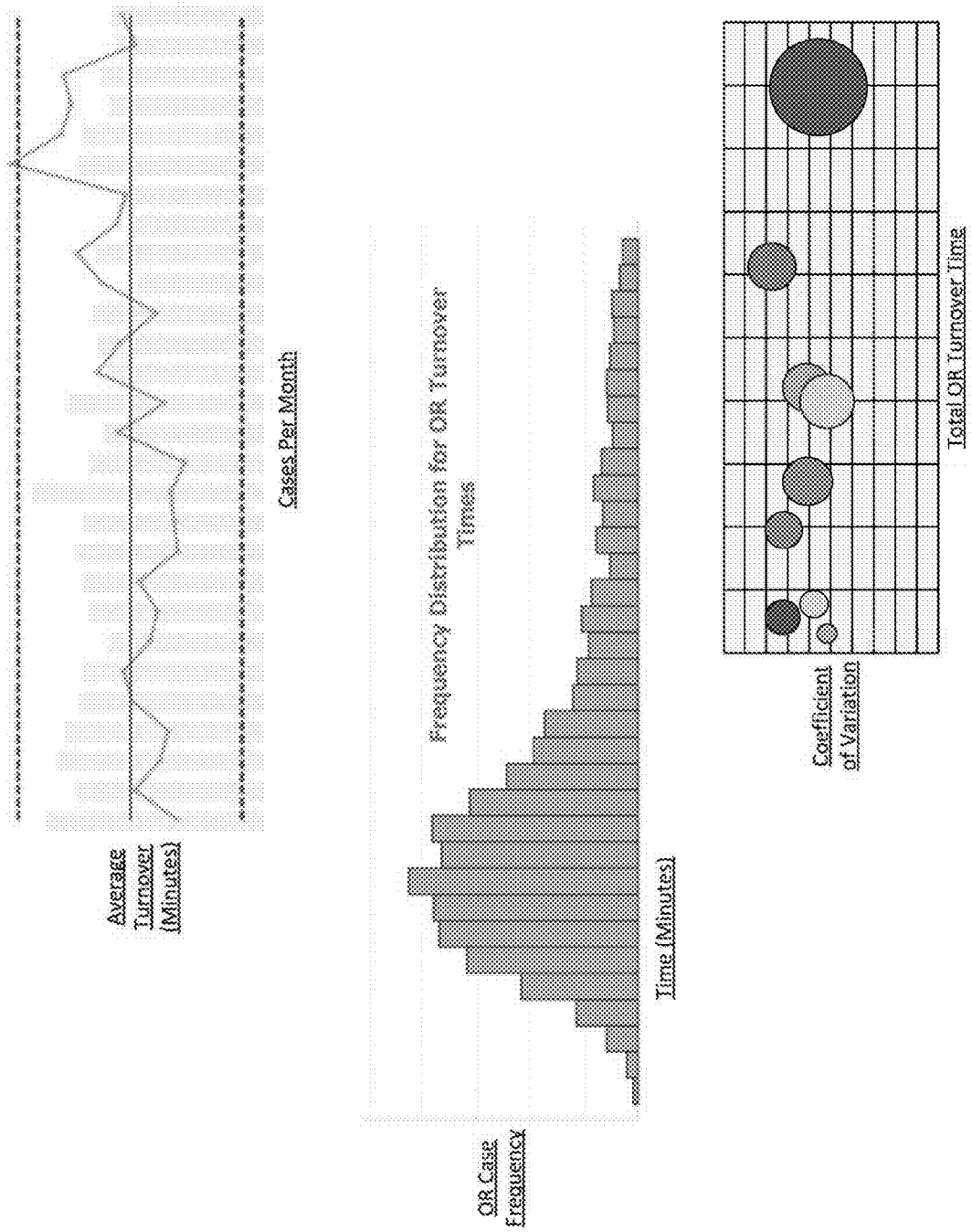
FIG. 18 illustrates examples of analytical feedback, in accordance with at least one embodiment.

The analytical feedback can be prepared in any suitable way. For example, in one embodiment, one or more charts, table, and the like can be created and presented. FIG. 18 illustrates examples of different types of analytical feedback that can be presented. The examples of FIG. 18 illustrate operating room turnover rates analyzed by different factors.

In at least one embodiment for instance, a KPA can be performed utilizing the tracked patient treatment practices and outcomes to identify the PCS's treatment practices and processes that are associated with a minimal amount of waste and with improved patient outcomes. In the same or other embodiments, KPA can be performed to determine those PCS's treatment practices and processes that are associated with a larger amount of waste. In such an embodiment the KPA can be used to determine the processes and/or practices that need improvement and, therefore, there would be a bigger benefit for the care facility to focus on improving such processes and/or practices.

Analytical feedback visualizations can then be prepared based on the analysis. For example, analytical feedback visualizations such as reports, dynamic dashboards, charts and other types of analytical representations can be produced and utilized (e.g., by the PCS and/or others) to assess whether or not the tracked treatment practices adhere to the treatment criteria and/or the identified treatment practices and processes associated with a minimal amount of waste and improved outcomes. This assessment can be performed down to a very granular level (e.g., date/time, treatment setting, practitioner(s), patient, etc.).

Figure 9:
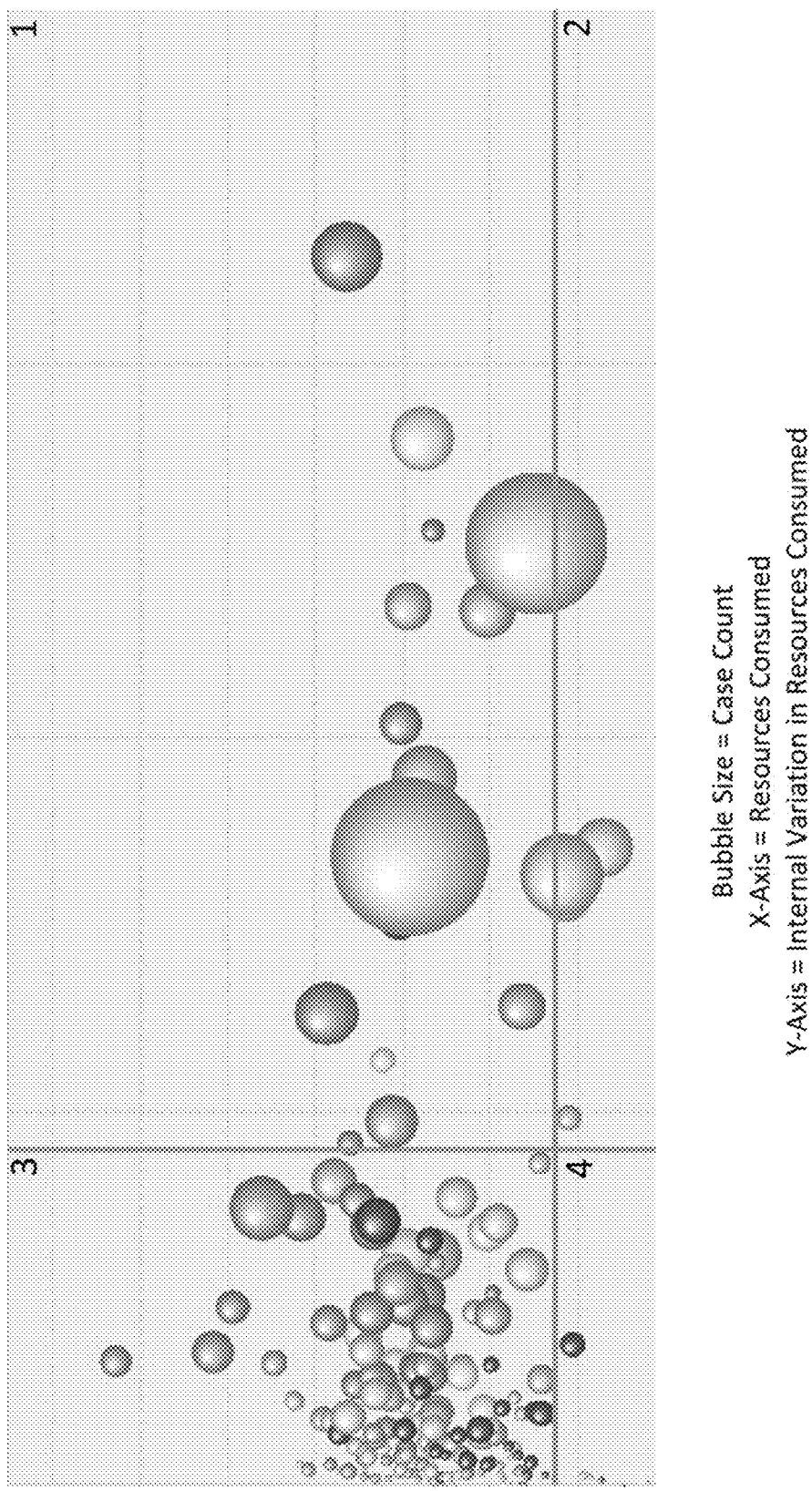
Figure 10:
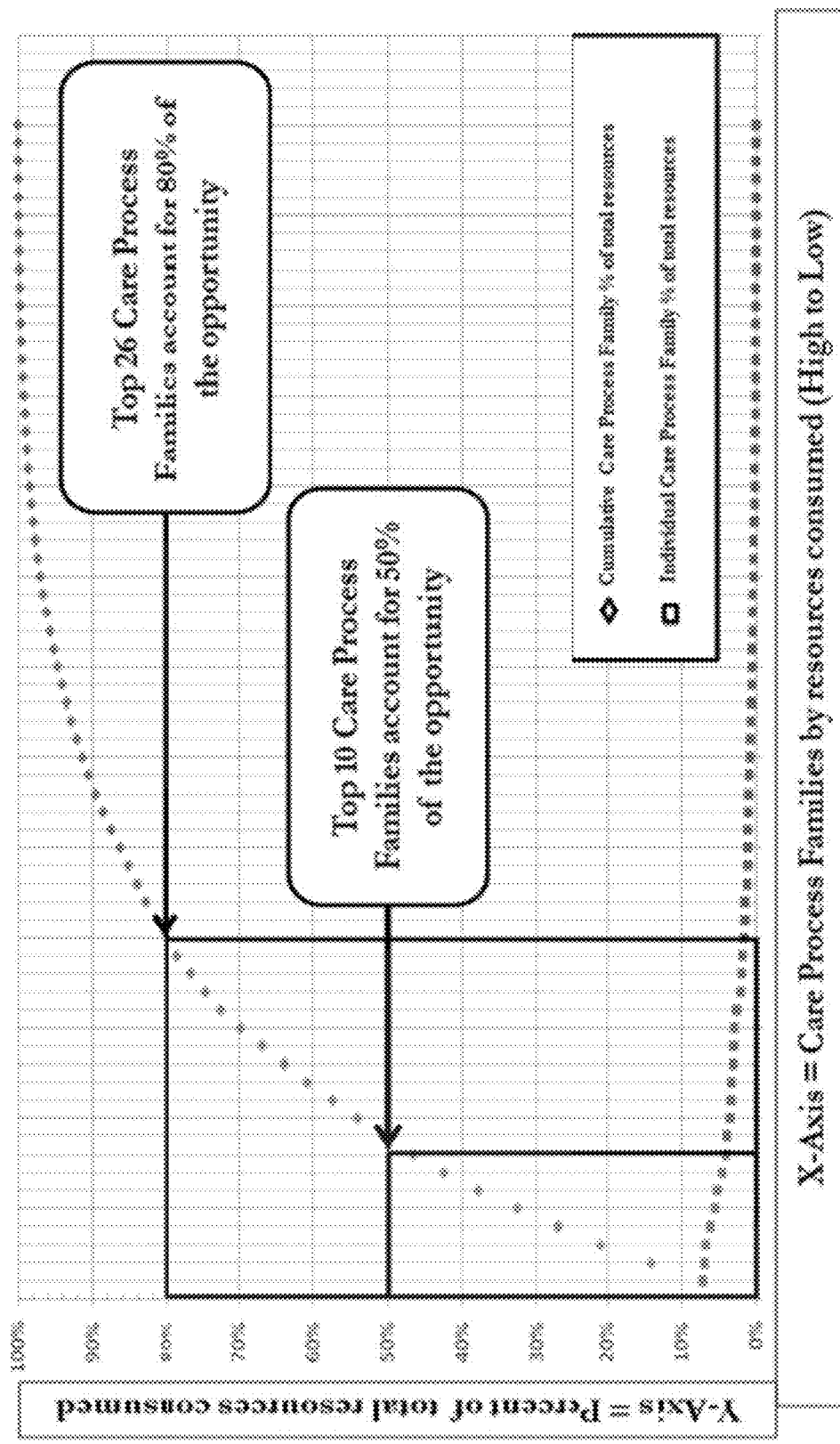

As a practical example, consider FIGS. 8-12 which illustrate example analytical feedback visualizations that might be prepared by performing a KPA based on a PCS's tracked patient treatment practices and outcomes. Note that the visualization illustrated in FIG. 9 is presented in black and white. In at least some embodiments however, the visualization may be presented in color such that the clinical domain of each individual bubble can be represented, and thus easily discerned, by that bubble's corresponding color. Alternatively or additionally, one or more other types of techniques may be utilized to represent each individual bubble's corresponding clinical domain.

Figure 11:
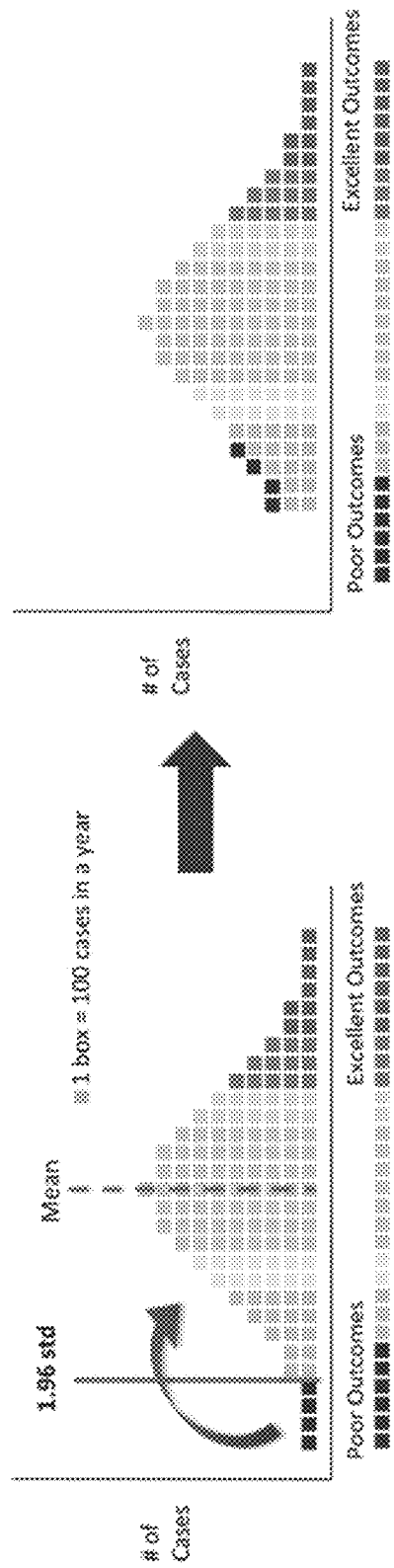
Figure 12:
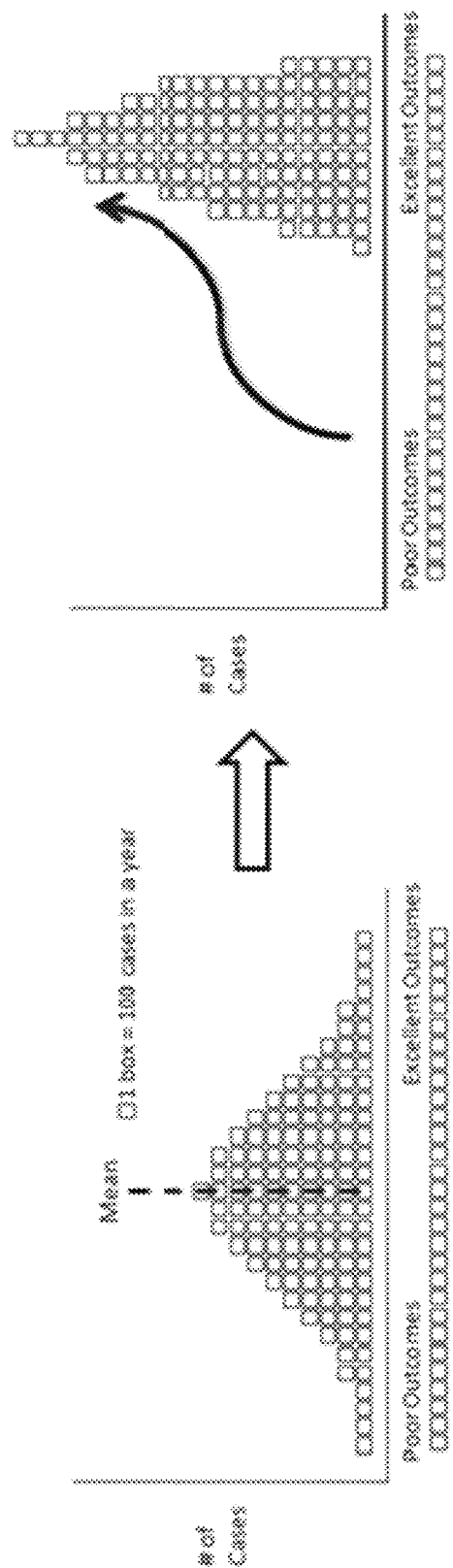

Similarly, note that while the visualizations illustrated in FIGS. 11 and 12 are presented in black and white, in at least some embodiments these visualizations may be presented in color such that each of the individual boxes representing cases corresponds to a color that further illustrates its relationship to adjacent boxes.

In at least one embodiment, analytical feedback visualizations can be created as visualization starter sets that have not been customized for the PCS, and are thus not PCS-specific. These starter sets may then be provided to PCS subject matter experts and/or others to customize and adapt them as PCS-specific visualizations.

FIG. 19 illustrates an example of various starter sets that can be created during method 400. 1910 illustrates the creation of KA starter sets, such as for example, care process KA starter sets, work flow value stream map starter sets, and patient safety starter sets. Each of these starter sets can be created with the use of clinical knowledge, as previously discussed.

With continuing reference to the example of FIG. 19, the knowledge asset (KA) starter sets can then be used to create SAM starter sets as seen in 1920. The KA starter sets, in conjunction with the cohort definitions and metric specifications, can be used to create the SAM starter sets.

Finally, the example of FIG. 19 shows the creation of visualization starter sets using the SAM starter sets at 1930. The visualization starter sets turn data that has been collected and/or analyzed into the visualizations.

Referring back to FIG. 4 once again, to facilitate the PCS adopting and/or customizing (i.e., fingerprinting) the KAs, SAMs, and analytical feedback, and in implementing treatment changes to reduce identified waste, at Block 410 deployment tools can be provided. These deployment tools may be based on the KAs, analytical feedback, and/or tracked treatment practices. Furthermore, these tools can include deployment visualizations, consultative services, recommendations, and or supportive tools to facilitate the PCS implementing changes that will result in wasteful patient treatment practices (i.e., waste) identified in the analytical feedback being reduced or eliminated.

Figure 13:
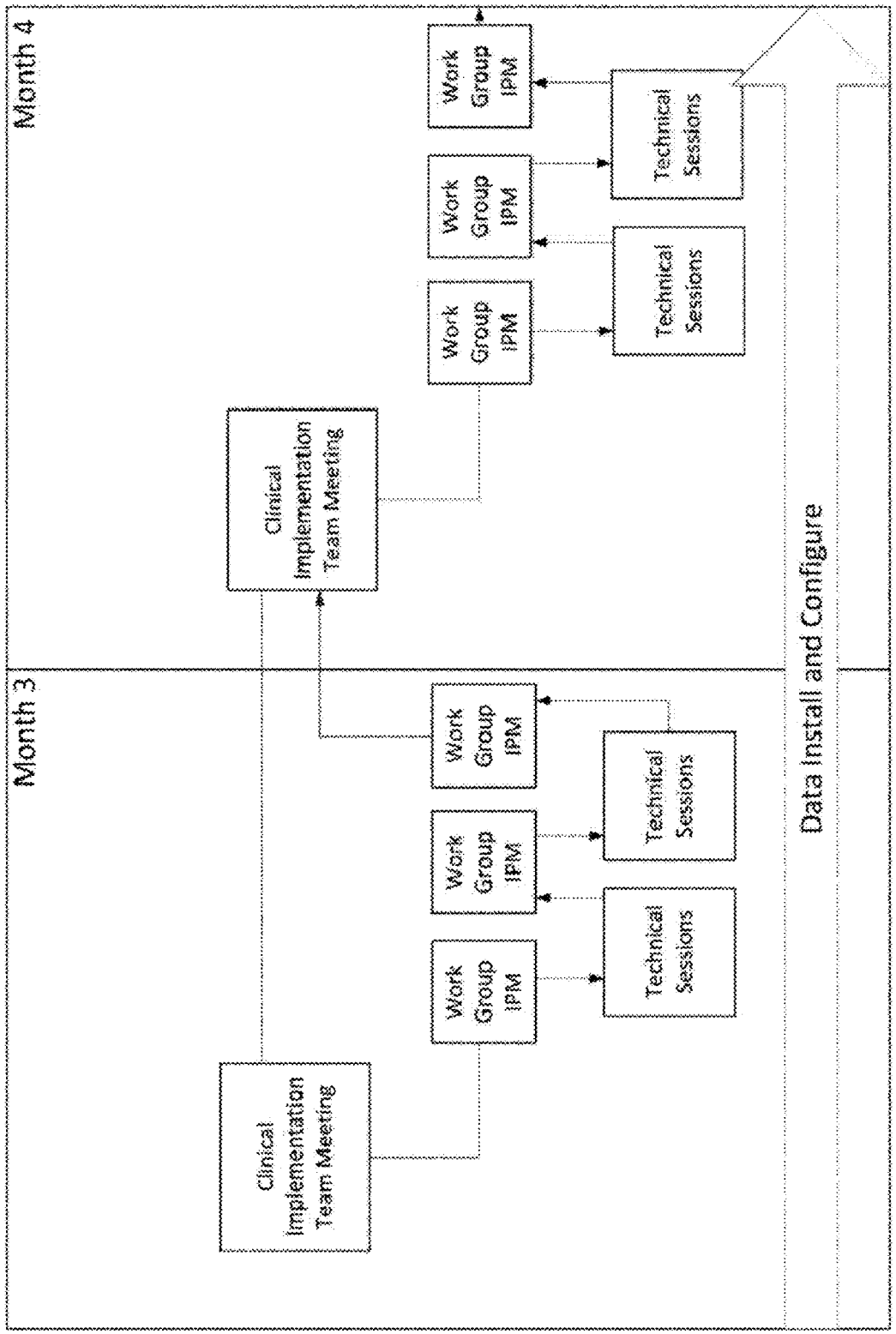
FIG. 13 illustrates an example deployment team flow process, in accordance with at least one embodiment.

As but one example, deployment tools might include deployment visualizations (e.g., organizational charts, value stream maps, flow charts etc.), consultative services, and/or recommendations. These tools can assist the PCS in organizing its treatment providers and other staff into sequential hierarchical deployment teams, as represented in FIG. 13—which illustrates an example deployment team flow process.

In practice, deployment teams can be ideally suited to fingerprint KA treatment criteria of the KAs (e.g., to front-line clinicians) and analytical feedback, and to implement changes on an ongoing basis that will result in reducing or eliminating identified wasteful patient treatment practices (i.e., waste).

Figure 14:
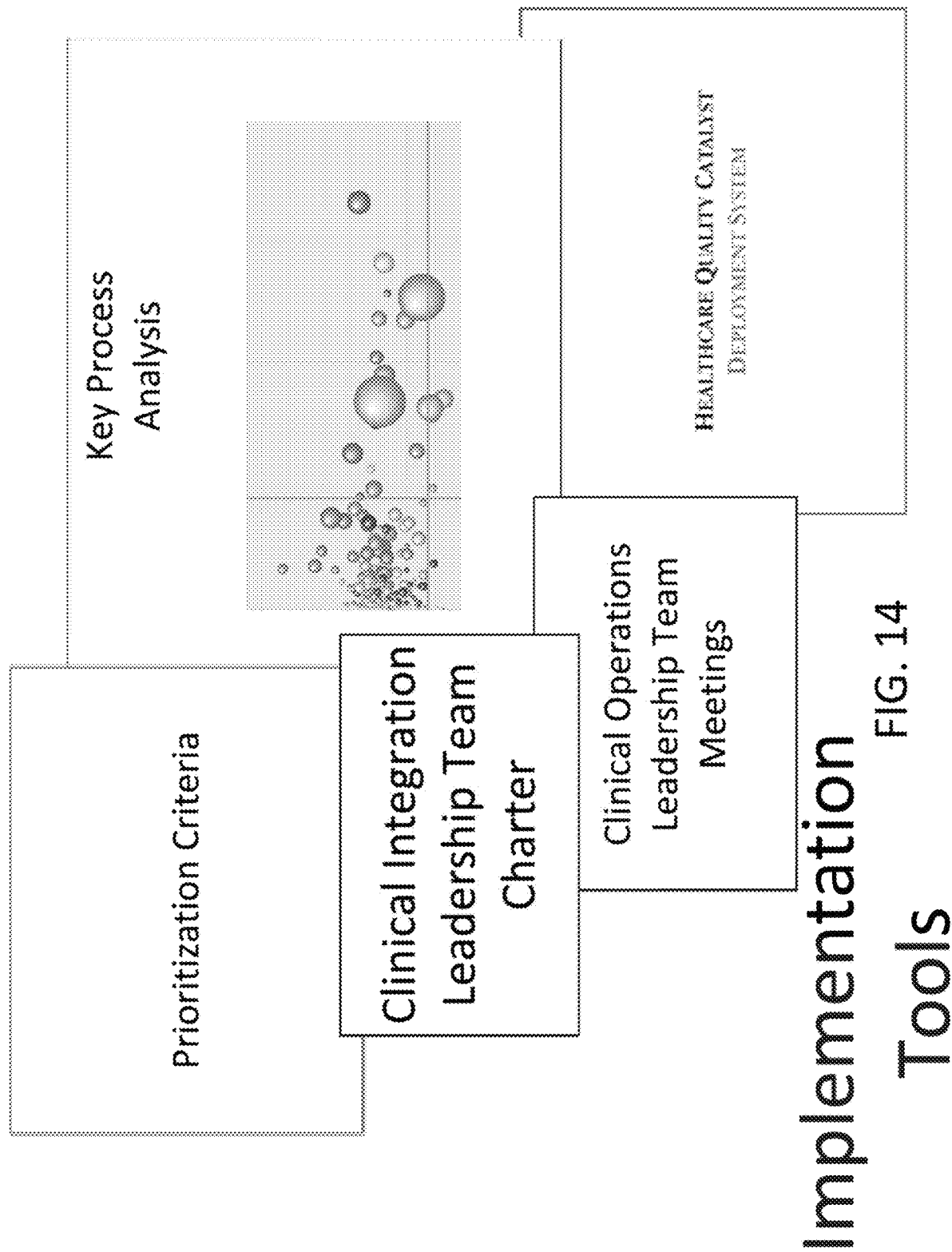
FIG. 14 illustrates examples of implementation tools, in accordance with at least one embodiment.

Alternatively or additionally, deployment tools might include implementation tools with supporting materials to assist the deployment teams in deploying the KAs' treatment criteria and implementing the changes. For example, as represented in FIG. 14, these implementation tools can include KPA deployment visualizations, team charters, sample prioritization criteria, job/position descriptions, sample meeting agendas, and the like.

Figure 20:
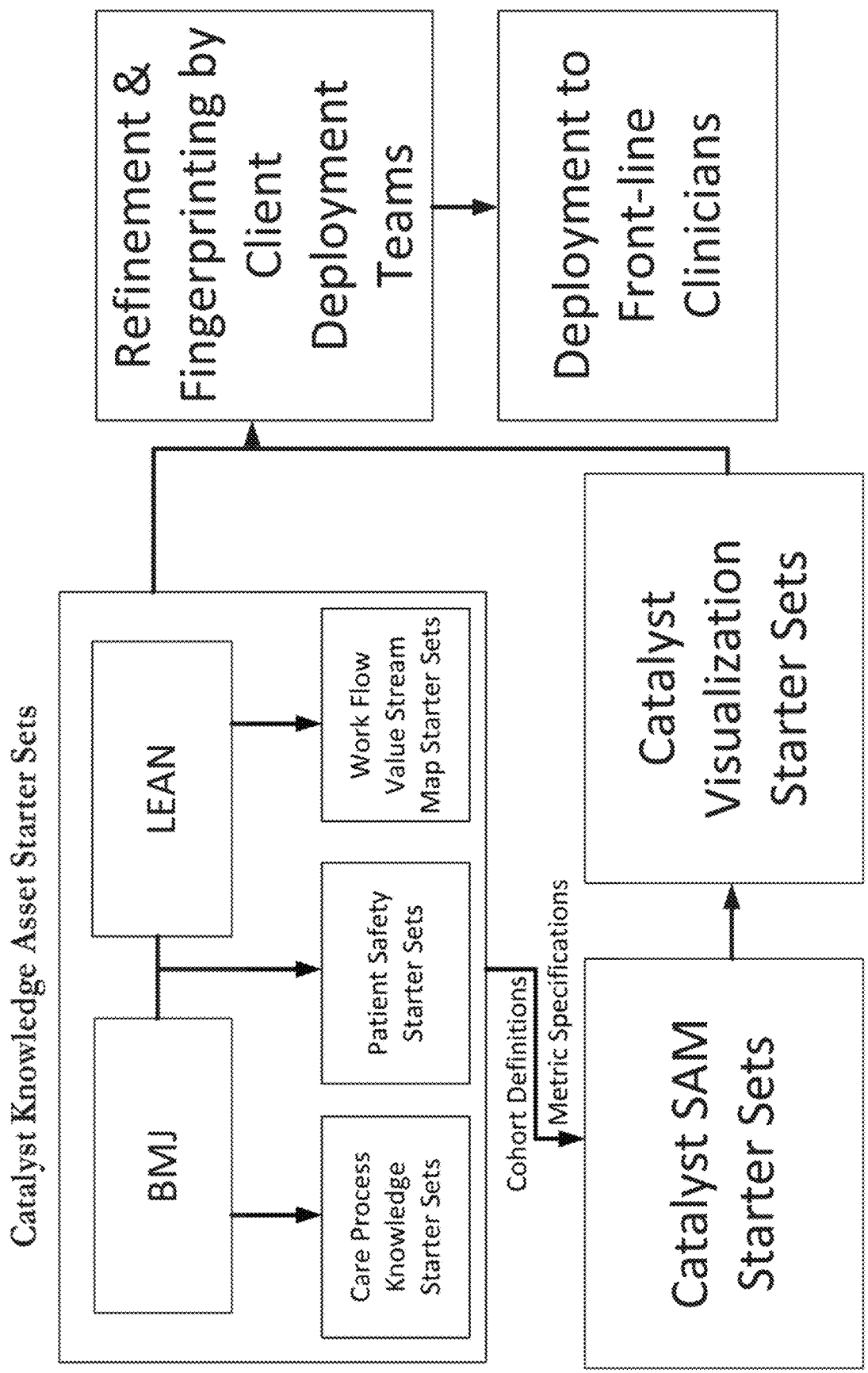
FIG. 20 illustrates an example of the clinical use of an exemplary method according to at least one embodiment.

FIG. 20 illustrates an example of the clinical use of method 400. As can be seen in the FIG. 20, KA starter sets are created. Furthermore, as discussed above, SAM starter sets and visualization starter sets are also created. The deployment team is then able to refine and fingerprint these starter sets to create their own knowledge assets, SAMs, and visualizations. Finally, the method can be implemented on the front line as it is deployed to the front-line clinicians.

Example System

The healthcare delivery improvement techniques described herein can be implemented in any suitable way. For example, in at least one embodiment these techniques, including the described healthcare delivery waste reduction tools, may be implemented at least in part by a waste reduction system. This waste reduction system may include, for example, a clinical content system, analytics system, and/or deployment system.

Figure 15:
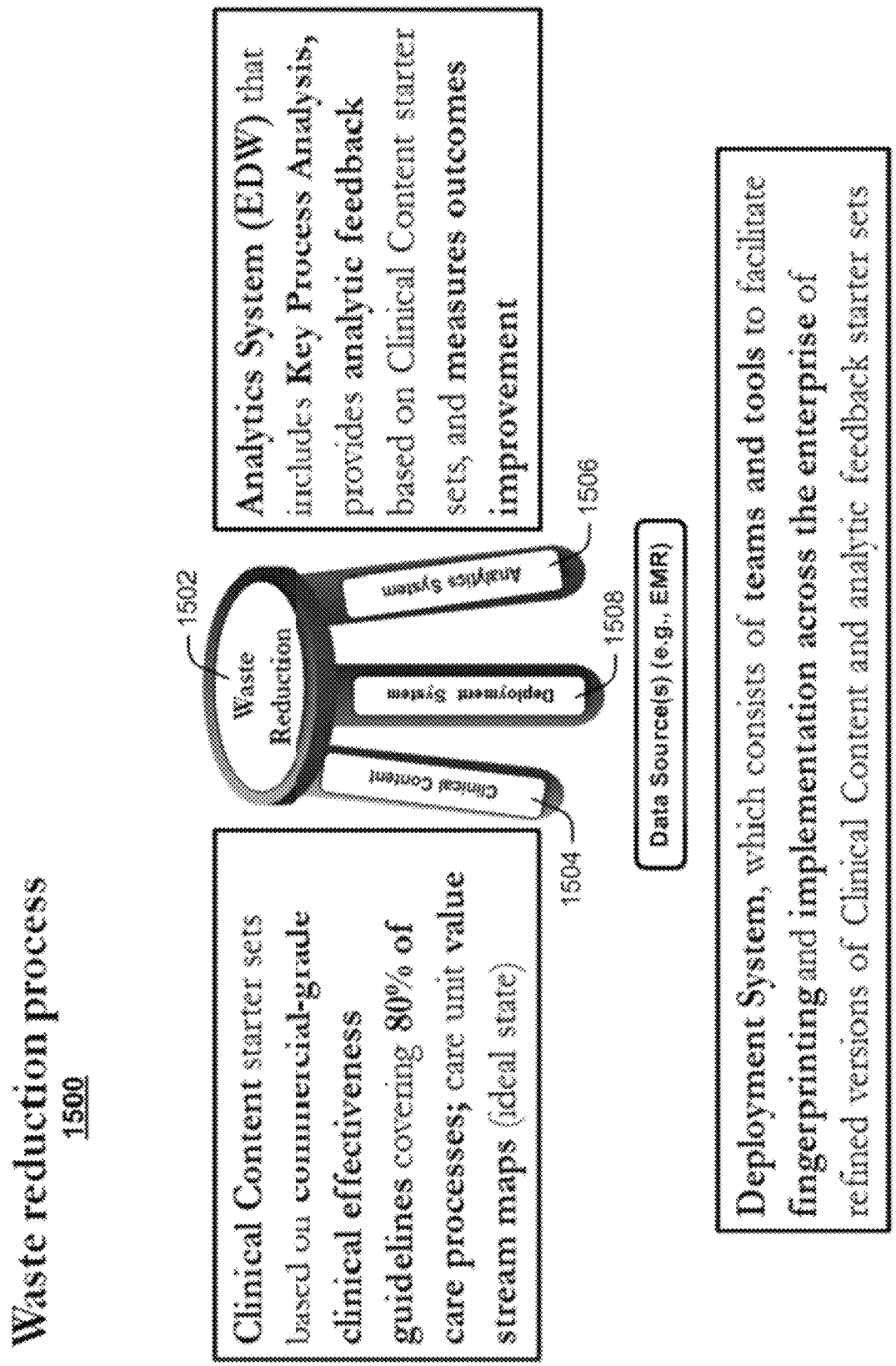
FIG. 15 illustrates an example waste destruction process representation, in accordance with at least one embodiment.

To facilitate the readers' understanding of such an example system, FIG. 15 illustrates an example waste reduction process 1500 that may be implemented in accordance with the described techniques. Here, waste reduction process 1500 includes a brief example description of waste reduction tools that may be associated with waste reduction 1502 (e.g., a waste reduction system).

More particularly, note that in this example clinical content starter sets (e.g., KA starter sets) are described for a clinical content 1504 (e.g., a clinical content system). KPA and analytical feedback, in turn, are described for an analytics system 1506. In this regard, here the analytics system 1506 is described with respect to an EDW, one example of which is an ADW that may be implemented in accordance with the described techniques. Finally, also note that teams (e.g., hierarchical deployment teams) and tools are described for a deployment system 1508.

Figure 16:
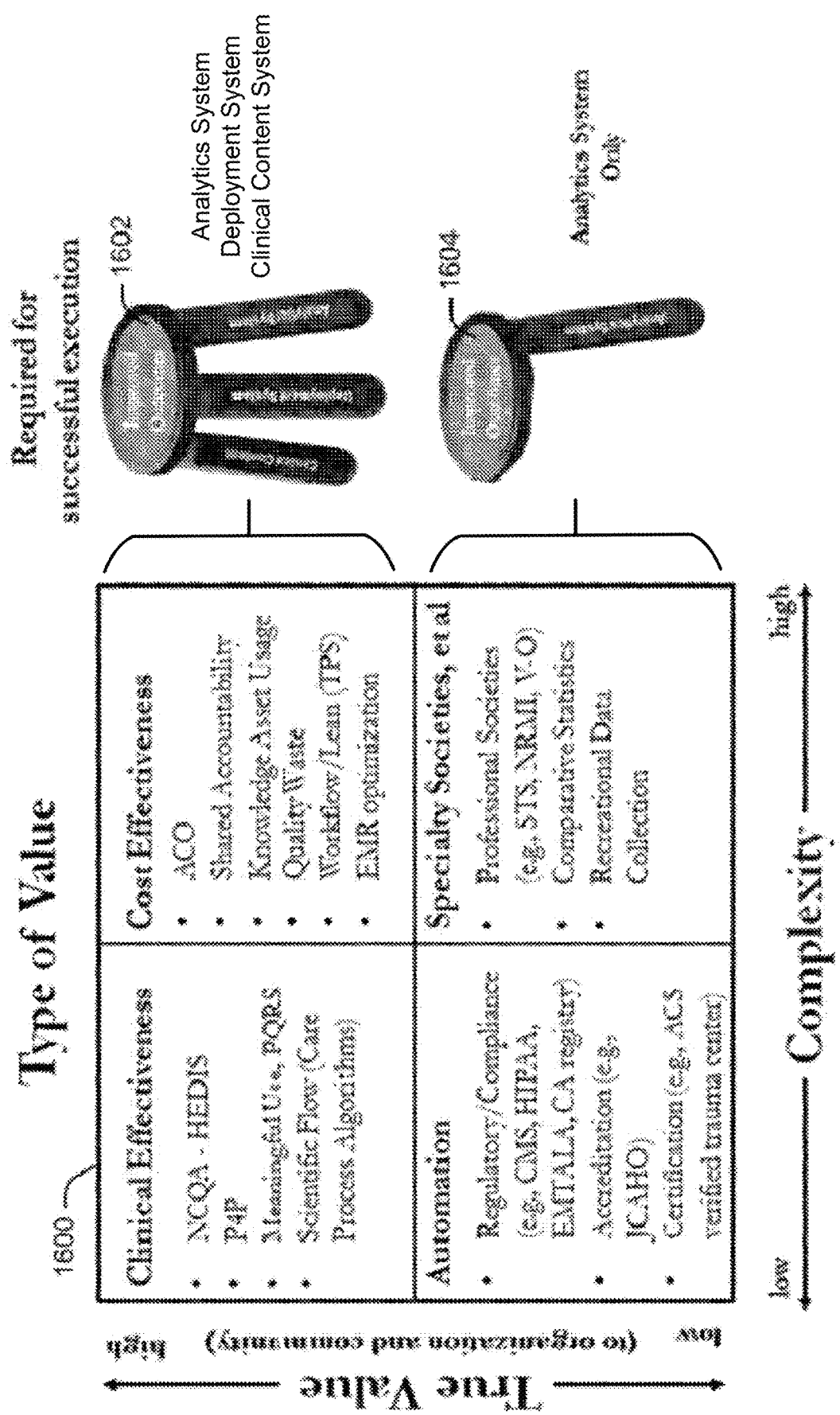
FIG. 16 illustrates an example value complexity table, in accordance with at least one embodiment.

FIG. 16 illustrates a value complexity table 1600 in relation to an improved outcomes 1602 and an improved outcomes 1604. Note that here; improved outcomes 1602 are associated with an analytics, deployment, and clinical content system. Improved outcomes 1604, in contrast, are associated with an analytics system, but are not associated with a deployment system or clinical content system. Note that the value complexity table 1600 includes individual example prerequisites organized by value type (i.e., type of value) for success arranged in a grid with respect to a true value range (low to high) along the table's y-axis and a complexity spectrum (low to high) along the table's x-axis.

Figure 17:
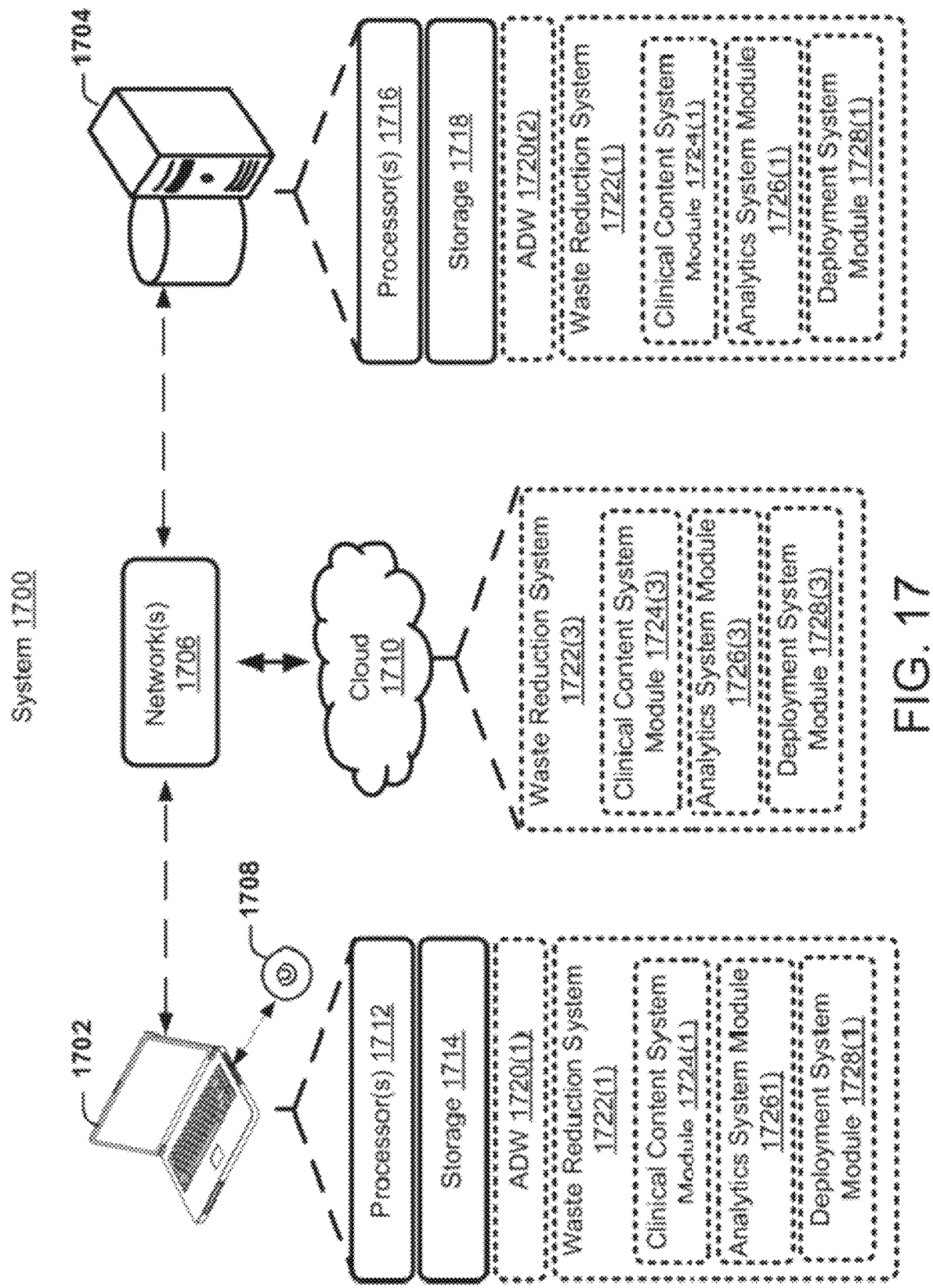
FIG. 17 illustrates an example system in which the described techniques may be implemented, in accordance with at least one embodiment.

FIG. 17 illustrates an example system 1700 in which the described healthcare delivery improvement techniques may be implemented, in accordance with at least one embodiment. In this example, the system 1700 includes multiple computing devices, represented here as computing devices 1702 and 1704. These computing devices can function in a stand-alone or cooperative manner to implement the described automatic UI rendering techniques.

Here, the computing device 1702 is shown embodied as a portable laptop computing device. Computing device 1704, in turn, is shown embodied as a server computing device. However, this is not intended to be limiting and it is to be appreciated and understood that the example system 1700 can include any number and type(s) of computing devices.

In this regard, the term "computing device", as used herein, can mean any type of device or devices having some amount of processing capability. Examples of computing devices can include traditional computing devices, such as personal computers (desktop, portable laptop, etc.), cell phones, server computing devices, tablets, smart phones, personal digital assistants, or any of a myriad of ever-evolving or yet to be developed types of computing devices.

Computing devices 1702 and 1704 can indirectly and/or directly exchange data via one or more network(s) 1706 and/or by any other suitable means, such as via an external storage 1708 for instance. Without limitation, the network(s) 1706 can include one or more local area networks (LANs), wide area networks (WANs), the Internet, and/or the like. Examples of external storage can include optical storage devices (e.g., CDs, DVDs etc.) and flash storage devices (e.g., memory sticks or memory cards), among others.

Additionally or alternatively, the computing devices 1702 and/or 1704 can exchange data with other resources associated with the cloud 1710, for example via the network(s) 1706. As used herein, the cloud 1710 refers to computing-related resources/functionalities that can be accessed via the network(s) 1706, although the location of these computing resources and functionalities may not be readily apparent.

Here, computing devices 1702 and 1704 can each include a processor(s) (i.e., central processing unit(s)) and storage. More particularly, here the computing device 1702 includes processor(s) 1712 and storage 1714. Similarly, the computing device 1704 includes processor(s) 1716 and storage 1718. The processor(s) 1712 and 1716 can execute data in the form of computer-readable instructions to provide the functionality described herein. Data, such as computer-readable instructions, can be stored on the storage 1714 and/or 1718. The storage 1714 and/or 1718 can include one or more of volatile or non-volatile memory, hard drives, optical storage devices (e.g., CDs, DVDs etc.), or the like.

The devices 1702 and 1704 can also be configured to receive and/or generate data in the form of computer-readable instructions from one or more other storages, such as the external storage 1708 for instance. The computing devices may also receive data in the form of computer-readable instructions over the network(s) 1706 that are then stored on the computing device(s) for execution by the processor(s).

As used herein, the term "computer-readable media" can include transitory and non-transitory instances. In contrast, the term "computer-readable storage media" excludes transitory instances. Computer-readable storage media can include "computer-readable storage devices". Examples of computer-readable storage devices include volatile storage media, such as RAM, and non-volatile storage media, such as hard drives, optical discs, and flash memory, among others.

Recall that by utilizing the described techniques, evidence-based clinical content and ADW functionality can be integrated to provide healthcare delivery waste reduction tools that allow waste to be significantly reduced or eliminated altogether. Also recall that in at least one embodiment, these waste reduction tools may be implemented at least in part by a waste reduction system. This waste reduction system may include, for example, a clinical content system, analytics system, and/or deployment system.

Accordingly, in this example the computing device 1702 is shown as being configured to implement at least part of an ADW 1720 (i.e., as ADW 1720(1)) and at least part of a waste reduction system 1722 (i.e., as waste reduction system 1722(1)).

The computing device 1704, in turn, is shown as being configured to implement at least part of the ADW 1720 (i.e., as ADW 1720(2)) and at least part of the waste reduction system 1722 (i.e., as waste reduction system 1722(2)). Similarly, at least part of the ADW 1720 and/or at least part of the waste reduction system 1722 is shown as being implementable by one or more distributed computing resources of the cloud 1710 (i.e., as ADW 1720(3) and/or waste reduction system 1722(3)).

By leveraging (e.g., utilizing) the functionality of the ADW 1720, the waste reduction system 1722 can be implemented to perform some or all of the described techniques and functionalities, such as or all of the method described above relative to FIG. 4 for instance. To accomplish this, the waste reduction system 1722 can include any number of modules configured to provide the waste reduction tools described above.

In this example, the waste reduction system 1722 includes a clinical content system module 1724, analytics system module 1726, and deployment system module 1728. Note that the waste reduction tools provided by the waste reduction system 1722 can be provided by any combination of these modules. Additionally, in at least one embodiment, the waste reduction system 1722 may include other modules that, for the sake of brevity, are not shown.

Here, the clinical content system module 1724 can be configured to provide one or more waste reduction tools, such as those providing functionality for utilizing clinical content to create KAs.

Furthermore, in at least one embodiment, the clinical content system module 1724 can provide some or all of the functionality of the KIT described above. For example, the clinical content system module 1724 can provide KIT functionality that facilitates the creation of KAs, including KA starter sets. This functionality can be associated with formatting KAs to be as seamless as possible/compatible with the ADW 1720. Alternatively or additionally, this functionality may allow the KIT to be utilized by PCS subject matter experts and/or others to customize KAs, such as KA starter sets for instance.

The analytics system module 1726, in turn, can also be configured to provide one or more waste reduction tools. For example, the analytics system module 1726 can provide functionality for utilizing KAs to create corresponding SAMs, utilizing the SAMs to track treatment practices and outcomes, and/or providing analytical feedback based on the tracked treatment practices and outcomes, as described above.

Furthermore, in at least one embodiment, the clinical content system module 1724 can provide some or all of the functionality of the KIT described above. For example, the clinical content system module 1724 can provide KIT functionality for creating SAMs, including SAM starter sets. This may include defining SAM cohorts and/or selecting treatment criteria for the SAMs. Alternatively or additionally, this functionality may allow the KIT to be utilized by PCS subject matter experts and/or others to customize SAMs, such as SAM starter sets for instance.

Finally, the analytics system module 1726 can also be configured to provide one or more waste reduction tools. For example, the analytics system module 1726 can provide functionality for providing deployment tools, such as those described above. These deployment tools may be based on the KAs, the analytical feedback, and/or the tracked treatment practices.

With respect to the implementation of the ADW 1720 and/or waste reduction system 1722, in at least one embodiment the computing device 1702 may function in a stand-alone configuration such that all of the ADW 1720 and/or waste reduction system 1722 is implemented by the computing device 1702. For example, the clinical content system module 1724, analytics system module 1726, and deployment system module 1728 can all be implemented by resources provided by the computing device 1702.

In other embodiments however, at least some of the ADW 1720 and/or waste reduction system 1722 may be implemented using other resources provided by the computing device 1704, the cloud 1710, and/or one or more other computing-related resources/functionalities. For example, all or part of the clinical content system module 1724, analytics system module 1726, and/or deployment system module 1728 may be implemented by the computing device 1704 and/or the cloud 1710.

Updating the ADW from Operational Data Sources

In order to provide the most current data for analysis, ADW 1720 should be periodically updated from the operational data sources. Referring to FIG. 6, this involves periodically retrieving data from the sources 606 into the source marts 604, and then using the source mart data to update the tables and views in the SAMs 612.

Figure 21:
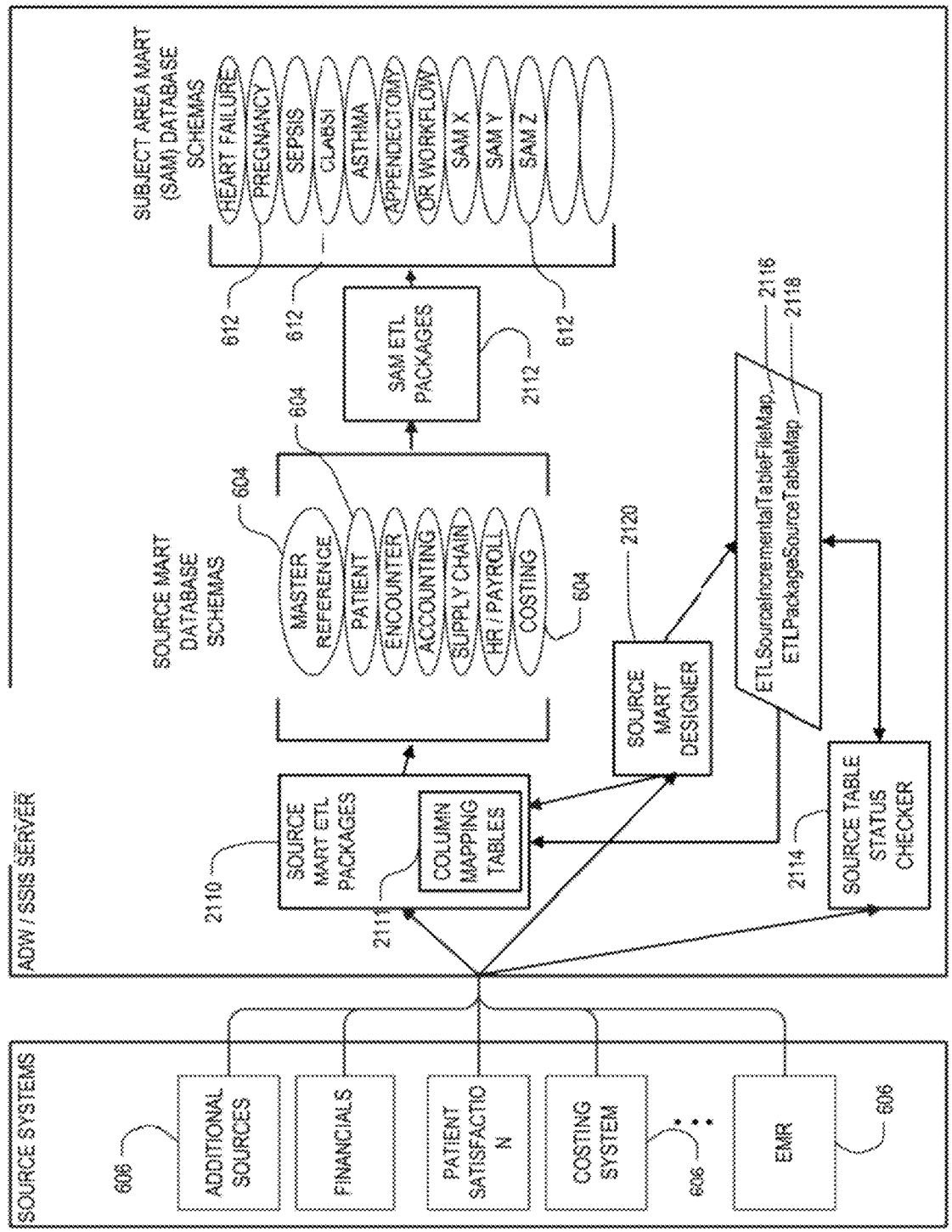
FIG. 21 is a view of parts of the ADW Architecture of FIG. 6, adapted for highlighting aspects pertinent to data update features.

FIG. 21 is another view of parts of the ADW Architecture 600 as illustrated in FIG. 6, adapted for highlighting aspects pertinent to data update features. The view of FIG. 21, in addition to the source systems 606, source mart database schemas 604 and SAMs 612, also illustrates program modules for performing the data updating, tables in support of such program modules, and a program module to automatically build or configure parts of the data updating modules. In different embodiments, the program modules and support data can be distributed over one or more computer systems. Note that as used herein, the term "program module" does not necessarily imply any unity of structure. For example, two or more program modules, when considered together, still constitute a "program module" as that term is used herein. Also, a "database" is considered herein to include one or more tables. That is, a single table is considered herein to be a special case of a "database".

The ADW includes Source Mart ETL Packages 2110 which draw data periodically from the source systems 606 into the source marts 604. In the embodiment shown, the program modules for accomplishing this task are written for Microsoft® SQL Server Integration Services (SSIS), and the modules themselves are known as "ETL packages", or merely "packages". However, other embodiments can use other program environments for implementing the modules. The source mart packages 2110 also include respective column mapping tables 2111, which are discussed below with respect to FIG. 27. The ADW also includes SAM ETL Packages 2112, which draw data periodically from the source marts 604 (and optionally from other sources, such as IDEA), into the SAMs 612. The SAM packages 2112 can be structured similarly to the Source Mart ETL packages 2110, but typically they will include much more involved data transformation functions. SAM packages 2112 are discussed in greater detail above with respect to FIGS. 34-37. The ADW also includes a Source Table Status Checker 2114, which among other things, queries the source systems repeatedly to ensure that their own data is up-to-date, and so notifies the source mart packages 2110, via tables 2116 and 2118, as described further hereinafter. The ADW also includes a source mart designer 2120 which automates some of the steps for developing the source mart packages. The source mart packages 2110, source mart designer 2120, and source table status checker 2114 all communicate with the source systems by mechanisms appropriate to the particular source system. For example, the program modules may communicate using the source system's API, or by SQL-over-IP, or by some other protocol. Typically the communication will occur over a network such as 1706.

The ADW contains many source mart packages 2110, each roughly corresponding to one of the destination table in the source marts 604. Typically each destination table is loaded by a different package 2110. As can be seen below, this allows finer granularity pipelining. Some packages may load more than one destination table, and if they are small tables, that grouping will not significantly degrade the efficiencies gained by pipelining the load process.

Figure 22:
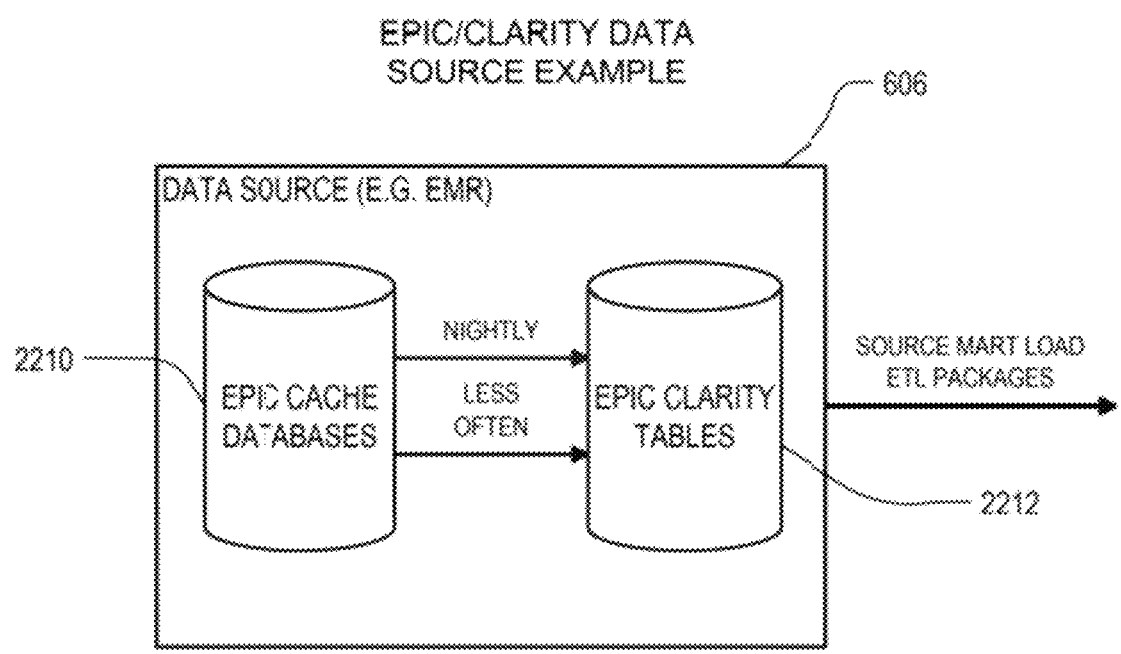
FIG. 22 illustrates components of an Epic/Clarity-based source system of FIG. 21.

The structure and operation of FIG. 21 will be described primarily with respect to the loading of source mart tables from an Epic® EMR data source. In the Epic system, data is initially entered into a database known as Epic Cache, designated 2210 in FIG. 22. Periodically, the Epic system loads the data into another database known as Epic Clarity 2212. In a typical installation some of the tables in Clarity 2212 are loaded nightly, whereas others, such as tables containing data that do not change often, may be loaded less often. The Clarity database acts as a data warehouse that can be queried and read from by outside systems such as ADW 600.

Returning to FIG. 21, all of the source mart packages 2110 can be scheduled to run at about the same time each night. However, they do not actually retrieve any data from the source systems 606 until they are satisfied that the data they will retrieve is up-to-date. Importantly, instead of waiting until all of the source tables are up-to-date, each package waits only for the specific source tables on which it is dependent. For example, while the Epic Clarity database may contain hundreds or thousands of database tables, a particular source mart package may require data from only 10 of them. In that case the package will wait only for those 10 to be reported up-to-date, before beginning its data retrieval process. Note that since different packages will have different table dependencies, most of them will start retrieving data at different times, thereby pipelining the process. In addition, if it is known that a particular source table is not updated nightly, then the packages that retrieve data from that table can be configured to not wait for those tables to be reported as being up-to-date. Still further, some packages may be configured to wait until certain others of the source mart packages have completed their loading process.

Figure 23:
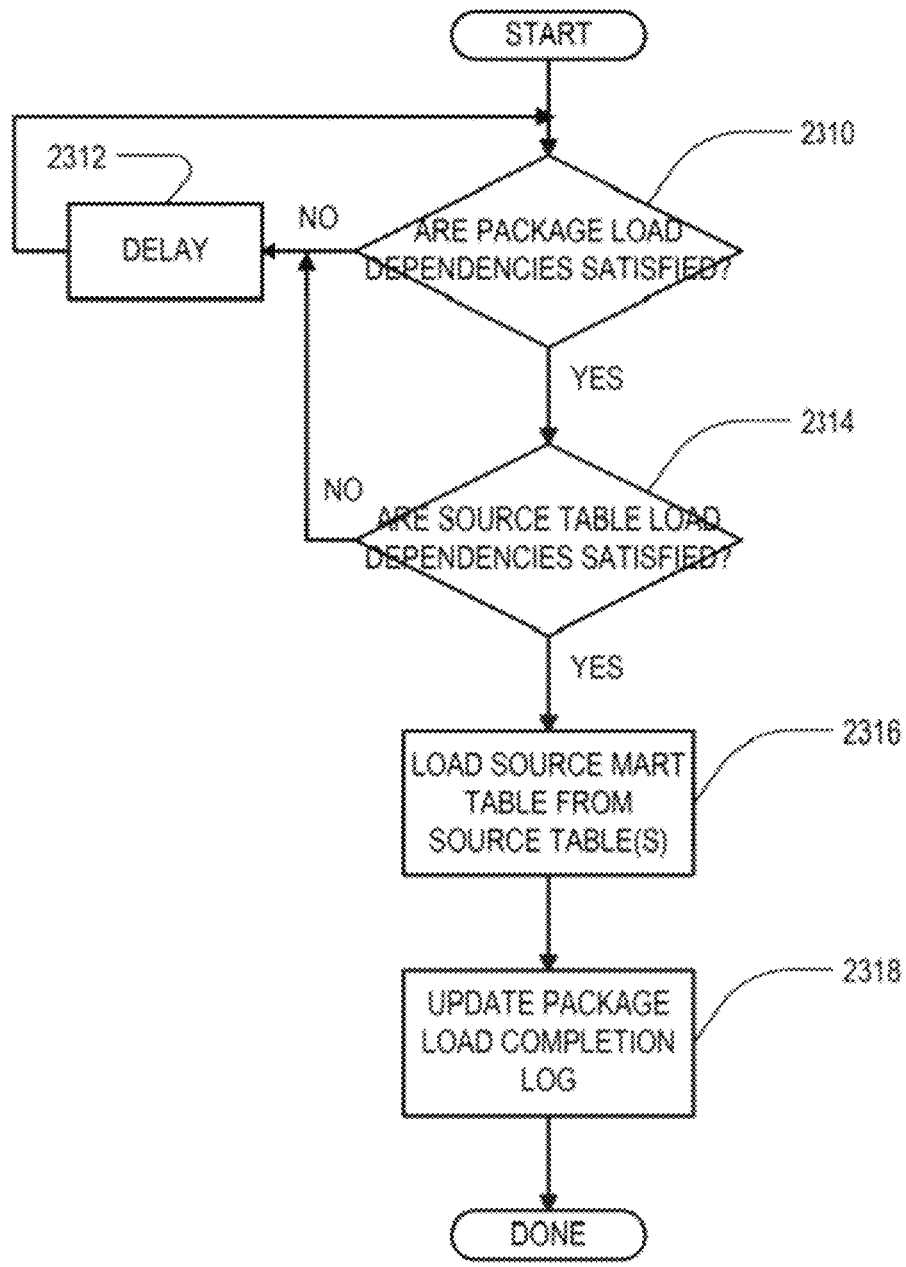
FIGS. 23, 25, 26, 28 and 29 are flow charts illustrating the operation of source mart table load packages of FIG. 21.

FIG. 23 is a flow chart illustrating the operation of a typical source mart table ETL package 2110. As with all flowcharts herein, it will be appreciated that many of the steps can be combined, performed in parallel or performed in a different sequence without affecting the functions achieved. In some cases, as the reader will appreciate, a re-arrangement of steps will achieve the same results only if certain other changes are made as well. In other cases, as the reader will appreciate, a re-arrangement of steps will achieve the same results only if certain conditions are satisfied. Furthermore, it will be appreciated that the flow charts herein show only steps that are pertinent to an understanding of the invention, and it will be understood that numerous additional steps for accomplishing other functions can be performed before, after and between those shown.

Referring to FIG. 23, in step 2310, the module first determines whether all package load dependencies have been satisfied. This step is not required in all packages. In a typical implementation, for example, two special ones of the packages for loading source marts from an EMR may populate a Patient Table and a Provider Table respectively, and translate the data in each of them to common linkable identifiers (CLIs) 608 (FIG. 6). These two packages do not have any package load dependencies and therefore omit step 2310. All other packages in this example, however, are configured to wait until those two special packages complete before beginning their own data loads. Most packages therefore would include step 2310. As will be seen, when each package completes it writes the name of the package together with a completion Date-Time Stamp (DTS) into a package load completion log. Step 2310 thus can determine whether a particular predecessor package has completed, by querying the package completion log for the most recent completion DTS for the predecessor package. Only if the DTS is sufficiently recent, then the dependency on that package is considered satisfied. For example, if packages run nightly, step 2310 may check to ensure that the most recent completion DTS for the predecessor package is within the last two hours.

If not all the package load dependencies for the current package are satisfied, then in step 2312 the package sleeps for a period of time, for example six minutes. It then tries again by returning to step 2310. If all package load dependencies are satisfied, then the package continues to step 2314 where it is determined whether all required predecessor source tables are up-to-date. Before explaining how this determination is made, it will be useful to describe two tables, ETLSourceIncrementalTableFileMap table 2116 and ETLPackageSourceTableMap table 2118, which are maintained in the ADW 600. ETLSourceIncrementalTableFileMap table 2116 is sometimes referred to herein also as a source table information database, and ETLPackageSourceTableMap table 2118 is sometimes referred to herein also as a table dependency information database. Briefly described, ETLSourceIncrementalTableFileMap table 2116 tells the source table status checker 2114 which source system tables are predecessors and must be up-to-date before one or more of the source mart packages 2110 can run. The source table status checker 2114 repeatedly queries the source system for the load status and last update DTS of each listed source table, and as it learns of source tables that are now up-to-date, it writes their load status and last update DTS into the ETLPackageSourceTableMap table 2118. Each of the source mart packages 2110 repeatedly checks the ETLPackageSourceTableMap table 2118 for the load status and last update DTS of its predecessor source tables, and proceeds to load data only when they are all up-to-date.

ETLSourceIncrementalTableFileMap table 2116, in the Epic/Clarity embodiment, is a single table used for all the source mart packages 2110. It contains the mapping of Clarity tables to the Epic file(s) that they load from, but only for those Clarity tables that are loaded from Epic daily. Those Clarity tables loaded less frequently are omitted. Each record in ETLSourceIncrementalTableFileMap table 2116 contains fields for the following information (among others): Clarity Table Name, Load File Name(s), Last Source Load Completion DTS and Last Source Load Status DSC (Description). The first two of these fields are filled upon development of the source mart packages 2110, and the last two are filled by the source table status checker 2114 during daily operation.

ETLPackageSourceTableMap table 2118, in the Epic/Clarity embodiment, also is a single table used for all the source mart packages 2110. Among other things, table 2118 contains the mapping of ADW ETL packages to Clarity tables referenced in the package. This table includes all Clarity tables used in each package, even those that update less frequently than daily in the Clarity system. However, table 2118 also includes a WaitForThisTableFLG field in each record, which contains "Y" only if Clarity updates the Clarity table daily. All tables having a WaitForThisTableFLG="Y" are also represented in the ETLSourceIncrementalTableFileMap table 2116. Each record in ETLPackageSourceTableMap table 2118 contains fields for the following information (among others): A Package Name, a Clarity Table Name, Last Source Load Completion DTS (or NULL if the Clarity table has not yet been updated), Last Source Load Status DSC (or NULL if the Clarity table has not yet been updated), and the WaitForThisTableFLG. Of these, the Last Source Load Completion DTS and the Last Source Load Status DSC are filled by the source table status checker 2114 during daily operation, and the remainder are filled upon development of the source mart packages 2110.

Returning to FIG. 23, it can be seen from the above that a source mart package 2110 need only check ETLPackageSourceTableMap table 2118 in order to determine whether all the source system tables needed for the current package, are up-to-date. If all records of ETLPackageSourceTableMap table 2118 that have the name of the current package in the Package Name field and "Y" in the WaitForThisTableFLG, also have "Success" (or some other non-fail result code) in their Last Source Load Status DSC field and a sufficiently recent DTS in their Last Source Load Completion DTS field, then all table load dependencies for the current package have been satisfied. A single SQL SELECT statement is sufficient to make this determination. Moreover, except for the package name parameter, this SELECT statement can be identical for all source mart ETL packages 2110 since all other parameters needed to customize it for a particular package are stored in ETLPackageSourceTableMap table 2118.

If in step 2314 the package determines that not all source table load dependencies have been satisfied, then again in step 2312 the package sleeps for a period of time, and then tries again by returning to step 2310. If all source table load dependencies are satisfied, then the package continues to step 2316 to load the source mart table from the source system table(s). Then, in step 2318, the package updates the package load completion log with the name of the current package, a completion Date-Time Stamp (DTS), among other things. Note that the package completion log can itself be a database in some embodiments.

As previously mentioned, different source mart packages 2110 can run start loading data from the source system at different times, as soon as all the dependencies for that particular source mart package 2110 have been satisfied. This means that some source mart packages 2110 can begin loading data from the source system before all the source system tables are up-to-date. It also means that later-starting source mart packages 2110 can begin loading data before one or more earlier-starting source mart package has finished loading data. In this manner, the loading of source mart tables is a parallel operation with the different packages loading data asynchronously with each other. The loading of source mart tables also is pipelined with the updating of the source tables internally in the source system.

For example, assume there are three source mart packages with different dependencies as follows: Package 1 depends on source tables A, B, C, D; Package 2 depends on source tables A, B, E, F; and Package 3 depends on source tables B, D, F, G. Then assume that in a particular night, the source system happens to complete the updating of its source tables in the following sequence: A, B, C, D, E, F, G, etc. In this example, Package 1 will start loading data after source table D has been updated. While Package 1 loads data into its source mart table, the source system continues to update its source tables E, F and G. Package 2 cannot start yet, but does start after source table F has been updated. At this time, package 1 may or may not have completed. If not, then packages 1 and 2 will run in parallel for a while. While Package 2 loads data into its source mart table, the source system continues to update its source table G. Thus Package 2's loading of data into its source mart table can run in parallel with the source system's updating of its source table G, and possibly also in parallel with Package 1's continued loading of data into its own source mart table. Package 3 also does not start yet, but does start after source table G has been updated. At this time, package 1 and/or 2 may or may not have completed. Thus packages 1 and 3, or packages 2 and 3, or possibly even all three packages, may run in parallel for a while.

The time delay after the last table in the source system has been updated and the completion of the source mart table load process is sometimes referred to herein as the "slack time". It can be seen that because of the parallel, asynchronously starting, pipelined nature of the source mart table load process, the slack time can be made very short. This is as distinguished from a conventional system in which all source system tables must finish updating before any of the source system data begins loading into the data warehouse; in the latter case the data warehouse tables may not be available for use until hours after the source system tables finish updating.

It can also be seen that the granularity with which the source mart table load processes are divided up among asynchronously starting packages can affect the slack time. Minimum slack time is usually achieved when each source mart table load waits only for its own specific source table dependencies before starting (which in the FIG. 23 embodiment means that each source mart table load is run by a separate package). In some instances, though, more than one source mart table load can be included in a single package with little or no impact on the slack time. This is the case where the tables are small, for example, or where they all have the same source table dependencies. In a package which loads more than one source mart table, it is preferable that all of such loads be started immediately after step 2314 indicates that the dependencies are satisfied, and that they run in parallel with each other.

As mentioned, the ETLPackageSourceTableMap table 2118, which each source mart package checks repeatedly in step 2314 to determine whether its dependencies have been satisfied, is kept up-to-date by source table status checker 2114. Source table status checker 2114 is a parallel process that runs asynchronously from the source mart packages, and repeatedly queries the source system for the load status and last update DTS of each listed source table. As source table status checker 2114 learns of source tables that have been brought up-to-date in the source system, checker 2114 writes this information into the ETLPackageSourceTableMap table 2118.

Figure 24:
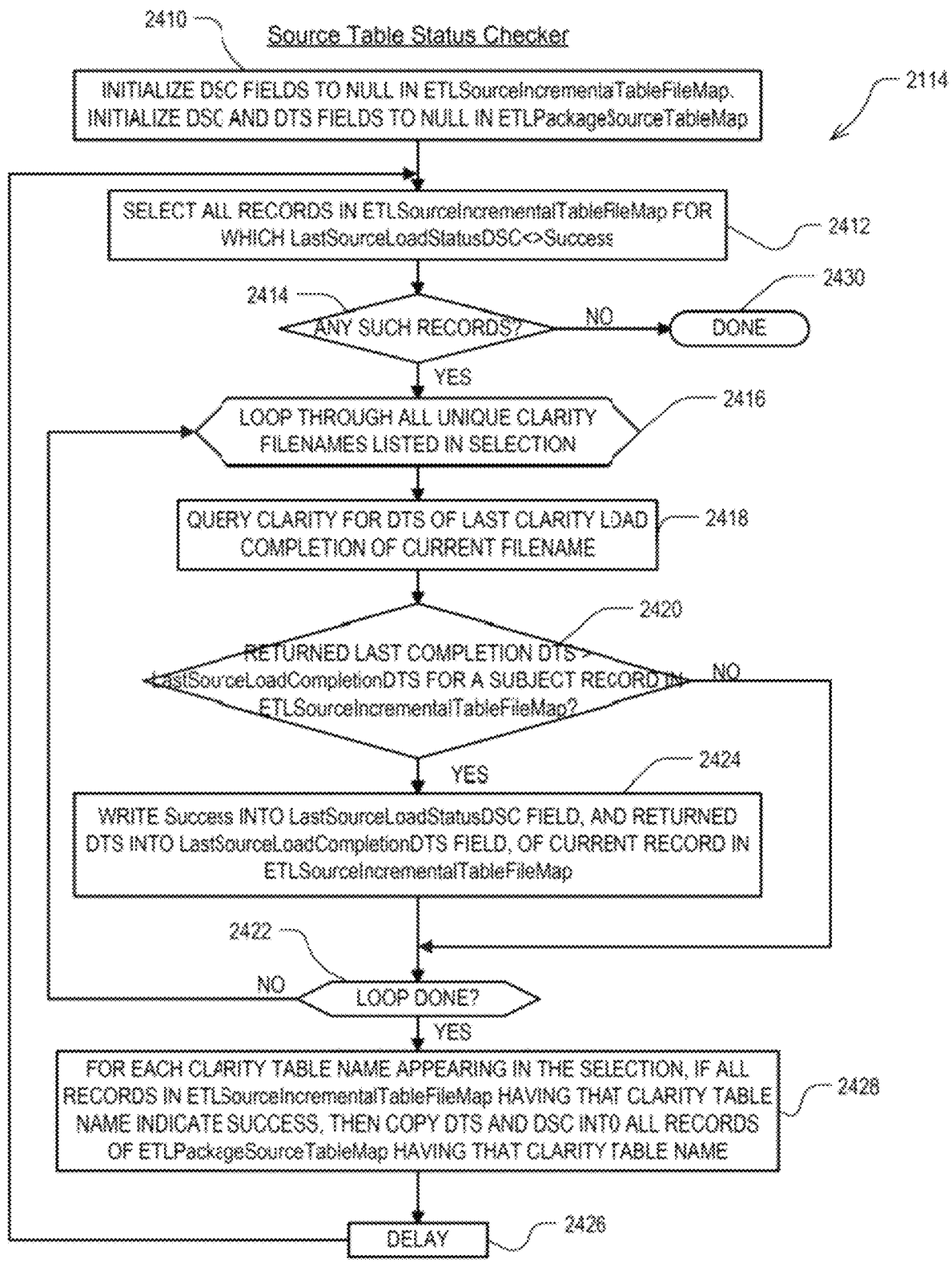
FIG. 24 is a flow chart illustrating the operation of an example source table status checker of FIG. 21.

FIG. 24 is a flow chart illustrating the operation of source table status checker 2114. It is described here for use with an Epic/Clarity-based source system, but it will be apparent to the reader how it can be adapted for use with other types of source systems. The flow chart of FIG. 24 can be implemented as its own SSIS package.

In step 2410, the LastSourceLoadStatusDSC field is initialized to NULL in all records in ETLSourceIncrementalTableFileMap table 2116. The LastSourceLoadCompletionDTS field is not initialized at this time, since it contains the DTS of the prior night's run and will be needed to compare against any completion DTS reported by the source system in the current run to determine whether the subject file load has completed in the current run. In ETLPackageSourceTableMap table 2118, both the LastSourceLoadStatusDSC field and the LastSourceLoadCompletionDTS field are initialized to NULL. Source mart load packages 2110 reading ETLPackageSourceTableMap table 2118 at this time will not find their dependencies satisfied yet.

In step 2412, the status checker 2114 selects all records in ETLSourceIncrementalTableFileMap table 2116 for which the LastSourceLoadStatusDSC field does not indicate that the last load completed successfully. This will return, for example, the records for all the Epic files whose load into Epic Clarity tables has not yet been identified by status checker 2114 as having completed. Most Clarity tables receive data from only one Epic source file, though some tables receive data from more than one Epic source file. In the latter situation, ETLSourceIncrementalTableFileMap table 2116 will contain a separate record for each Epic source file.

Since ETLSourceIncrementalTableFileMap table 2116 contains records for only those source system tables which must be up-to-date before the dependencies are satisfied in one or more of the source mart packages, the records returned by step 2412 indicate all the Epic files which are being loaded into Clarity tables that are needed by one or more packages, and which have yet been identified by status checker 2114 as having completed. In step 2414, it is determined whether there are any such records.

If there are, then in step 2416 the status checker 2114 begins a loop through all records listed in the selection. In step 2418 the status checker 2114 queries the Clarity source system for the date-time stamp of the most recent Clarity load completion of the current Epic filename. In step 2420 it is determined whether the last completion DTS returned in step 2418 is larger (more recent) than the value currently in the LastSourceLoadCompletionDTS field for the current record in ETLSourceIncrementalTableFileMap 2116. If not, then the Epic system has not yet finished loading data from the current Epic filename into Clarity tables. Thus in step 2422 the status checker 2114 returns to step 2416 to continue the loop. If in step 2420 it is determined that the last completion DTS returned in step 2418 is larger than the value currently in the LastSourceLoadCompletionDTS field for the current record in ETLSourceIncrementalTableFileMap 2116, this indicates that the subject Epic file has finished loading into all Clarity tables in the source system. Thus in step 2424, the status checker 2114 writes "Success" into the LastSourceLoadStatusDSC field in the current record of ETLSourceIncrementalTableFileMap table 2116. It also writes the returned DTS into the LastSourceLoadCompletionDTS field in the current record. Status checker 2114 then returns to step 2416 to continue the loop.

After all records in the selection from step 2412 have been queried in the loop 2416, ETLPackageSourceTableMap table 2118 is updated with any newly determined Clarity table load completion information. More specifically, for each Clarity table name appearing in the selection from step 2412, if all records in ETLSourceIncrementalTableFileMap having that Clarity table name indicate success, then in step 2428 the status checker 2114 copies the DTS and DSC fields into all records of ETLPackageSourceTableMap having that Clarity table name.

In step 2426 the status checker 2114 inserts a delay, and then returns to step 2412 to again select all records in ETLSourceIncrementalTableFileMap table 2116 for which the LastSourceLoadStatusDSC field does not indicate that the last load completed successfully, and to query the Epic system anew for the completion status of identified Epic filenames.

If in step 2414 it is determined that no records were returned in the selection of step 2412, this indicates that the Epic system has finished loading all the Clarity tables on which any of the source mart packages depend, and the source table status checker exits (step 2430).

As mentioned, the flow chart of FIG. 24 is specifically for use with an Epic/Clarity source system. It detects that a particular Clarity table is up-to-date by detecting that all Epic files from which data loads into that Clarity table have completed loading. When a particular Clarity table has been determined to be up-to-date, the status checker signals that to any source mart packages 2110 that might be awaiting completion of that table. Other source systems, such as those from PeopleSoft® and Cerner®, each have their own method to determine whether a table from which a source mart package 2110 will pull data, is up-to-date. The reader will know how to adapt the method of FIG. 24 to properly use the method appropriate to each type of source system.

In addition, when a particular source system table has been determined to be up-to-date, the status checker of FIG. 24 signals that to the source mart packages 2110 by writing a table completion status and DTS into an intermediary table, ETLPackageSourceTableMap table 2118, which the source mart packages 2110 periodically query. It will be appreciated that another embodiment may employ a different method to notify the source mart packages 2110 when each source system table has been determined to be up-to-date. Many variations will be apparent to the reader.

Returning to FIG. 23, it was mentioned that in step 2316, the source mart package loads its destination source mart table from one or more source system tables. Typically, the source mart (destination) tables are set up to receive all the columns from a corresponding base table in the source system, modified and augmented in a number of ways. First, the column names are changed (mapped) to new column names that satisfy naming standards predetermined for the ADW. Second, certain common linkable identifiers (CLIs) 608 are defined in the ADW. In a typical embodiment two CLIs are defined: one identifying a particular patient and one identifying a particular provider. Thus each destination table that includes a column identifying a patient or a provider is also augmented with an additional column containing the CLI for that patient or provider. Third, any lookup tables in the source system are joined into the destination source mart table (for example by an SQL LEFT OUTER JOIN operation), such that whereas the source system may contain a column in the base table that contains a cryptic code, and a second (lookup) table contains a correspondence between the code and a human readable description, the destination source mart table will join these such that the description appears in a column of the table in addition to the code.

Figure 25:
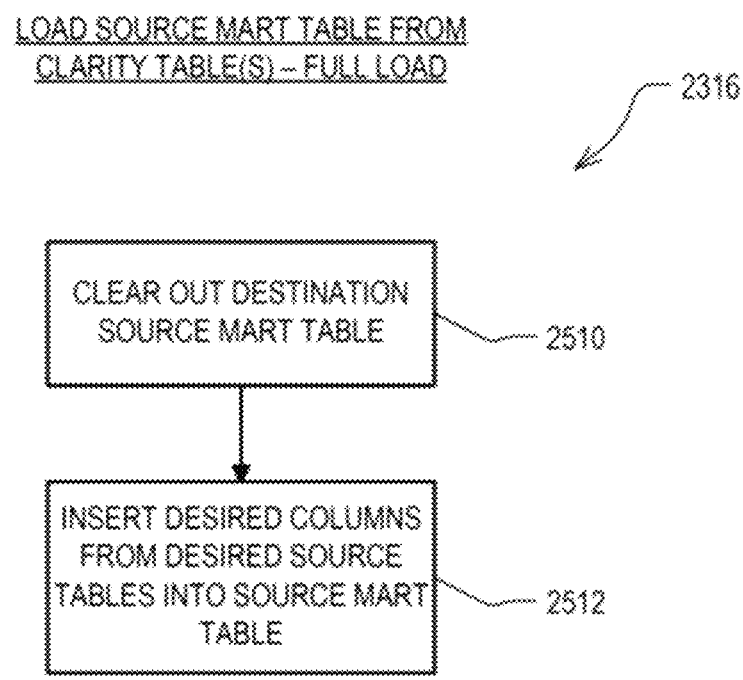

FIG. 25 is a flow chart detail of step 2316 for a source mart package 2110 that performs a "full" load of its destination table. Some source mart packages 2110 perform only incremental loads, and they will be discussed later. In step 2510, for a full load, the source mart package 2110 first completely clears out the destination source mart table. In SQL, this can be accomplished by truncating the table to zero records. Then, in step 2512, the source mart package 2110 inserts the data from the desired columns of the source system tables into the source mart table.

Figure 26:
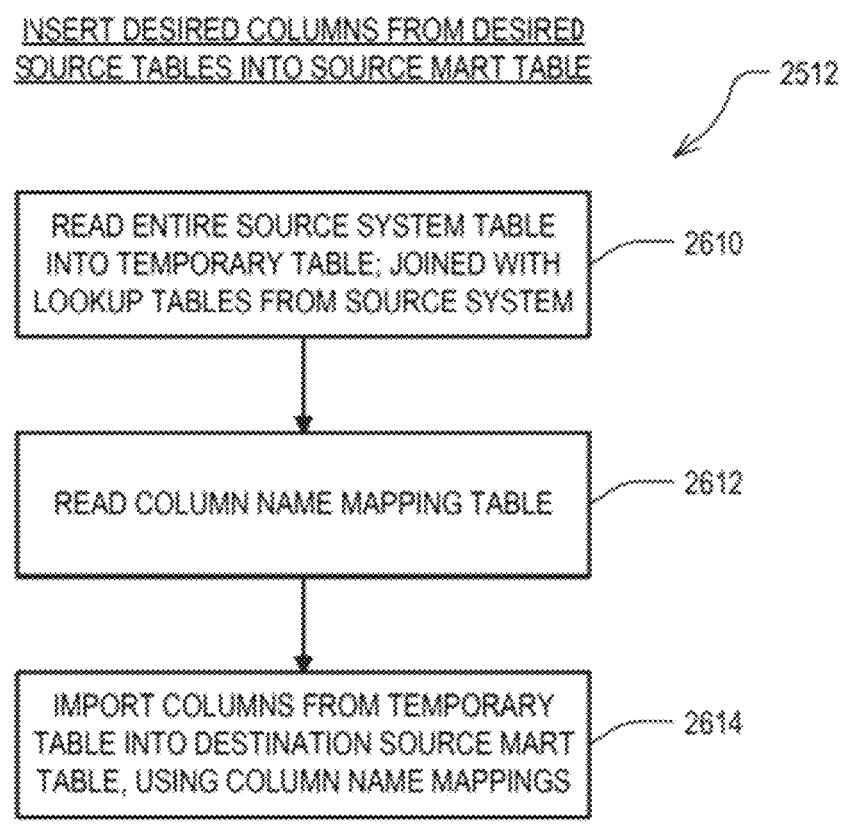

FIG. 26 is a flow chart detail of step 2512 for inserting the data from the desired columns of the source system tables into the source mart table. In step 2610, the source mart package 2110 reads the entire source system base table into a temporary table, joined with lookup tables from the source system as needed. Typically step 2610 can be implemented with a single SQL SELECT statement.

Figure 27:
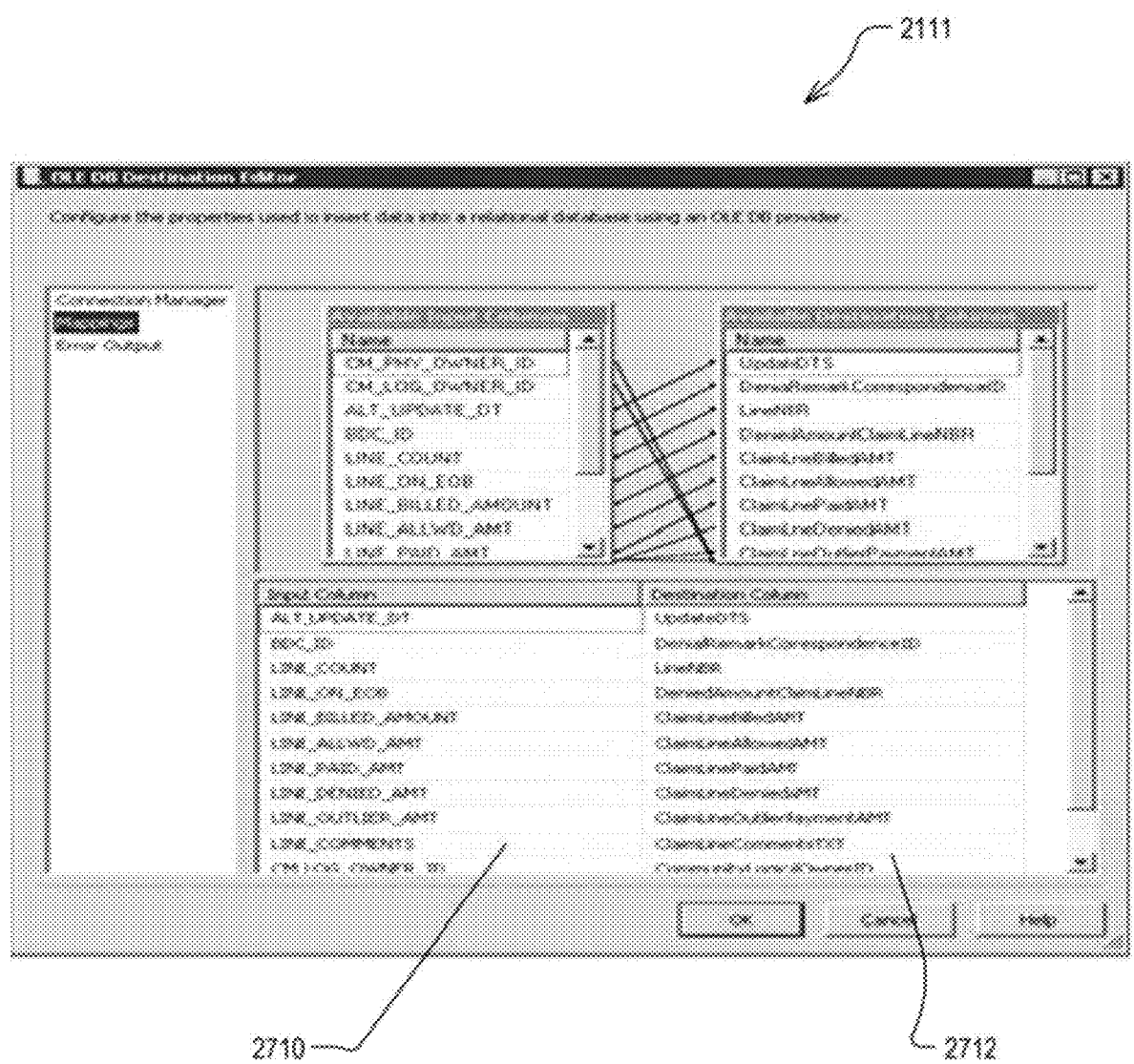
FIG. 27 illustrates an example column mapping table of FIG. 21.

The renaming of the columns from source system column names to those in the destination table uses a mapping table that was previously defined using SSIS OLE DB Destination Editor. FIG. 27 illustrates an example such mapping table 2111. While in the embodiment of FIG. 27 each source load package includes its own individual mapping table, it will be appreciated that in another embodiment, two or more, or all, of the mapping tables can be merged together into a single mapping table identifying a union of the mappings. In the embodiment of FIG. 27, it can be seen that mapping table 2111 includes one column 2710 containing the column names in the source system table, and a second column 2712 containing the column names to be used in the destination table. Thus in steps 2612 and 2614 (FIG. 26) respectively, the source mart package 2110 reads in the predefined column name mapping table and imports the columns from the temporary table into the destination source mart table, using the column name mappings. In one embodiment the importation step 2614 can be implemented by a data copy, whereas in another embodiment a mere column renaming operation may be sufficient. Also, note that in an SSIS implementation of source mart package 2110, no separate step need be programmed to read in the column name mapping table in step 2612. It is performed by SSIS Server automatically as needed. Finally, note that whereas steps 2610, 2612 and 2614 are shown in FIG. 26 as discrete steps, it will be appreciated that in some embodiments the process can be pipelined, at any granularity, including record-by-record. In the latter case each record can be thought of as a single-record temporary "table".

As mentioned, some source mart packages 2110 perform incremental loads rather than full loads. Those packages which load from base tables in the source system that are relatively small (e.g. less than one or two million records) are typically designed to perform full loads. Those packages which load from base tables in the source system that are larger are typically designed to perform incremental loads. An incremental load retains all records in the destination source mart table from the previous load, and imports only new records more recently added to the source system table.

Figure 28:
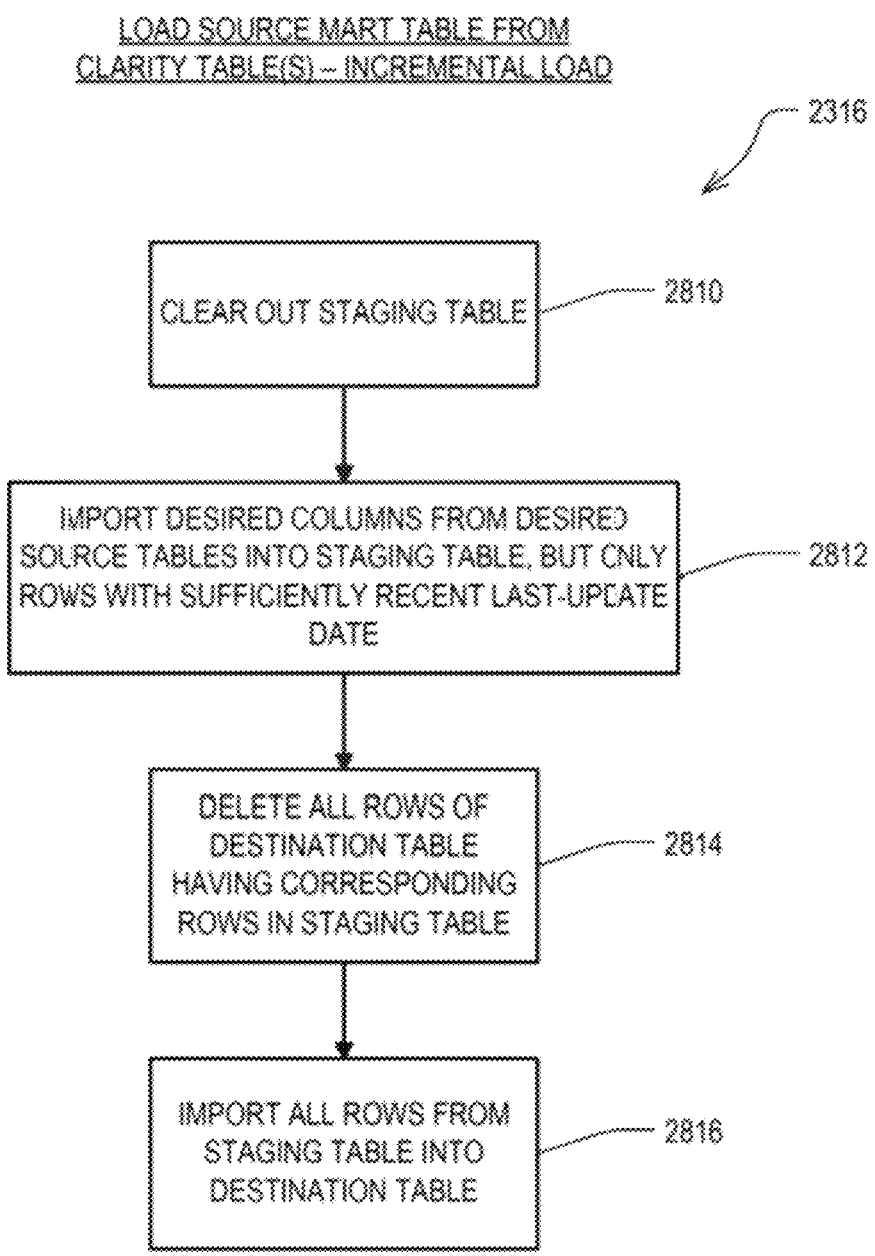

FIG. 28 is a flow chart detail of step 2316 for a source mart package 2110 that performs an incremental load of its destination table. In step 2810, instead of first clearing out the destination source mart table (step 2510, for an incremental load the source mart package 2110 clears out a staging table in step 2810. Then, instead of inserting the desired columns from the source tables directly into the destination source mart table in step 2510, for an incremental load the source mart package 2110 imports them into the staging table in step 2812. However, only "sufficiently recent" records from the source tables are imported in step 2812. Typically these are all records from the source tables that have a last-alter DTS which is less than some predetermined number of days (e.g. one day) earlier than the most recent update DTS in any record in the destination source mart table.

In step 2814, the source mart package 2110 deletes all records in the destination table which have a corresponding record in the staging table, and in step 2816 all records from the staging table are inserted into the destination table.

Figure 29:
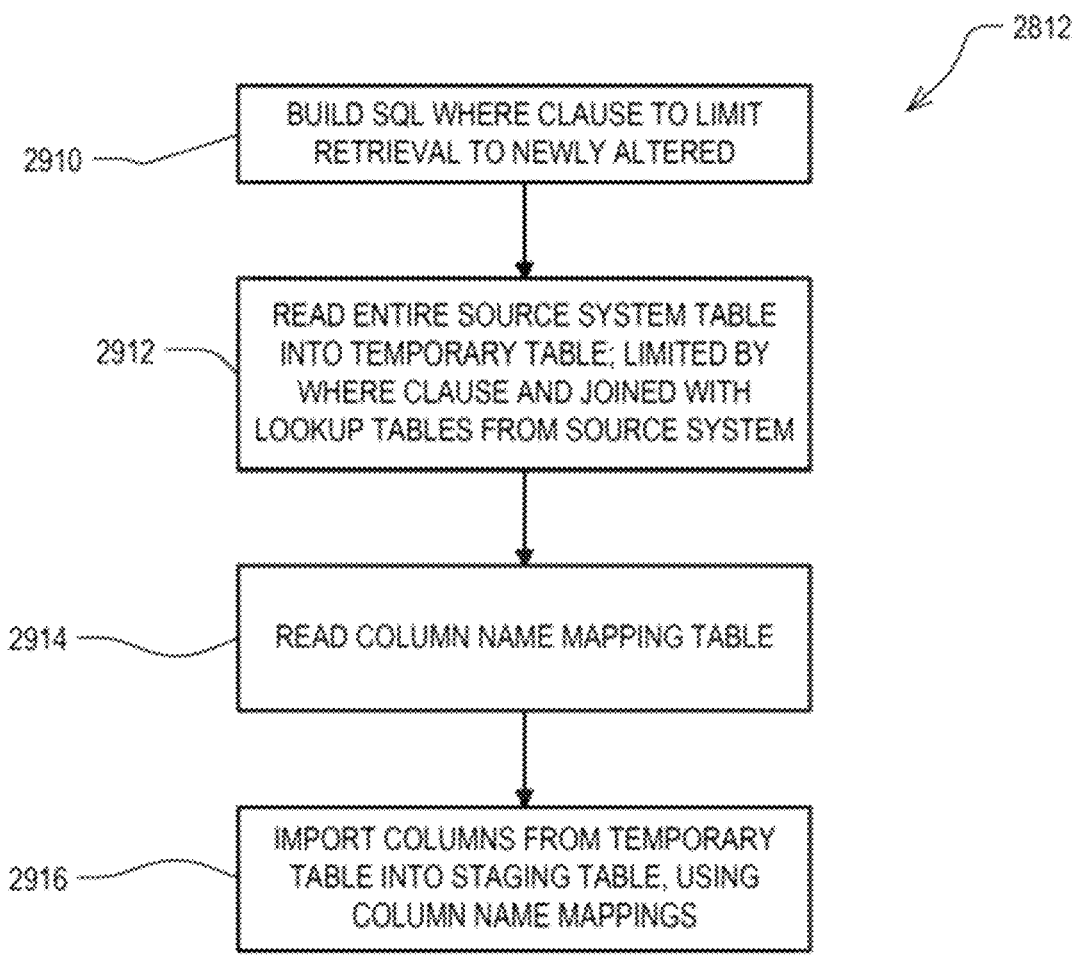

FIG. 29 is a flow chart detail of step 2812 for importing only sufficiently recent records from the source system tables into the staging table. The embodiment of FIG. 29 uses dynamic SQL to build and execute an appropriate SELECT statement. Thus in step 2910, the source mart package 2110 builds an SQL WHERE clause to limit record retrieval to only those records that were last altered sufficiently recently. In step 2912, like in step 2610, the source mart package 2110 reads the entire source system base table into a temporary table, joined with lookup tables from the source system as needed, but modified such that only the sufficiently recently altered records are retrieved. An SQL SELECT statement such as that used in step 2610 can be used, modified by adding the WHERE clause built in step 2910. Then, in a manner similar to steps 2612 and 2614, source mart package 2110 reads the column name mapping table in step 2914 and in step 2916 imports the columns from the temporary table in to the staging table, using the column name mappings.

Note that whereas the embodiment of FIG. 29 uses Dynamic SQL to build an appropriate WHERE clause, another embodiment can have a fixed WHERE clause which makes reference to a variable containing a previously calculated minimum acceptable last alter DTS. Also, whereas in the embodiment of FIG. 28 the column name mapping step is performed as data is first loaded into the staging table, it will be appreciated that in a different embodiment the column name mapping step can be delayed until data is imported from the staging table into the destination source mart table. Finally, all of the variations set forth above with respect to full load source mart packages apply equally with respect to incremental load packages.

Figure 30:
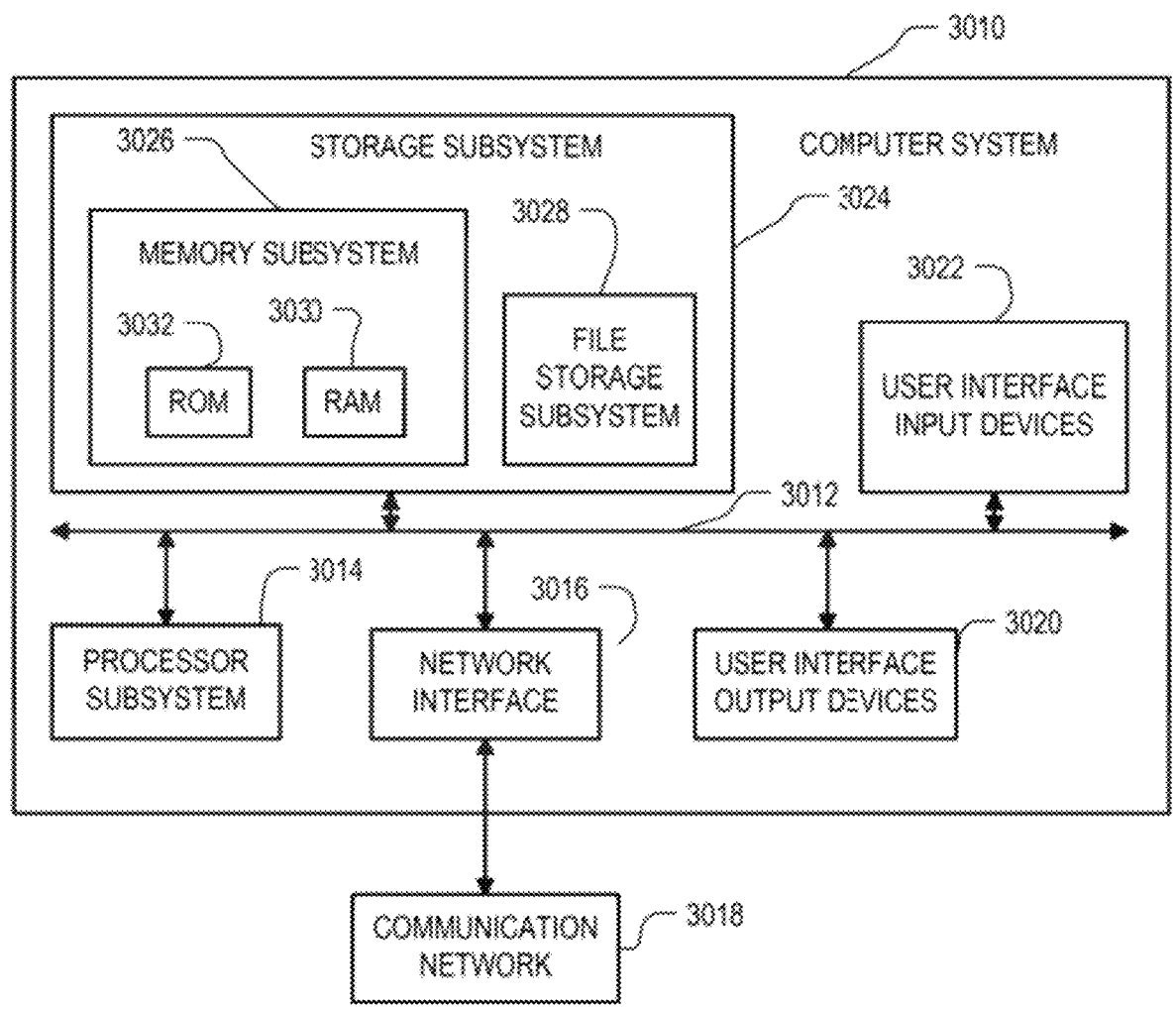
FIG. 30 is a simplified block diagram of a computer system that can be used to implement aspects of the present invention.

FIG. 30 is a simplified block diagram of a computer system 3010 that can be used to implement aspects of the present invention. While the flow charts herein indicate individual components as carrying out specified operations, it will be appreciated that each component actually causes the computer system 3010 to operate in the specified manner. The computer system 3010 is an example of any of the computing devices shown or described with respect to FIG. 17.

Computer system 3010 typically includes a processor subsystem 3014 which communicates with a number of peripheral devices via bus subsystem 3012. These peripheral devices may include a storage subsystem 3024, comprising a memory subsystem 3026 and a file storage subsystem 3028, user interface input devices 3022, user interface output devices 3020, and a network interface subsystem 3016. The input and output devices allow user interaction with computer system 3010. Network interface subsystem 3016 provides an interface to outside networks, including an interface to communication network 3018, and is coupled via communication network 3018 to corresponding interface devices in other computer systems. Communication network 3018 may comprise many interconnected computer systems and communication links. These communication links may be wireline links, optical links, wireless links, or any other mechanisms for communication of information, but typically it is an IP-based communication network. While in one embodiment, communication network 3018 is the Internet, in other embodiments, communication network 3018 may be any suitable computer network.

The physical hardware component of network interfaces are sometimes referred to as network interface cards (NICs), although they need not be in the form of cards: for instance they could be in the form of integrated circuits (ICs) and connectors fitted directly onto a motherboard, or in the form of macrocells fabricated on a single integrated circuit chip with other components of the computer system.

User interface input devices 3022 may include a keyboard, pointing devices such as a mouse, trackball, touchpad, or graphics tablet, a scanner, a touch screen incorporated into the display, audio input devices such as voice recognition systems, microphones, and other types of input devices. In general, use of the term "input device" is intended to include all possible types of devices and ways to input information into computer system 3010 or onto computer network 3018.

User interface output devices 3020 may include a display subsystem, a printer, a fax machine, or non visual displays such as audio output devices. The display subsystem may include a cathode ray tube (CRT), a flat panel device such as a liquid crystal display (LCD), a projection device, or some other mechanism for creating a visible image. The display subsystem may also provide non visual display such as via audio output devices. In general, use of the term "output device" is intended to include all possible types of devices and ways to output information from computer system 3010 to the user or to another machine or computer system.

Storage subsystem 3024 stores the basic programming and data constructs that provide the functionality of certain embodiments of the present invention. For example, the various modules implementing the functionality of certain embodiments of the invention may be stored in storage subsystem 3024. These software modules are generally executed by processor subsystem 3014.

Memory subsystem 3026 typically includes a number of memories including a main random access memory (RAM) 3030 for storage of instructions and data during program execution and a read only memory (ROM) 3032 in which fixed instructions are stored. File storage subsystem 3028 provides persistent storage for program and data files, and may include a hard disk drive, a floppy disk drive along with associated removable media, a CD ROM drive, an optical drive, or removable media cartridges. The databases and modules implementing the functionality of certain embodiments of the invention may have been provided on a computer readable medium such as one or more CD-ROMs, and may be stored by file storage subsystem 3028. The host memory 3026 contains, among other things, computer instructions which, when executed by the processor subsystem 3014, cause the computer system to operate or perform functions as described herein. As used herein, processes and software that are said to run in or on "the host" or "the computer", execute on the processor subsystem 3014 in response to computer instructions and data in the host memory subsystem 3026 including any other local or remote storage for such instructions and data.

Bus subsystem 3012 provides a mechanism for letting the various components and subsystems of computer system 3010 communicate with each other as intended. Although bus subsystem 3012 is shown schematically as a single bus, alternative embodiments of the bus subsystem may use multiple busses.

Computer system 3010 itself can be of varying types including a personal computer, a portable computer, a workstation, a computer terminal, a network computer, a television, a mainframe, a server farm, or any other data processing system or user device. Due to the ever changing nature of computers and networks, the description of computer system 3010 depicted in FIG. 30 is intended only as a specific example for purposes of illustrating the preferred embodiments of the present invention. Many other configurations of computer system 3010 are possible having more or less components than the computer system depicted in FIG. 30.

Source Mart Designer

Figure 31:
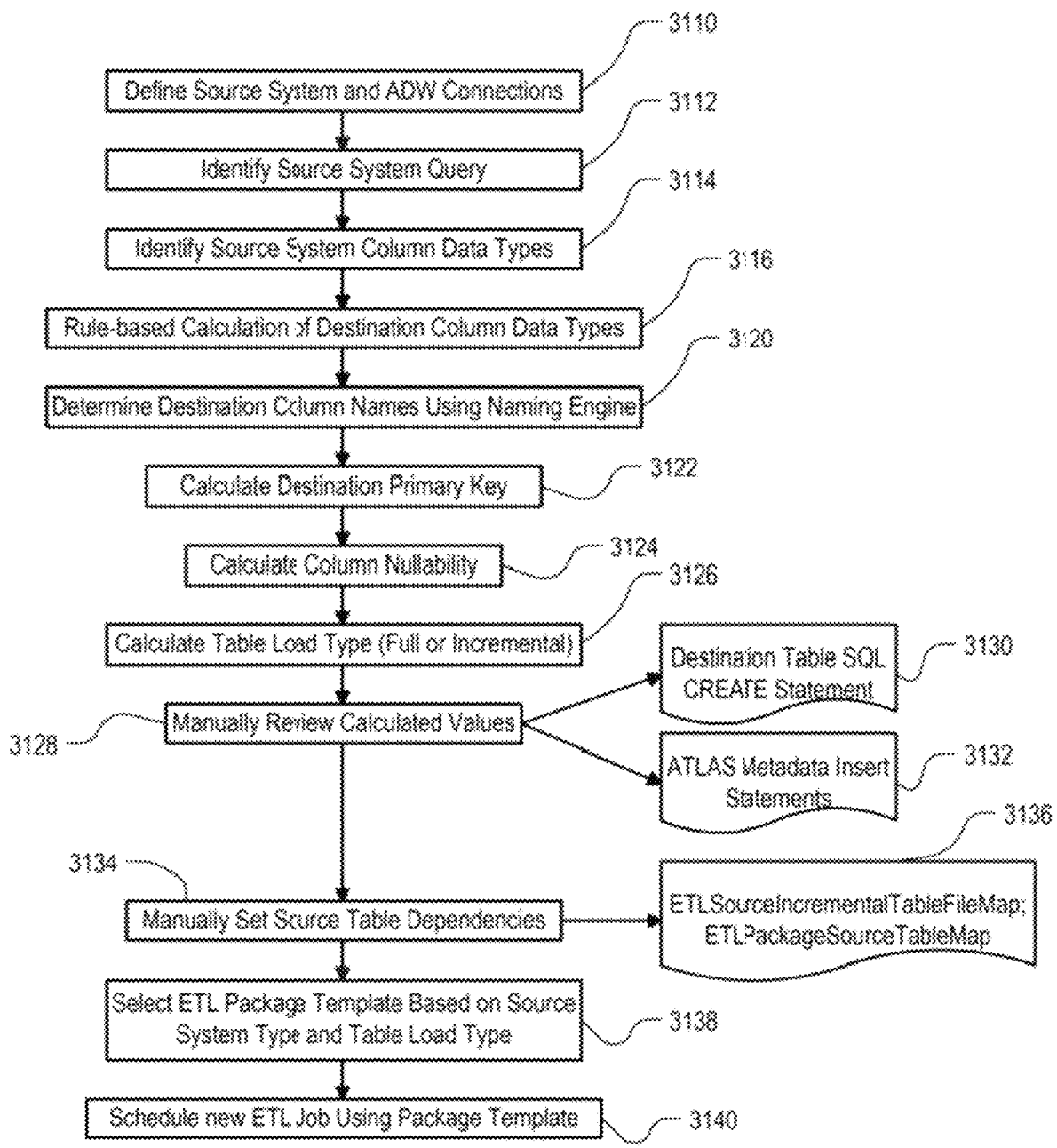
FIGS. 31-33 collectively illustrate a logic flow of the source mart designer of FIG. 21.

Many of the tasks involved in creating the source mart table load packages 2110 and the mapping tables 2116 and 2118 can be routinized in a pre-set flow, and many parts of that flow can be automated. The flow is represented in FIG. 21 as Source Mart Designer 2120. FIG. 31 is a flow chart setting forth an example of such flow.

In step 3110, the source and ADW connections are defined and configured into the source mart designer 2120. The source connection configuration includes a connection string which identifies the source database and the system that interfaces to it, and the information necessary to open an SQL connection to it. The ADW connection configuration includes a connection string used to access to the ADW database. This configuration enables access to the destination source mart table 604, the ETLSourceIncrementalTableFileMap 2116, and the ETLPackageSourceTableMap 2118. Step 3110 may also include configuring a path to where the log file is stored, as well as configuring an email connection used to send out error and alert emails, and an email list.

Figure 32:
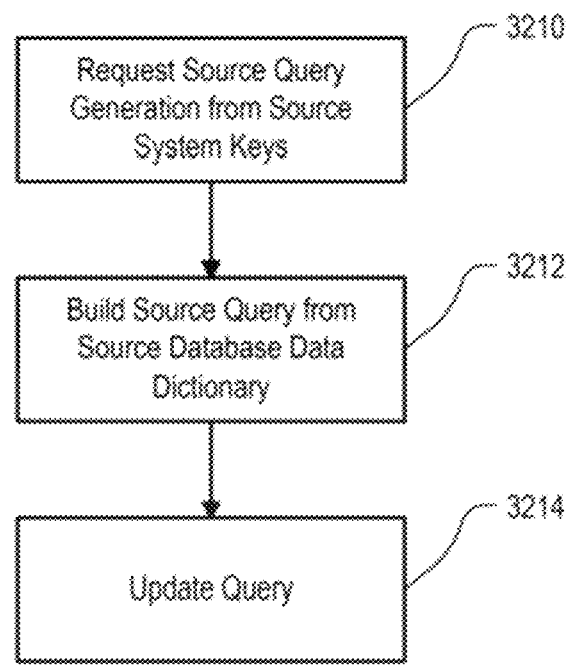

In step 3112, the system identifies a Source System Query for the current ETL package. This involves determining the SQL statement needed to read the source data into the destination table in the source mart 2110. As mentioned, the data for that table can come from one or more tables in the source system. FIG. 32 is a flow chart detail of that step, for use in certain embodiments. In the embodiment of FIG. 32, the table structure of the source database is discovered by dynamically querying the source system, and this information is what is used to build the SQL statement. Accordingly, referring to FIG. 32, in step 3210, the source mart designer 2120 requests information from the source system about the structure of its tables. In some embodiments this can be accomplished by querying a metadata table in the source system database. In steps 3212 and 3214, the source database structure information is used to build the main SELECT statement for importing all the data from the source system which will eventually be written into the destination ADW table. This SELECT statement contains all the SQL needed for importing the data needed for one destination source mart table, including the main source table joined with any required lookup tables in the source system. Typically the SELECT statement will retrieve all columns of the main source table. An example such SELECT statement, for use in a full load (non-incremental) of a destination source mart table from a Clarity source database system, might be:
SELECT
bdd. *
,zc.name
From '[MAIN_CLARITY_TABLE_NAME]' bdd
LEFT OUTER JOIN [ZC_ClarityTable_Name] zc ON zc.pk=bdd.fk
where bdd is an alias for the main clarity table to be imported, zc is a Clarity lookup table name prefix, pk is the primary key for the JOIN, and fk is the foreign key.

Returning to FIG. 31, in step 3114 the source mart designer 2120 identifies the source column data types for each column of the table(s) from which data will be retrieved. It obtains this information by querying the source database system. In step 3116, the source mart designer 2120 uses this information to calculate the Destination Data Types for columns in the destination source mart table. This involves several rules for converting the source system data types to a normalized set of data types used in the ADW 600. Some example rules are:

All Boolean types and Char(1) fields become Boolean types in the EDW

All varchar and nvarchar fields equal to or less than 255 characters become varchar(255)

All varchar and nvarchar fields over 255 become varchar (max)

Figure 33:
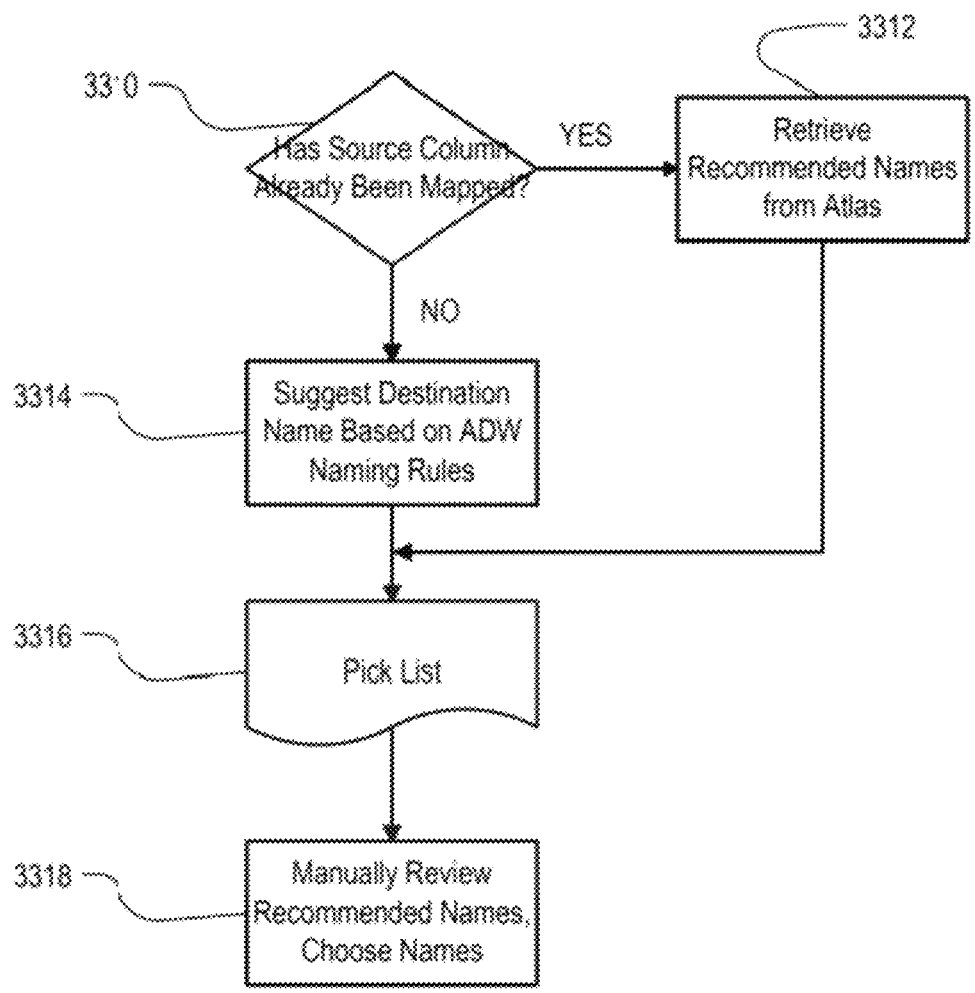

Names for destination columns in the ADW 600 are, as much as possible, consistent, human readable and self-explanatory. These names are determined in step 3120 and written into the mapping table 2111. The step preferably involves using an automated naming engine for each source column name. FIG. 33 is a flow chart detail of this step. Referring to FIG. 33, in step 3310, the source mart designer 2120 first determines whether the source column name has previously been mapped. This involves querying Atlas, which is a metadata database stored in the ADW 600. If so, then in step 3312 the previously mapped destination name is provided to a pick list 3316. If not, then in step 3314, one or more possible destination names, based on rules, are provided to the pick list. Some example rules are:

All fields that are numeric(38,0) must have a suffix from the following list
 ID
 NBR
 AMT
 QTY
 PCT
 SEQ
 CNT All underscores or other non-alphanumeric characters should be removed and the text after should be made Pascal-cased Then, in step 3318, the user manually selects a destination column name from the pick list. Alternatively, if the source column had previously been mapped (step 3312) then an embodiment of the system may skip the pick list 3316 and the manual review step 3318 and automatically map the source column name to the previously mapped destination column name. In yet another embodiment, the pick list 3316 and the manual review step 3318 are skipped even if the source column had not previously been mapped, by providing rules in step 3314 which always resolve to a single preferred destination column name.

Returning again to FIG. 31, in step 3122, the source mart designer 2120 calculates the destination primary key. Preferably this involves selecting the destination column name of whichever column the source system identified as the base source table's primary key. In an embodiment, the user can change this determination manually. In step 3124 the source mart designer 2120 calculates column nullability for each of the destination columns. Column nullability is a notation which indicates which destination columns are allowed to contain null values, and becomes part of the metadata for the destination table. Preferably the column nullability calculation is based on the nullability of the source table columns. In particular, in an embodiment, the only destination columns that are made nullable are those that are part of the primary key.

In step 3126 it is determined whether the load of the destination table will be a full load or an incremental load. As previously mentioned, those packages which load from base tables in the source system that are relatively small (e.g. less than one or two million records) are typically designed to perform full loads, whereas packages which load from larger base tables are typically designed to perform incremental loads. Preferably the table load type can be determined based on the number of records currently in the source system base table, and its rate of growth. In one embodiment, the determination can be made by first running a row count query on the source table, waiting P days (e.g. P=1), and then running the same query again. If a linear extrapolation of the table size indicates that within some predetermined time period (e.g. 10 years) the table will have more than a predetermined number of records (e.g. 1-2 million), then an incremental load is indicated. Otherwise, a full load is indicated. More specifically, an incremental load is indicated if:

$$B0+(BP-B0)/P*365*Y>M$$

where B0 is the row count from the first row count query, BP is the row count from the row count query run after P days, Y is the predetermined time period measured in years, and M is the predetermined number of records. This determination can be made manually or automatically.

In step 3128, the information developed above is used to generate the SQL CREATE statement 3130 for the destination table in the source mart. A typical CREATE statement for loading an Encounter table from an EPIC/CLARITY source might be:
  IF NOT EXISTS (SELECT * FROM INFORMATION_SCHEMA. SCHEMATA WHERE SCHEMA_NAME=N'Encounter')
    EXEC sys.sp_executesql N'CREATE SCHEMA [Encounter]'
  IF EXISTS (SELECT * FROM INFORMATION_SCHEMA.TABLES WHERE TABLE_SCHEMA=N'Encounter' AND TABLE_NAME=N'PatientMetadata')
    DROP TABLE [Encounter].[PatientMetadata]
  CREATE TABLE [Encounter].[PatientMetadata](
    ColumnID numeric(38, 0) NOT NULL,
    TableID numeric(38, 0),
    ColumnNM varchar(255),
    DescriptionTXT varchar(max),
    DescriptionlastupdateDTS datetime,
    DatatypeTXT varchar(255),
    ExampledataTXT varchar(max),
    ScrambleexampledataFLG char(1),
    SourcesystemNM varchar(255),
    SourcetableNM varchar(255),
    SourcecolumnNM varchar(255),
    ColumnaliasNM varchar(255),
    PrimarykeyFLG char(1)
  )
  ALTER TABLE [Encounter].[PatientMetadata] ADD CONSTRAINT [pkPatientMetadata] PRIMARY KEY CLUSTERED
  (
    [ColumnID] ASC
  )
  ALTER TABLE [Encounter].[PatientMetadata] REBUILD WITH (DATA_COMPRESSION=PAGE)

The information developed above is also used to create SQL Insert statements 3132 for writing the metadata into the ADW Atlas Metadata tables. These statements typically are execute only once (optionally at this point in the flow), unless table structure information changes. Therefore, in one embodiment they are not inserted into the source mart ETL package currently being developed. Also, preferably but not essentially, the user can be offered an opportunity to review the calculated values manually before these statements are executed.

In step 3134, the source table dependencies for loading the current destination table are determined. This can be accomplished automatically by scanning the source system query from step 3114, and detecting all source system tables mentioned in the SELECT statement. Preferably but not essentially the detected table dependencies can be offered to the user for manual modification. The resulting list of table dependencies is then written into the ADW tables ETLSourceIncrementalTableFileMap 2116 and ETLPackageSourceTableMap 2118 using SQL INSERT statements. If the loading the current destination table also must await any package load dependencies, for example packages that load Patient and Provider information, then step 3134 includes flagging whether to await these packages or listing packages to await.

In step 3138 the source mart ETL package is prepared and written to the ADW 600. In one embodiment, the package is written line by line based on the information developed above. In another embodiment, templates are used, which have been previously developed for each permutation of a source database system type (e.g. EPIC, PeopleSoft or Cerner) and source mart 604. In the latter embodiment, step 3138 involves selecting the appropriate package template and customizing it according to the information developed above. In either case, the ETL package also includes the SQL statements and SSIS steps so as to perform the insertion of data into the destination source mart table as set forth in FIG. 25 (for a full table load) or 29 (for an incremental table load).

In step 3140 the ETL package is scheduled in the ADW/SSIS Server 600 to run at desired times. Preferably, it is scheduled to run nightly.

As used herein, a given event or value is "responsive" to a predecessor event or value if the predecessor event or value influenced the given event or value. If there is an intervening processing element, step or time period, the given event or value can still be "responsive" to the predecessor event or value. If the intervening processing element or step combines more than one event or value, the event or value output of the processing element or step is considered "responsive" to each of the event or value inputs. If the given event or value is the same as the predecessor event or value, this is merely a degenerate case in which the given event or value is still considered to be "responsive" to the predecessor event or value. "Dependency" of a given event or value upon another event or value is defined similarly.

As used herein, the "identification" of an item of information does not necessarily require the direct specification of that item of information. Information can be "identified" in a field by simply referring to the actual information through one or more layers of indirection, or by identifying one or more items of different information which are together sufficient to determine the actual item of information. In addition, the term "indicate" is used herein to mean the same as "identify".

Although the invention has been described with reference to specific embodiments, it will be understood by those skilled in the art that various changes can be made without departing from the spirit or scope of the invention. Accordingly, the disclosure of embodiments is intended to be illustrative of the scope of the invention and is not intended to be limiting. It is intended that the scope of the invention shall be limited only to the extent required by the appended claims. To one of ordinary skill in the art, it will be readily apparent that systems and methods discussed herein may be implemented in a variety of embodiments, and that the foregoing discussion of certain of these embodiments does not necessarily represent a complete description of all possible embodiments. Rather, the detailed description of the drawings, and the drawings themselves, disclose at least one embodiment, and may disclose alternative embodiments.

What is claimed is:

1. A method comprising:
   determining, using one or more processors, that a first set of load dependencies associated with a first source mart is satisfied; and
   responsive to determining that the first set of load dependencies associated with the first source mart is satisfied, gathering, using the one or more processors, data from a set of source database systems associated with the first source mart and storing the data in the first source mart, wherein the first source mart includes a common linkable identifier, the common linkable identifier linked to a first identifier in a first source database system and a second identifier in a second source database system.

2. The method of claim 1, wherein the first set of load dependencies associated with the first source mart includes a first subset of tables being up-to-date, wherein the first subset of tables is included in the set of source database systems associated with the first source mart.

3. The method of claim 2 further comprising:
   determining that a second set of load dependencies associated with the first source mart is satisfied; and
   responsive to determining that the second set of load dependencies associated with the first source mart is satisfied, gathering data from the set of source database systems associated with the first source mart and storing the data in the first source mart.

4. The method of claim 3, wherein the second set of load dependencies associated with the first source mart includes a second subset of tables being up-to-date, wherein the second subset of tables is included in the set of source database systems associated with the first source mart.

5. The method of claim 4, wherein the first set of tables and the second subset of tables include one or more tables in common.

6. The method of claim 1, wherein determining that that the first set of load dependencies associated with the first source mart is satisfied includes determining that a first subset of tables is up-to-date, wherein the first subset of tables is included in the set of source database systems associated with the first source mart.

7. The method of claim 1 further comprising:
   extracting data from the first source mart based on one or more selected criteria;
   manipulating the data extracted from the first source mart; and
   storing the manipulated data in a subject area mart.

8. The method of claim 7, wherein the one or more selected criteria include one or more of a treatment ordering criteria, a delivery treatment criteria, and a patient safety treatment criteria.

9. The method of claim 7, wherein the subject area mart includes:
   a pre-cohort table, wherein a pre-cohort is defined from a population;
   a cohort table, wherein the cohort is a subset of the pre-cohort; and
   a metric table.

10. A system comprising:
    one or more processors; and
    a memory storing instructions that, when executed by the one or more processors, cause the system to:
    determine that a first set of load dependencies associated with a first source mart is satisfied; and
    responsive to determining that the first set of load dependencies associated with the first source mart is satisfied, gather data from a set of source database systems associated with the first source mart and storing the data in the first source mart, wherein the first source mart includes a common linkable identifier, the common linkable identifier linked to a first identifier in a first source database system and a second identifier in a second source database system.

11. The system of claim 10, wherein the first set of load dependencies associated with the first source mart includes a first subset of tables being up-to-date, wherein the first subset of tables is included in the set of source database systems associated with the first source mart.

12. The system of claim 11 further comprising:
    determining that a second set of load dependencies associated with the first source mart is satisfied; and
    responsive to determining that the second set of load dependencies associated with the first source mart is satisfied, gathering data from the set of source database systems associated with the first source mart and storing the data in the first source mart.

13. The system of claim 12, wherein the second set of load dependencies associated with the first source mart includes a second subset of tables being up-to-date, wherein the second subset of tables is included in the set of source database systems associated with the first source mart.

14. The system of claim 13, wherein the first set of tables and the second subset of tables include one or more tables in common.

15. The system of claim 10, wherein determining that that the first set of load dependencies associated with the first source mart is satisfied includes determining that a first subset of tables is up-to-date, wherein the first subset of tables is included in the set of source database systems associated with the first source mart.

16. The system of claim 10, wherein the instructions, when executed by the one or more processors further cause the system to:
    extract data from the first source mart based on one or more selected criteria;

manipulate the data extracted from the first source mart; and store the manipulated data in a subject area mart.

17. The system of claim 16, wherein the one or more selected criteria include one or more of a treatment ordering criteria, a delivery treatment criteria, and a patient safety treatment criteria.

18. The system of claim 16, wherein the subject area mart includes:
- a pre-cohort table, wherein a pre-cohort is defined from a population;
- a cohort table, wherein the cohort is a subset of the pre-cohort; and
- a metric table.

* * * * *